(12) United States Patent
Miao

(10) Patent No.: US 9,180,214 B1
(45) Date of Patent: Nov. 10, 2015

(54) GONADOTROPIN-RELEASING HORMONE RECEPTOR-TARGETING PEPTIDES AND THEIR USE TO TREAT AND DIAGNOSE CANCER

(75) Inventor: Yubin Miao, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 559 days.

(21) Appl. No.: 13/447,918

(22) Filed: Apr. 16, 2012

Related U.S. Application Data

(60) Provisional application No. 61/478,414, filed on Apr. 22, 2011.

(51) Int. Cl.
| | |
|---|---|
| A61K 51/00 | (2006.01) |
| A61K 36/14 | (2006.01) |
| A61K 51/08 | (2006.01) |
| A61K 38/08 | (2006.01) |

(52) U.S. Cl.
CPC .............. *A61K 51/088* (2013.01); *A61K 38/08* (2013.01)

(58) Field of Classification Search
CPC ..... A61K 51/00; A61K 51/08; A61K 51/088; A61K 2123/00; A61K 2121/00; A61K 38/00; A61K 38/1709; A61K 38/04; A61K 38/08; A61K 38/09; A61K 38/12; A61K 38/24; A61K 38/22; A61K 39/00; C07K 7/06; C07K 7/08; C07K 7/00; C07K 7/04; C07K 7/50; C07K 7/23; C07K 7/52; C07K 2319/00; C07F 5/00; C07D 225/00; C07D 225/02
USPC ........... 424/1.11, 1.65, 1.69, 1.73, 1.81, 1.85, 424/1.89, 9.1, 9.2, 9.3, 9.4, 9.5; 514/1, 1.1, 514/19.2, 19.3, 19.4, 19.5, 19.6, 21.6; 530/300, 313, 317, 328; 534/7, 10–16
See application file for complete search history.

(56) References Cited

U.S. PATENT DOCUMENTS

2012/0045393 A1* 2/2012 Linder et al. .................. 424/1.69

OTHER PUBLICATIONS

Schottelius et al, Bioconjugate Chemistry, 2008, vol. 19, No. 6, pp. 1256-1268.*
Jemal, A.; Siegel, R.; Xu, J.; Ward, E. CA Cancer J. Clin. 2010, 60, 277.
Pienta, K. J.; Naik, H.; Lehr, J. E. Urology 1996, 48, 164.
Naik, H.; Lehr, J. E.; Pienta, K. J. Urology 1996, 48, 508.
Yogoda, A.; Petrylak, D. Cancer 1993, 71, 1098.
Crawford, E. D.; Blumenstein, B. A.; Goodman, P. J.; Davis, M. A.; Eisenberger, M. A.; McLeod, D. G.; Spaulding, J. T.; Benson, R.; Dorr, F. A. Cancer 1990, 66 (suppl. 5), 1039.
Oesterling, J. E. J. Urol. 1991, 145, 907.
Hudson, M. A.; Bahnson, R. R.; Catalona, W. T. J. Urol. 1989, 142, 1011.
Stephan, C.; Cammann, H.; Meyer, H. A.; Lein, M.; Jung, K. Cancer lett. 2007, 249, 18.
Kahn, D.; Williams, R. D.; Seldin, D. W.; Libertino, J. A.; Hirschhorn, M.; Dreicer, R.; Weiner, G. J.; Bushnell, D.; Gulfo, J. J. Urol. 1994, 152, 1490.
Kahn, D.; William, R. D.; Manyak, M. J.; Haseman, M. K.; Seldin, D. W.; Libertino, J. A.; Maguire, R. T. J. Urol. 1998, 159, 2041.
Kahn, D.; Williams, R. D.; Haseman, M. K.; Reed, N. L.; Miller, S. J.; Gerstbrein, J. J. Clin. Oncol. 1998, 16, 284.
Hinkle, G. H.; Burgers, J. K.; Neal, C. E.; Texter, J. H.; Kahn, D.; Williams, R. D.; Maguire, R.; Rogers, B.; Olsen, J. O.; Badalament, R. A. Cancer 1998, 83, 739.
Chang, C. H.; Wu, H. C.; Tsai, J. J.; Shen, Y. Y.; Changlai, S. P.; Kao, A. Urol. Int. 2003, 70, 311.
Heicappell, R.; Muller-Mattheis, V.; Reinhardt, M.; Vosberg, H.; Gerharz, C. D.; Muller-Gartner, H.; Ackermann, R. Eur. Urol. 1999, 36, 582.
Shreve, P. D.; Grossmann, H. B.; Gross, M. D.; Wahl, R. L. Radiology 1996, 199, 751.
Effert, P. J.; Bares, R.; Handt, S.; Wolff, J. M.; Bull, U.; Jakse, G. J. Urol. 1996, 155, 994.
Limonta, P.; Dondi, D.; Moretti, R. M.; Maggi, R.; Motta, M. J. Clin. Endocrinol. Metab. 1992, 75, 207.
Limonta, P.; Dondi, D.; Moretti, R. M.; Fermo, D.; Garattini, E.; Motta, M. J. Clin. Endocrinol. Metab. 1993, 76, 797.
Dondi, D.; Limonta, P.; Moretti, R. M.; Montagnani, M. M.; Garattini, E.; Motta, M. Cancer Res. 1994, 54, 4091.
Limonta, P.; Moretti, R. M.; Montagnani, M. M.; Dondi, D.; Parenti, M.; Motta, M. Endocrinology 1999, 140, 5250.
Straub, B.; Muller, M.; Krause, H.; Schrader, M.; Goessl, C.; Heicappell, R.; Miller, K. Clin. Cancer Res. 2001, 7, 2340.
Halmos, G.; Arencibia, J. M.; Schally, A. V.; Davis, R.; Bostwick, D. G. J. Urol. 2000, 163, 623.

(Continued)

*Primary Examiner* — D L Jones
(74) *Attorney, Agent, or Firm* — Henry D. Coleman; R. Neil Sudol

(57) ABSTRACT

The present invention is directed to novel non-invasive diagnostic tools/compounds to image and treat cancers, especially cancers which overexpress GnRH such as breast cancer, prostate cancer and melanoma, among others, including metastatic breast cancer, prostate cancer and/or melanoma among numerous others in vivo. The novel imaging probes are capable of detecting cancerous cells, as well as their metastatic spread in tissues. The novel probes of the present invention will also be useful to initiate therapy for breast and/or prostate cancer, among other cancers, as well as monitor patients' response to chemotherapy treatments and other interventions or therapies used in the treatment of cancer, including metastatic cancer as otherwise described herein. Compounds according to the present invention may be used as diagnostic tools for diagnosing cancer as well as therapeutic agents for treating cancer and related secondary disease states and conditions.

33 Claims, 10 Drawing Sheets

(56) References Cited

OTHER PUBLICATIONS

Tieva, A.; Stattin, P.; Wikstrom, P.; Bergh, A.; Damber, J. E. Prostate 2001, 47, 276.

Fekete, M.; Zalatnai, A.; Comaru-Schally, A. M.; Schally, A. V. Pancreas 1989, 4, 521.

Grundker, C.; Volker, P.; Griesinger, F.; Ramaswamy, A.; Nagy, A.; Schally, A. V.; Emons, G. Am. J. Obstet. Gynecol. 2002, 187, 528.

Millar, R. P. Animal Reproduction Sci. 2005, 88, 5.

Barda, Y.; Cohen, N.; Lev, V.; Ben-Aroya, N.; Koch, Y.; Mishani, E.; Fridkin, M.; Gilon, C. Nuc. Med. Biol. 2004, 31, 921.

Beckers, T.; Bernd, M.; Kutscher, B.; Kuhne, R.; Hoffman, S.; Reissmann, T. Biochem. Biophys. Res. Commun. 2001, 289, 653.

Guo, H.; Lu, J.; Hathaway, H.; Royce, M. E.; Prossnitz, E. R.; Miao, Y. Bioconjug. Chem. 2011, 22, 1682.

Schottelius, M.; Berger, S.; Poethko, T.; Schwaiger, M.; Wester, H. J. Bioconjug. Chem. 2008, 19, 1256.

Guo, H.; Yang, J.; Gallazzi, F.; Prossnitz, E. R.; Sklar, L. A.; Miao, Y. Bioconjug. Chem. 2009, 20, 2162.

Hoffman, T. J.; Gali, H.; Smith, C. J.; Sieckman, G. L.; Hayes, D. L.; Owen, N. K.; Volkert, W. A. J. Nucl. Med. 2003, 44, 823.

Jemal, A., Siegel, R., Xu, J., and Ward, E. (2010) Cancer statistics. CA Cancer J. Clin. 60, 277-300.

Buist, D. S., Porter, P. L., Lehman, C., Taplin, S. H., and White, E. (2004) Factors contributing to mammography failure in women aged 40-49 years. J. Natl. Cancer Inst. 96, 1432-1440.

Gambhir, S. S. (2002) Molecular imaging of cancer with positron emission tomography. Nat. Rev. Cancer 2, 683-693.

Sharma, V., Luker, G. D., and Piwnica-Worms, D. (2002) Molecular imaging of gene expression and protein function in vivo with PET and SPECT. J. Magn. Reson. Imaging 16, 336-351.

Bos, R., van Der Hoeven, J. J., van Der Wall, E., van Der Groep, P., van Diest, P. J., Comans, E. F., Joshi, U., Semenza, G. L., Hoekstra, O. S., Lammertsma, A. A., and Molthoff, C. F. (2002) Biologic correlates of 18fluorodeoxyglucose uptake in human breast cancer measured by positron emission tomography. J. Clin. Oncol. 20, 379-387.

Avril, N., Menzel, M., Dose, J., Schelling, M., Weber, W., Janicke, F., Nathrath, W., and Schwaiger, M. (2001) Glucose metabolism of breast cancer assessed by 18F-FDG PET: histologic and immunohistochemical tissue analysis. J. Nucl. Med. 42, 9-16.

Mankoff, D. A., Dunnwald, L. K., Gralow, J. R., Ellis, G. K., Charlop, A., Lawton, T. J., Schubert, E. K., Tseng, J., and Livingston, R. B. (2002) Blood flow and metabolism in locally advanced breast cancer: relationship to response to therapy. J. Nucl. Med. 43, 500-509.

Oshida, M., Uno, K., Suzuki, M., Nagashima, T., Hashimoto, H., Yagata, H., Shishikura, T., Imazeki, K., and Nakajima, N. (1998) Predicting the prognoses of breast carcinoma patients with positron emission tomography using 2-deoxy-2-fluoro[18F]-D-glucose. Cancer 90, 2227-2234.

Inoue, T., Yutani, K., Taguchi, T., Tamaki, Y., Shiba, E., and Noguchi, S. (2004) Preoperative evaluation of prognosis in breast cancer patients by [(18)F]2-Deoxy-2-fluoro-D-glucose-positron emission tomography. J. Cancer Res. Clin. Oncol. 130, 273-278.

Avril, N., Rose, C. A., Schelling, M., Dose, J., Kuhn, W., Bense, S., Weber, W., Ziegler, S., Graeff, H., and Schwaiger, M. (2000) Breast imaging with positron emission tomography and fluorine-18 fluorodeoxyglucose: use and limitations. J. Clin. Oncol. 18, 3495-3502.

Eubank, W. B., Mankoff, D. A., Takasugi, J., Vesselle, H., Eary, J. F., Shanley, T. J., Gralow, J. R., Charlop, A., Ellis, G. K., Lindsley, K. L., Austin-Seymour, M. M., Funkhouser, C. P., and Livingston, R. B. (2001) 18Fluorodeoxyglucose positron emission tomography to detect mediastinal or internal mammary metastases in breast cancer. J. Clin. Oncol. 19, 3516-3523.

Isasi, C. R., Moadel, R. M., and Blaufox, M. D. (2005) A meta-analysis of FDG PET for the evaluation of breast cancer recurrence and metastases. Breast Cancer Res. Treat. 90, 105-112.

Lonneux, M., Borbath, I. I., Berliere, M., Kirkove, C., and Pauwels, S. (2000) The place of whole-body PET FDG for the diagnosis of distant recurrence of breast cancer. Clin. Positron Imaging 3, 45-49.

Vranjesevic, D., Filmont, J. E., Meta, J., Silverman, D. H., Phelps, M. E., Rao, J., Valk, P. E., and Czemin, J. (2002) Whole-body (18)F-FDG PET and conventional imaging for predicting outcome in previously treated breast cancer patients. J. Nucl. Med. 43, 325-329.

Cook, G. J., Houston, S., Rubens, R., Maisey, M. N., and Fogelman, I. (1998) Detection of bone metastases in breast cancer by 18FDG PET: differing metabolic activity in osteoblastic and osteolytic lesions. J. Clin. Oncol. 16, 3375-3379.

Miller, W. R., Scott, W. N., Morris, R., Fraser, H. M., and Sharpe, R. M. (1985) Growth of human breast cancer cells inhibited by a luteinizing hormone-releasing hormone agonist. Nature 313, 231-233.

Eidne, K. A., Flanagan, C. A., and Millar, R. P. (1985) Gonadotropin-releasing hormone binding sites in human breast carcinoma. Science 229, 989-991.

Sharoni, Y., Bosin, E., Miinster, A., Levy, J., and Schally, A. V. (1989) Inhibition of growth of human mammary tumor cells by potent antagonists of luteinizing hormone-releasing hormone. Proc. Natl. Acad. Sci. U.S.A. 86, 1648-1651.

Fekete, M., Wittliff, J. L., and Schally, A. V. (1989) Characteristics and distribution of receptors for [d-Trp6]-luteinizing hormone-releasing hormone, somatostatin, epidermal growth factor and sex steroids in 500 biopsy samples of human breast cancer. J. Clin. Lab. Anal. 3, 137-147.

Baumann, K. H., Kiesel, L., Kaufmann, M., Bastert, G., and Runnebaum, B. (1993) Characterization of binding sites for a GnRH-agonist (buserelin) in human breast cancer biopsies and their distribution in relation to tumor parameters. Breast Cancer Res. Treat. 25, 37-46.

Millar, R. P. (2005) GnRH and GnRH receptors. Animal Reproduction Sci. 88, 5-28.

Beckers, T., Bernd, M., Kutscher, B., Kuhne, R., Hoffman, S., and Reissmann, T. (2001) Structure-function studies of linear and cydized peptide antagonists of the GnRH receptor. Biochem. Biophys. Res. Commun. 289, 653-663.

Nagy, A., Schally, A.V., Armatis, P., Szepeshazi, K., Halmos, G., Kovacs, M., Zarandi, M., Groot, K., Miyazaki, M., Jungwirth, A., and Horvath, J. (1996) Cytotoxic analogs of luteinizing hormone-releasing hormone containing doxorubicin or 2-pyrrolinodoxorubicin, a derivative 500-1000 times more potent. Proc. Natl. Sci. U.S.A. 93, 7269-7273.

Halmos, G., Nagy, A., Lamharzi, N., and Schally, A. V. (1999) Cytotoxic analogs of luteinizing hormone-releasing hormone bind with high affinity to human breast cancers. Cancer Lett. 136, 129-136.

Wang, X., Krebs, L. J., Al-Nuri, M., Pudavar, H. E., Ghosal, S., Liebow, C., Nagy, A. A., Schally, A. V., and Prasad, P. N. (1999) A chemically labeled cytotoxic agent: two-photon fluorophore for optical tracking of cellular pathway in chemotherapy. Proc. Natl. Acad. Sci. U.S.A. 96, 11081-11084.

Szepeshazi, K., Schally, A. V., Nagy, A., Halmos, G., and Groot, K. (1997) Targeted cytotoxic luteinizing hormone releasing hormone (LH-RH) analogs inhibit growth of estrogen-independent MXT mouse mammary cancer in vivo by decreasing cell proliferation and inducing apoptosis. Anticancer Drugs 8, 974-987.

Szepeshazi, K., Schally, A. V., and Nagy, A. (1999) Effective treatment of advanced estrogen-independent MXT mouse mammary cancers with targeted cytotoxic LH-RH analogs. Breast Cancer Res. Treat. 56, 267-276.

Kahan, Z., Nagy, A., Schally, A. V., Halmo, G., Arencibia, J. M., and Groot, K. (1999) Complete regression of MX-1 human breast cancer xenografts after targeted chemotherapy with a cytotoxic analog of luteinizing hormone-releasing hormone, AN-207. Cancer 85, 2608-2615.

Bajo, A. M., Schally, A. V., Halmos, G., and Nagy, A. (2003) Targeted doxorubicincontaining luteinizing hormone-releasing hormone analogue AN-152 inhibits the growth of doxorubicin-resistant MX-1 human breast cancer. Clin. Cancer Res. 9, 3742-3748.

Kahan, Z., Nagy, A., Schally, A. V., Halmos, G., Arencibia, J. M., and Groot, K. (2000) Administration of a targeted cytotoxic analog of luteinizing hormone releasing hormone inhibits growth of estrogen

(56) References Cited

OTHER PUBLICATIONS independent MDA-MB-231 human breast cancers in nude mice. Breast Cancer Res. Treat. 59, 255-262.

Chatzistamou, I., Schally, A. V., Nagy, A., Armatis, P., Szepeshazi, K., and Halmos, G. (2000) Effective treatment of metastatic MDA-MD-435 human estrogen independent breast carcinomas with a targeted cytotoxic analog of luteinizing hormone-releasing hormone, AN-207. Clin, Cancer Res. 6, 4158-4165.

Flanagan, C. A., Fromme, B. J., Davidson, J. S., and Millar, R. P. (1998) A high affinity gonadotropin-releasing hormone (GnRH) tracer, radioiodinated at position 6, facilitates analysis of mutant GnRH receptors. Endocrinology 139, 4115-4119.

Guo, H., Yang, J., Gallazzi, F., and Miao, Y. (2010) Reduction of the ring size of radiolabeled lactam bridge-cyclized α-MSH peptide, resulting in enhanced melanoma uptake. J. Nucl. Med. 51, 418-426.

Scopinaro, F., Varvarigou, A. D., Ussof, W., De Vincentis, G., Sourlingas, T. G., Evangelatos, G. P., Datsteris, J., and Archimandritis, S. C. (2002) Technetium-labeled bombesin-like peptide: preliminary report on breast cancer uptake in patients. Cancer Biother. Radiopharm. 17, 327-335.

Van de Wiele, C., Dumont, F., Broecke, R. V., Oosterlinck, W., Cocquyt, V., Serreyn, R., Peers, S., Thornback, J., Slegers, G., and Dierck, R. A. (2000) Technetium-99m RP527, a GRP analogue for visualization of GRP receptor-expresssing malignancies: a feasibility study. Eur. J. Nucl. Med. 27, 1694-1699.

Prasanphanich, A. F., Retzloff, L., Lane, S. R., Nanda, P. K., Sieckman, G. L., Rold, T. L., Ma, L., Figueroa, S. D., Sublett, S. V., Hoffman, T. J., Smith, C. J. (2009) In vitro and in vivo analysis of [64Cu-NO2A-8-Aoc-BBN(7-14)NH2]: a site-directed radiopharmaceutical for positron-emission tomography imaging of T-47D human breast cancer tumors. Nucl. Med. Biol. 36,171-181.

Retzloff, L., Heinzke, L., Figueroa, S. D., Sublett, S. V., Ma, L., Sieckman, G. L., Rold, T. L., Santos, I., Hoffman, T. J., Smith, C. J. (2010) Evaluation of [99mTc-(CO)3-X-Y-Bombesin(7-14)NH2] conjugates for targeting gastrin-releasing peptide receptors overexpressed on breast carcinoma. Anticancer Res. 30, 19-30.

Gali, H., Hoffman, T. J., Sieckman, G. L., Owen, N. K., Katti, K. V., and Volkert, W. A. (2001) Synthesis, characterization, and labeling with 99m Tc/188Re of peptide, conjugates containing a dithia-bisphosphine chelating agent. Bioconjug. Chem. 12, 354-63.

Barda, Y., Cohen, N., Lev, V., Ben-Aroya, N., Koch, Y., Mishani, E., Fridkin, M., and Gilon, C. (2004) Backbone metal cyclization: novel 99mTc labeled GnRH analog as potential SPECT molecular imaging agent in cancer. Nucl. Med. Biol. 31, 921-933.

Schottelius, M., Berger, S., Poethko, T., Schwaiger, M., and Wester, H. J. (2008) Development of novel 68Ga- and 18F-labeled GNRH-I analogues with high GNRHR-targeting efficiency. Bioconjun. Chem. 19, 1256-1268.

Guo, H., Yang, J., Gallazzi, F., Prossnitz, E. R., Sklar, L. A., and Miao, Y. (2009) Effect of DOTA position on melanoma targeting and pharmacokinetic properties of 111In-labeled lactam bridge-cyclized alpha-melanocyte stimulating hormone peptide. Bioconjug. Chem. 20, 2162-2168.

Hoffman, T. J., Gali, H., Smith, C. J., Sieckman, G. L., Hayes, D. L., Owen, N. K., and Volkert, W. A. (2003) Novel series of 111In-labeled bombesin analogs as potential radiopharmaceuticals for specific targeting of gastrin-releasing peptide receptors expressed on human prostate cancer cells. J. Nucl. Med. 44, 823-831.

* cited by examiner

SEQ ID NO: 7

SEQUENCE LISTING

```
<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: Native GnRH peptide
<220> FEATURE:
<221> NAME/KEY: misc_feature
<222> LOCATION: (1)
<223> OTHER INFORMATION: Xaa is pGlu

<400> SEQUENCE: 1

Xaa His Trp Ser Tyr Gly Leu Arg Pro Gly
1               5                   10

<210> SEQ ID NO 2
<211> LENGTH: 10
<212> TYPE: PRT
<213> ORGANISM: Artificial Sequence
<220> FEATURE:
<223> OTHER INFORMATION: 125I-[D-Trp]-LH-RH
<220> FEATURE:
<221> NAME/KEY: misc_feature
<222> LOCATION: (1)
<223> OTHER INFORMATION: Xaa is pGlu
<220> FEATURE:
<221> NAME/KEY: misc_feature
<222> LOCATION: (5)
<223> OTHER INFORMATION: Xaa is [125I]Tyr
<220> FEATURE:
<221> NAME/KEY: misc_feature
<222> LOCATION: (6)
<223> OTHER INFORMATION: Xaa is D-Trp
```

<400> SEQUENCE: 2

Xaa His Trp Ser Xaa Xaa Leu Arg Pro Gly
1               5                   10

<210> SEQ ID NO 3
<211> LENGTH: 5
<212> TYPE: PRT
<213> ORGANISM: Artificial Sequence
<220> FEATURE:
<223> OTHER INFORMATION: GnRH peptide
<220> FEATURE:
<221> NAME/KEY: misc_feature
<222> LOCATION: (1)
<223> OTHER INFORMATION: Xaa is Dde-HN-D-Lys(Ahx-DOTA(tBu)3)
<220> FEATURE:
<221> NAME/KEY: misc_feature
<222> LOCATION: (3)
<223> OTHER INFORMATION: Xaa is Arg(Pbf)

<400> SEQUENCE: 3

Xaa Leu Xaa Pro Gly
1               5

<210> SEQ ID NO 4
<211> LENGTH: 5
<212> TYPE: PRT
<213> ORGANISM: Artificial Sequence
<220> FEATURE:
<223> OTHER INFORMATION: GnRH peptide
<220> FEATURE:
<221> NAME/KEY: misc_feature
<222> LOCATION: (1)
<223> OTHER INFORMATION: Xaa is Lys(Dde)
<220> FEATURE:
<221> NAME/KEY: misc_feature
<222> LOCATION: (3)
<223> OTHER INFORMATION: Xaa is Arg(Pbf)

<400> SEQUENCE: 4

Xaa Leu Xaa Pro Gly
1               5

<210> SEQ ID NO 5
<211> LENGTH: 5
<212> TYPE: PRT
<213> ORGANISM: Artificial Sequence
<220> FEATURE:
<223> OTHER INFORMATION: GnRH peptide
<220> FEATURE:
<221> NAME/KEY: misc_feature
<222> LOCATION: (1)
<223> OTHER INFORMATION: Xaa is Dde-HN-Lys(Ahx-DOTA(tBu)3)
<220> FEATURE:
<221> NAME/KEY: misc_feature
<222> LOCATION: (3)
<223> OTHER INFORMATION: Xaa is Arg(Pbf)

<400> SEQUENCE: 5

Xaa Leu Xaa Pro Gly
1               5

<210> SEQ ID NO 6
<211> LENGTH: 5
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (1)

```
<223> OTHER INFORMATION: Xaa is pGlu
<220> FEATURE:
<221> NAME/KEY: misc_feature
<222> LOCATION: (2)
<223> OTHER INFORMATION: Xaa is His(Trt)
<220> FEATURE:
<221> NAME/KEY: misc_feature
<222> LOCATION: (3)
<223> OTHER INFORMATION: Xaa is Trp(Boc)
<220> FEATURE:
<221> NAME/KEY: misc_feature
<222> LOCATION: (4)
<223> OTHER INFORMATION: Xaa is Ser(tBu)
<220> FEATURE:
<221> NAME/KEY: misc_feature
<222> LOCATION: (5)
<223> OTHER INFORMATION: Xaa is Tyr(tBu)

<400> SEQUENCE: 6

Xaa Xaa Xaa Xaa Xaa
1               5

<210> SEQ ID NO 7
<211> LENGTH: 10
<212> TYPE: PRT
<213> ORGANISM: Artificial Sequence
<220> FEATURE:
<223> OTHER INFORMATION: GnRH peptide
<220> FEATURE:
<221> NAME/KEY: misc_feature
<222> LOCATION: (1)
<223> OTHER INFORMATION: Xaa is pGlu
<220> FEATURE:
<221> NAME/KEY: misc_feature
<222> LOCATION: (6)
<223> OTHER INFORMATION: Xaa is DOTA-Ahx-(D-Lys-GnRH1)

<400> SEQUENCE: 7

Xaa His Trp Ser Tyr Xaa Leu Arg Pro Gly
1               5                   10

<210> SEQ ID NO 8
<211> LENGTH: 5
<212> TYPE: PRT
<213> ORGANISM: Artificial Sequence
<220> FEATURE:
<223> OTHER INFORMATION: GnRH peptide
<220> FEATURE:
<221> NAME/KEY: misc_feature
<222> LOCATION: (1)
<223> OTHER INFORMATION: Xaa is (tBu)3DOTA-Ahx-D-Lys(Dds)
<220> FEATURE:
<221> NAME/KEY: misc_feature
<222> LOCATION: (3)
<223> OTHER INFORMATION: Xaa is Arg(Pbf)

<400> SEQUENCE: 8

Xaa Leu Xaa Pro Gly
1               5

<210> SEQ ID NO 9
<211> LENGTH: 10
<212> TYPE: PRT
<213> ORGANISM: Artificial Sequence
<220> FEATURE:
<223> OTHER INFORMATION: GnRH peptide
<220> FEATURE:
<221> NAME/KEY: misc_feature
<222> LOCATION: (1)
<223> OTHER INFORMATION: Xaa is pGlu
<220> FEATURE:
<221> NAME/KEY: misc_feature
<222> LOCATION: (6)
```

```
<223> OTHER INFORMATION: Xaa is DOTA-Ahx-(D-Lys-GnRH2)

<400> SEQUENCE: 9

Xaa His Trp Ser Tyr Xaa Leu Arg Pro Gly
1               5                   10

<210> SEQ ID NO 10
<211> LENGTH: 10
<212> TYPE: PRT
<213> ORGANISM: Artificial Sequence
<220> FEATURE:
<223> OTHER INFORMATION: GnRH peptide
<220> FEATURE:
<221> NAME/KEY: misc_feature
<222> LOCATION: (1)
<223> OTHER INFORMATION: Xaa is pGlu
<220> FEATURE:
<221> NAME/KEY: misc_feature
<222> LOCATION: (6)
<223> OTHER INFORMATION: Xaa is DOTA-Ahx-(L-Lys-GnRH3)

<400> SEQUENCE: 10

Xaa His Trp Ser Tyr Xaa Leu Arg Pro Glu
1               5                   10
```

GONADOTROPIN-RELEASING HORMONE RECEPTOR-TARGETING PEPTIDES AND THEIR USE TO TREAT AND DIAGNOSE CANCER

RELATED APPLICATIONS

This application claims the benefit of priority of U.S. provisional application Ser. No. 61/478,414, filed Apr. 22, 2011, entitled "Radiolabeled Peptides for Breast and Prostate Cancer Imaging and Therapy", said application being incorporated by reference in its entirety herein.

GOVERNMENT SUPPORT

The present invention was made with Government support under grant no. grant W81XWH-09-1-0105 from the Department of Defense (DOD), the NIH grant NM-INBRE P20RR016480 from the National Institutes of Health (NIH), and Oxnard Foundation Award. Consequently, the U.S. government has certain rights in the invention.

FIELD OF THE INVENTION

The present invention is directed to novel non-invasive diagnostic tools/compounds to image and treat cancers, especially, breast cancer, prostate cancer and melanoma, among others, including metastatic cancer. The present invention represents a clear advance in the art which presently relies on tissue biopsy for diagnoses of these cancers. The novel imaging probes are capable of detecting cancerous, as well as their metastatic spread in tissues. This represents a significant step forward in the diagnosis and treatment of breast and prostate cancer and a number of other cancers as described herein, including metastatic cancer, using non-invasive molecular imaging techniques. The novel probes of the present invention will also be useful to initiate therapy for breast and/or prostate cancer, among other cancers as well as monitor patients' response to chemotherapy treatments and other interventions or therapies used in the treatment of cancer, including breast cancer and/or prostate cancer, including metastatic cancer as otherwise described herein. Compounds according to the present invention may be used as diagnostic tools for cancer and a number of conditions and diseases states which occur secondary to cancer, as well as therapeutic agents for treating cancer and alleviating or inhibiting such conditions and disease states.

BACKGROUND OF THE INVENTION

Prostate cancer was the most commonly diagnosed cancer in males (217,730 new cases) and the second leading cause of cancer-related death among men (32,050 fatalities) in the United States in 2010.[1] Upon diagnosis by current detection regimens, about 30% of patients have metastases.[2,3] Approximately 50% of patients eventually develop metastases.[4] Survival times for patients with metastases are generally 2~3 years from the time when the metastases are diagnosed.[5] Unfortunately, current prostate cancer treatments (radical prostatectomy, chemotherapy, immunotherapy, hormonal therapy and radiation therapy) are far from satisfactory and no curative treatment exists for metastatic prostate cancer. Early diagnosis of prostate cancer is critical for appropriate treatment decisions and may provide the patients the best opportunities for cures or prolonged survivals.

Currently, prostate-specific antigen (PSA) test is the first-line clinical screening tool for prostate cancer. However, PSA test is lack of sensitivity and specificity since PSA is an organ-specific biomarker rather than a cancer-specific biomarker. Approximately 43% of patients with organ-confined prostate cancer do not have elevated PSA levels,[6] indicating the high percentage false-negative rate of the PSA test. On the other hand, benign prostatic hyperplasia (BPH), which is extremely common in men, commonly results in elevated PSA levels.[7] Hence, PSA test has 60-80% false-positive findings based on prostate biopsies.[8]

The clinical single photon emission computed tomography (SPECT) scan using $^{111}$In-capromab Pendetide (ProstaScint® Scan, Cyt-356) targeting the prostate-specific membrane antigen (PSMA) provides more accurate localization and staging of a new or recurrent prostate cancer than the PSA test.[9-12] However, relatively low sensitivity (62%) and overall accuracy (68%) of the ProstaScint scan limits its widespread application. At present, 2-[$^{18}$F]fluoro-2-deoxy-D-glucose ([$^{18}$F]FDG) is the most commonly used positron emission tomography (PET) imaging agent for the detection of various tumors including prostate cancer.[13-16] However, the delineation of prostate cancer by PET with [$^{18}$F]FDG is generally unsatisfactory due to the low uptake of [$^{18}$F]FDG in prostate cancer.[15,16] Relatively low sensitivity (60-70%) of [$^{18}$F]FDG PET is due to the fact that the glucose utilization is not significantly higher in prostate cancer cells than that in normal cells. The limited clinical application of ProstaScint® and [$^{18}$F]FDG underscores the urgent need for novel cancer-specific imaging probes for prostate cancer detection.

Over-expression of gonadotropin-releasing hormone (GnRH) receptors on prostate cancer cells and specimens, dramatic low level expression on healthy prostate cells and no expression on most normal tissue cells[17-25] highlights the potential of GnRH receptor as a distinct molecular target for developing novel prostate cancer-specific imaging probes. Nativ GnRH peptide is a peptide with 10 amino acids (pGlu$^1$-His$^2$-Trp$^3$-Ser$^4$-Tyr$^5$-Gly$^6$-Leu$^7$-Arg$^8$-Pro$^9$-Gly$^{10}$-NH$_2$ SEQ ID NO:1). Both pGlu$^1$-His$^2$-Trp$^3$ and Arg$^8$-Pro$^9$-Gly$^{10}$-NH$_2$ motifs are crucial for GnRH receptor binding.[26] A backbone metal cyclization between the N-terminus and C-terminus of the GnRH peptides dramatically decreased their GnRH receptor binding affinities,[27] confirming that both N-terminus and C-terminus need to be reserved for strong GnRH receptor binding. The replacement of Gly$^6$ with a D-amino acid enhanced the binding affinity and reduces the metabolic clearance of the peptide.[28]

Breast cancer is the most commonly diagnosed cancer and the second leading cause of cancer death in women in the United States. It was predicted that approximately 209,060 new cases would be diagnosed and 40,230 fatalities would occur in the US in 2010[1]. Unfortunately, no curative treatment exists for metastatic breast cancer. Early diagnosis of breast cancer followed by a prompt surgical removal provides patients the best opportunities for cures or prolonged survivals. Mammography is an effective diagnostic tool for primary breast cancer. However, it is less effective for women with breast implants, post-surgical recurrence, or for women under age fifty as the breast tissue tends to be more dense[2]. Meanwhile, the mammography can't detect distant breast cancer metastases. Single photon emission computed tomography (SPECT) and positron emission tomography (PET) techniques[3,4] are more attractive non-invasive imaging modalities for metastatic breast cancer detection due to their high sensitivities and spatial resolutions. At present, 2-[$^{18}$F]fluoro-2-deoxy-D-glucose ([$^{18}$F]FDG) is the most commonly used PET imaging agent for the detection of various tumors including breast cancer[5-15]. However, the clinical application of [$^{18}$F]FDG is limited[10] by its unsatisfactory sensitivity for small tumors <1 cm (57%) and for tumors in-situ (25%), and high false-positive results in the circumstance of inflammation. Hence, novel breast cancer-specific imaging probes are urgently needed to improve the detection accuracy for breast cancer.

As in the case of breast cancer, the over-expression of gonadotropin-releasing hormone (GnRH) receptors on the breast cancer cells[16-20] highlights the potential of GnRH receptor as a molecular target for developing breast cancer-specific imaging probes. Clinical studies shows that 52% of breast cancer specimens removed by surgical resection over-expressed GnRH receptors[19-20]. Native GnRH peptide is a hypothalamic decapeptide (pGlu$^1$-His$^2$-Trp$^3$-Ser$^4$-Tyr$^5$-Gly$^6$-Leu$^7$-Arg$^8$-Pro$^9$-Gly$^{10}$-NH$_2$ SEQ ID NO:1). Both motifs of pGlu$^1$-His$^2$-Trp$^3$ and Arg$^8$-Pro$^9$-Gly$^{10}$-NH$_2$ motifs are critical for GnRH. receptor binding.[26] The replacement of Gly$^6$ with a D-amino acid increases the binding affinity and decreased the metabolic clearance of the peptide[22]. The D-Lys$^6$-GnRH peptide has been used as a delivery vehicle to target the chemotherapy agent (2-pyrrolino-doxorubicin, AN201) to the GnRH receptors for breast cancer treatment[23-31]. The AN201 was coupled to the epsilon amino group of D-Lys$^6$ in D-Lys6-GnRH to generate a cytotoxic compound named AN207[23]. The receptor-targeting AN207 exhibited enhanced remarkable therapeutic efficacy and decreased toxicity compared to the parent chemotherapy agent AN201. A single treatment of AN207 (250 nmol/kg) resulted in 100% cure for the mice bearing MX-1 human mammary carcinomas (GnRH receptor-positive) without apparent toxicity[28]. These results on AN207 indicated that D-Lys6-GnRH could selectively bind the GnRH receptor to target the chemotherapy agent to breast cancer cells. The Present inventors have been interested in. developing radiolabeled GnRH peptides to target the GnRH receptors for cancer detection.[29] To that end, they provide the various aspects of the present invention.

BRIEF DESCRIPTION OF THE INVENTION

The present invention relates to compounds according to the general structure:

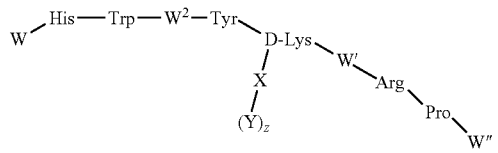

Where W is aspartic acid, glutamic acid or pyroglutamic acid (i.e., cyclized glutamic acid);

W$^2$ is serine or threonine, preferably serine;

W' is glycine, alanine, leucine, isoleucine or valine, preferably leucine or isoleucine, more preferably leucine;

W" is glycine or alanine, preferably glycine;

Y is a chelate group, wherein Y optionally incorporates or complexes with a radioisotope;

X is independently an amino acid linker according to the chemical structure:

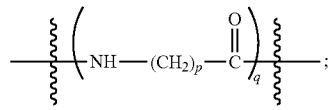

an alkylene oxide group (preferably a polyethylene, polypropylene or polyethylene-co-polypropylene group) according to the chemical structure:

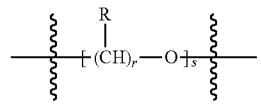

Where each R is independently H or a $C_1$-$C_3$ alkyl group (often H or a $CH_3$ group, more often R is H as in the case of an ethylene group or R is independently H or a $CH_3$ group as in the case of a propylene group), a $C_1$-$C_{25}$ hydrocarbon which is linear, branched or cyclic and may be fully saturated or contain one or more unsaturated carbon-carbon bonds (alkene and/or alkyne groups) or aromatic group (preferably a phenyl group), or an amino acid group from 1 to about 25 amino acid groups in length, wherein said amino acid groups are selected from the group consisting of glycine, alanine, leucine, isoleucine, valine, serine, threonine, phenylalanine, D-phenylalanine or a mixture thereof, preferably glycine, alanine, serine or mixtures thereof, preferably polyglycine, preferably polyglycine from about 3 to 8 glycine units in length, p is an integer from 0 to 25 preferably 0 to 12, preferably 2 to 8; preferably 4, 5 or 6;

q is an integer from 0 to 25, preferably 1 or 2 when p is 2 to 8, or preferably an integer from 5 to 25 when q is 1 or 2, preferably 1;

r is an integer from 2 to 6, preferably 2 or 3, preferably 2;

s is an integer from 1 to 25, preferably 1 to 12, 2 to 8, 4 to 6; and z is an integer from 0 to 5, preferably 1 to 5, preferably 1 or 2, more preferably 1, or a pharmaceutically acceptable salt thereof, and wherein said radioisotope, when complexed with said chelate group, is selected from the group consisting of $^{86}$Y, $^{90}$Y, $^{111}$In, $^{177}$Lu, $^{225}$Ac, $^{212}$Bi, $^{213}$Bi, $^{66}$Ga, $^{67}$Ga, $^{68}$Ga, $^{64}$Cu, $^{67}$Cu, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm, $^{153}$Sm, $^{201}$Tl, $^{188}$Re, $^{186}$Re and $^{99m}$Tc, preferably a polyvalent cationic radioisotope thereof. In preferred aspects of the invention, the radioisotope is $^{111}$In or $^{99m}$Tc.

In preferred aspects of the invention, the compound incorporates or is complexed with a radioisotope as otherwise described herein. In certain aspects of the invention, Y is a radical (i.e., linked to the peptide/amide linker X as described herein) of DOTA (1,4,7,10-tetraazacyclododecane-1,4,7,10-tetraacetic acid), CB-TE2A (4,11-bis(carboxymethyl)-1,4,8,11-tetraazabicyclo[6.6.2]hexadecane), NOTA (1,4,7-triazacyclononane-1,4,7-triacetic acid), DTPA (Diethylenetriaminopentaacetic acid), MAG$_3$ (Mercaptoacetyltriglycine), 4,5-bis(2-mercaptoacetamido)pentanoic acid or HYNIC (hydrazinonicotinamide/6-hydrazinopyridine-3-carboxylic acid, especially for $^{99m}$Tc and $^{186}$Re/$^{188}$Re radiolabeling), optionally in combination with tricine or EDDA as a coligand. Other chelating moieties that can complex to radioisotopes are as otherwise disclosed herein.

In preferred aspects of the invention, Y is a DOTA radical according to the chemical structure:

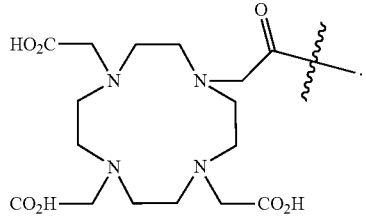 [SMILES: *C(=O)CN1CCN(CC(=O)O)CCN(CC(=O)O)CCN(CC(=O)O)CC1]

Y is preferably a radical of DOTA (1,4,7,10-tetraazacyclododecane-1,4,7,10-tetraacetic acid), CB-TE2A (4,11-bis(carboxymethyl)-1,4,8,11-tetraazabicyclo[6.6.2]hexadecane), NOTA (1,4,7-triazacyclononane-1,4,7-triacetic acid), especially for $^{64}Cu/^{67}Cu$ and $^{66}Ga/^{67}Ga/^{68}Ga$, DTPA (Diethylenetriaminepentaacetic acid), MAG$_3$ (Mercaptoacetyltriglycine) or 4,5-bis(2-mercaptoacetamido)pentanoic acid and HYNIC (hydrazinonicotinamide/6-hydrazinopyridine-3-carboxylic acid), alone or often using tricine (N-Tris(hydroxymethyl)methylglycine) as coligand. More preferably, Y is a radical of DOTA, optionally complexed with a radioisotope as otherwise described herein, preferably $^{111}$In or $^{99m}$Tc (as depicted for $^{111}$In in FIG. 1 hereof). In the case of $^{99m}$Tc and $^{186}Re/^{188}Re$ radiolabeling, the use of HYNIC alone or in combination with tricine or EDDA (ETHYLENEDIAMINEDIACETIC ACID) as coligand may be preferred. In the case of one or more of $^{64}Cu/^{67}Cu$ and $^{66}Ga/^{67}Ga/^{68}Ga$, the use of NOTA as a chelating moiety (radical) is preferred.

In preferred embodiments, the present invention relates to the above compounds, including pharmaceutically acceptable salts, wherein the compound, especially the Y group, is complexed with a radioisotope (which may be a neutral species or a cationic species, and is preferably a polyvalent cationic species) selected from the group consisting of $^{86}Y$, $^{90}Y$, $^{111}$In, $^{177}$Lu, $^{225}$Ac, $^{212}$Bi, $^{213}$Bi, $^{66}Ga$, $^{67}Ga$, $^{68}Ga$, $^{64}Cu$, $^{67}Cu$, $^{71}As$, $^{72}As$, $^{76}As$, $^{77}As$, $^{65}Zn$, $^{4}V$, $^{203}Pb$, $^{209}Pb$, $^{212}Pb$, $^{166}Ho$, $^{149}Pm$, $^{153}Sm$, $^{201}Tl$, $^{188}Re$, $^{186}Re$ and $^{99m}Tc$.

In further preferred embodiments, Y is a DOTA moiety which may be complexed with a radioisotope as indicated (this general structure also contemplates one or more carbonyl/carboxyl groups in the molecule also being complexed to the radioisotope as indicated in FIG. 1 hereof and is non-limiting) according to the following:

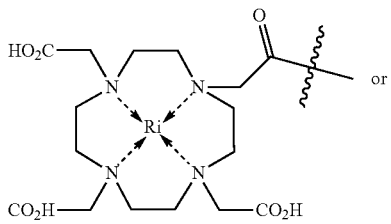 or

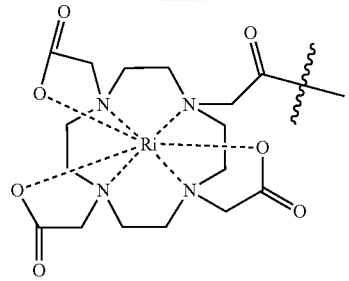

Where Ri is a radioisotope (which may be a neutral species or a cationic species, and is preferably a polyvalent cationic species) selected from the group consisting of $^{86}Y$, $^{90}Y$, $^{111}$In, $^{177}$Lu, $^{225}$Ac, $^{212}$Bi, $^{213}$Bi, $^{66}Ga$, $^{67}Ga$, $^{68}Ga$, $^{64}Cu$, $^{67}Cu$, $^{71}As$, $^{72}As$, $^{76}As$, $^{65}Zn$, $^{48}V$, $^{203}Pb$, $^{209}Pb$, $^{212}Pb$, $^{166}Ho$, $^{149}Pm$, $^{153}Sm$, $^{201}Tl$, $^{188}Re$, $^{186}Re$ and $^{99m}Tc$. Preferably, the radioisotope is $^{111}$In or $^{99m}$Tc.

Radioisotopes are selected based on the physical half life, the decay mode (alpha, beta, auger, gamma, X-ray) and the energy of the radioisotope. In diagnostic aspects of the present invention, preferred radioisotopes include, for example, $^{111}$In, $^{86}Y$, $^{66}Ga$, $^{67}Ga$, $^{68}Ga$, $^{203}Pb$, $^{64}Cu$ and $^{99m}Tc$. Preferably, the radioisotope is $^{111}$In or $^{99m}$Tc.

Where compounds are to be analyzed using positron emission tomography or PET imaging they are labeled with a positron emitting radioisotopes such as: $^{66}Ga$, $^{68}Ga$, $^{64}Cu$, $^{86}Y$, or other polyvalent, cationic radiometals that decay by positron emission. In alternative embodiments, the compounds may be analyzed using single photon emission computed tomography or SPECT imaging when labeled with a gamma radiation emitting radioisotope which preferably includes $^{111}$In, $^{67}Ga$, $^{99m}$Tc and $^{203}Pb$ or other gamma emitting radioisotope as disclosed herein.

The present invention relates to compounds and/or compositions which may be used to prepare imaging/therapeutic agents or as imaging/therapeutic agents (when complexed with a radioisotope) for diagnosing and treating a cancer in a tissue which overexpresses gonadotropin-release hormone (GnRH) especially including prostate cancer, breast cancer, ovarian cancer, cervical cancer, placental cancer, melanoma, colon cancer, glioblastoma, neuroblastoma, lung, including non-small cell lung cancer, kidney (hepatocellular), lymphoma, leukemia, among others, as well as cancers which have metastasized from those cancers, among others. Compounds according to the present invention which are complexed with an appropriate radioisotope may be used to diagnose the existence and/or extent of cancer as described herein (including prostate cancer, breast cancer, ovarian cancer, cervical cancer, placental cancer, melanoma, colon cancer, glioblastoma, neuroblastoma, lung, including non-small cell lung cancer, kidney (hepatocellular), lymphoma, leukemia, among others as well as cancers which have metastasized from those cancers), monitor therapy as a therapeutic aid of cancer (e.g., prostate cancer, breast cancer, ovarian cancer, cervical cancer and melanoma, among others, including metastatic cancer), and in certain instances, function as a therapeutic agent (peptide targeted radiation) for the treatment of cancer, including metastatic cancer.

The present invention also relates to pharmaceutical compositions comprising an effective amount of a compound according to the present invention which has been complexed with a radioisotope and combined with a carrier, additive or excipient in pharmaceutical dosage form as a diagnostic imaging agent or as a therapeutic agent. Compositions according to the present invention are formulated in pharmaceutical dosage form for administration preferably by a parenteral, preferably an intravenous route. Compositions according to the present invention may also be formulated for administration via a topical route, directly to the skin. Oral compositions may also be formulated for use in the present invention.

In the diagnostic method according to the present invention, a compound according to the present invention is administered to a patient, and evidence of elevated expression of GnRH receptors in tissue of said patient through standard well-known nuclear imaging techniques, especially radiation (radionuclide) imaging, including scintigraphic imaging, and especially single photon emission computed tomography (SPECT) and positron emission tomography (PET) in comparison to a normal standard, is indicative of a disease state (cancer as otherwise described herein) and extent of disease state (metastasis) in the tissue of the patient. The nuclear imaging techniques useful in the present diagnostic methods are well known in the art. In general, elevated levels of radiation emanating from a diagnosed tissue is evidence of elevated GnRH receptor activity and indicative of a disease state or condition (cancer and/or metastatic cancer) wherein these receptors are found at elevated levels. Methods of diagnosing the existence and/or extent (stage) of cancer, including metastatic cancer are therefore additional aspects of the present invention. Thus, a diagnostic method of diagnosing the existence or absence of the overexpresson of GnRH, and therefore, cancer (e.g., prostate cancer, breast cancer, ovarian cancer, cervical cancer, placental cancer, melanoma, colon cancer, glioblastoma, neuroblastoma, lung, including non-small cell lung cancer, kidney (hepatocellular), lymphoma, leukemia, among others, as well as cancers which have metastasized from those cancers), in a patient at risk for cancer comprises administering to said patient a compound according to the present invention; imaging said patient to determine if tissue in said patient exhibits elevated expression of GnRH receptors; and diagnosing said patient as having cancer, including metastatic cancer if said tissue evidences elevated expression of GnRH receptors in comparison to a standard.

Methods of monitoring the treatment of cancer (e.g. prostate cancer, breast cancer, ovarian cancer, cervical cancer, placental cancer, melanoma, colon cancer, glioblastoma, neuroblastoma, lung, including non-small cell lung cancer, kidney (hepatocellular), lymphoma, leukemia, as well as cancers which have metastasized from those cancers), including metastatic cancer in conjunction with traditional or experimental cancer therapy is an additional aspect of the invention. In this aspect, a patient's response to therapy is monitored using the methods according to the present invention. In this method, a patient is monitored before and after therapy by administering compound according to the present invention and determining (through imaging diagnostics as otherwise described herein) the extent of expression of gonadotropin-releasing hormone (GnRH) receptors in tissues of a patient before therapy and after therapy and comparing the expression levels with each other and/or with a standard (predetermined value) to determine the extent of reduction of cancer tissue which occurred pursuant to the therapeutic intervention.

Methods of treating cancer (e.g. prostate cancer, breast cancer, ovarian cancer, cervical cancer, placental cancer, melanoma, colon cancer, glioblastoma, neuroblastoma, lung, including non-small cell lung cancer, kidney (hepatocellular), lymphoma, leukemia, as well as cancers which have metastasized from those cancers), represent a further aspect of the invention. In this aspect, compounds according to the present invention as described above are administered to a patient known to have cancer (e.g., prostate cancer, breast cancer, ovarian cancer, cervical cancer, placental cancer, melanoma, colon cancer, glioblastoma, neuroblastoma, lung, including non-small cell lung cancer, kidney (hepatocellular), lymphoma, leukemia, as well as cancers which have metastasized from those cancers), and/or metastatic cancer in effective amounts in order to reduce cancer tissue and otherwise treat the patient's cancer through targeted radiation therapy. The present therapeutic methods may be used alone or in combination with other treatment methods (surgery, chemotherapy, radiation therapy and/or immunotherapy (IL-2 and α-interferon) for cancer/metastatic cancer as otherwise disclosed herein. In preferred therapeutic method aspects of the present invention, compounds according to the present invention are labeled with $^{90}Y$, $^{177}Lu$, $^{186}Re$, $^{188}Re$, $^{212}Bi/^{212}Pb$, $^{213}Bi$, $^{149}Pm$, $^{166}Ho$ and $^{153}Sm$ and are administered to the patient (preferably intravenously or topically—i.e, directly onto or into the cancer tissue in the relevant tissue of the patient) in order to target the malignant tumor, including metastatic cancer tissue with radiation therapy.

DETAILED DESCRIPTION OF THE INVENTION

Figure 1:
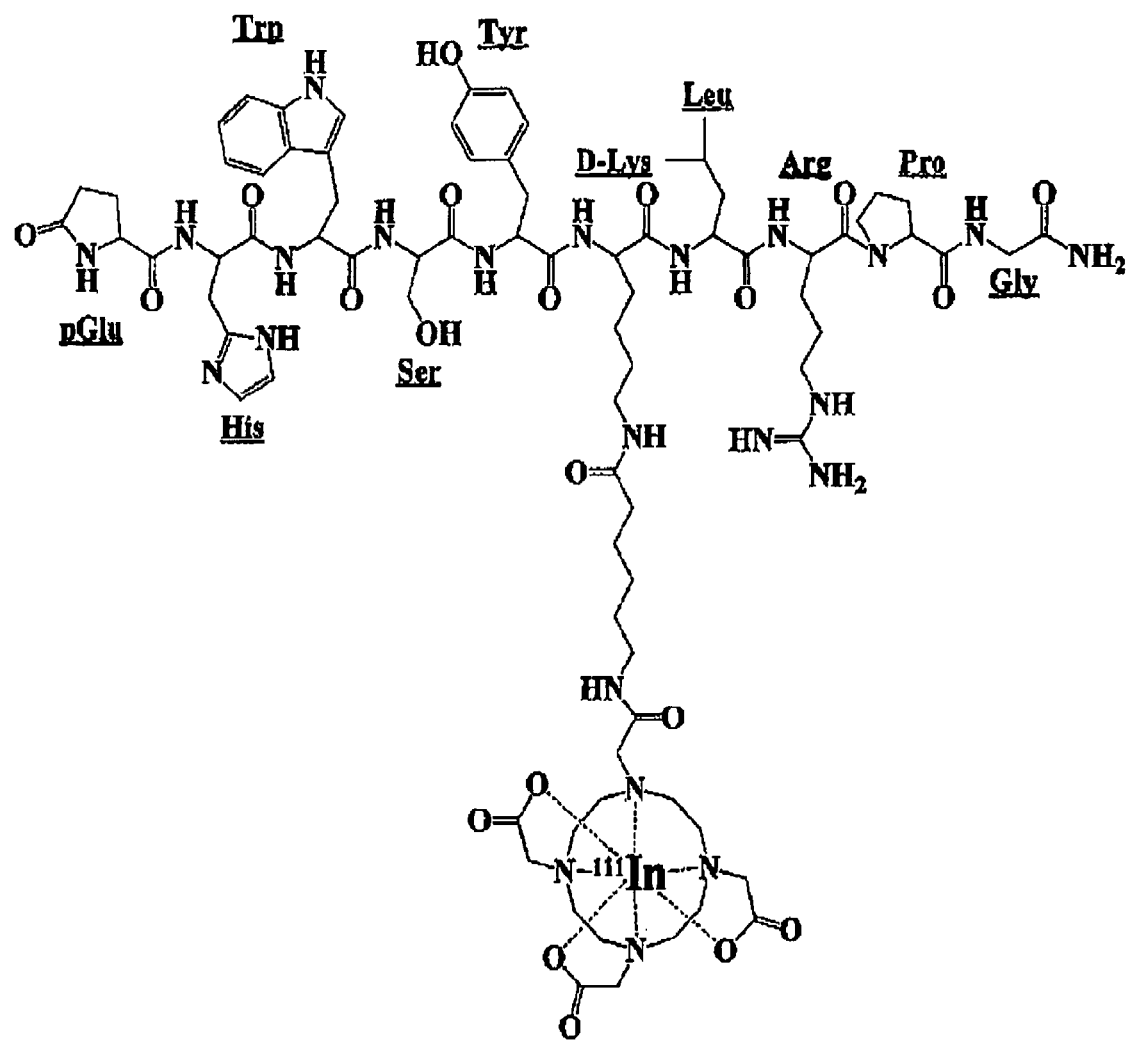
FIG. 1 shows the structure of $^{111}In$-DOTA-Ahx-(D-Lys$^6$-GnRH1).

The following terms are used to describe the present invention. In the event that a term is not specifically defined herein, that term is accorded its commonly understood meaning within the context of its use by those of ordinary skill in the art. It is understood that the definitions of the terms which are used to describe the present invention are interpreted in a manner consistent with the present invention and within the context of a particular term's use in describing the present invention in one or more embodiments.

As used herein and in the appended claims, the singular forms "a," "an," and "the" include plural reference unless the context clearly dictates otherwise. Thus, for example, a reference to "a compound", within context, includes a plurality (for example, two or more compounds) of such elements, and so forth. Under no circumstances is the patent be interpreted to be limited to the specific examples or embodiments or methods specifically disclosed herein.

The term "patient" or "subject" is used throughout the specification to describe an animal, including a domestic animal such as a dog, cat, cow, pig, sheep, among others, preferably a human, to whom treatment, including prophylactic treatment, with the compounds according to the present invention is provided. For treatment of those cancers, conditions or disease states which are specific for a specific animal such as a human patient, the term patient refers to that specific animal.

The term "compound" is used herein to refer to any specific chemical compound disclosed herein. Within its use in context, the term generally refers to a single oligopeptide, or an oligopeptide bonded to a chelator group such as a DOTA group or as otherwise described herein, optionally complexed with a radioisotope, but in certain instances may also refer to components/portions of such compounds, intermediates used to synthesize such compounds, stereoisomers and/or optical isomers (including racemic mixtures) of disclosed compounds. The term compound shall include, where applicable, any and all relevant pharmaceutically acceptable salts thereof.

The term "chelate", "chelator" or "chelating agent" is used to describe a moiety (as represented by Y in the generic structures of compounds according to the present invention) which is functionally capable of complexing or "chelating" a radioisotope as otherwise described herein, preferably $^{111}$In or $^{99m}$Tc, among others. Each is appropriately chemically linked (via covalent linkers or directly to the oligo peptides as otherwise described herein). Exemplary chelators for use in the present invention, which are well known in the art, include the following:

Polyaminocarboxylates, Such as
EDTA: ethylenediaminetetraacetic acid
DTPA: diethylenetriaminepentaacetic acid Polyaminocarboxylic Macrocycles, Such as:
DOTA: 1,4,7,10-tetraazacyclododecane-1,4,7,10-tetraacetic acid
TRITA: 1,4,7,10-tetraazacyclotridecane-1,4,7,10-tetraacetic acid
TETA: triethylenetetramine bridged-cyclam-2a: 1,4,8,11-tetraazabicyclo[6.6.2]hexadecane-1,8-di(methanephosphonic acid)
DO3A: 1,4,7-tris(carboxymethyl)-1,4,7,10-tetraazacyclododecane
DO2A: 1,4,7,10-tetraazacyclododecane-1,7-bis(acetic acid)

Other Chelators, Such as:
CB-TE2A (4,11-bis(carboxymethyl)-1,4,8,11-tetraazabicyclo[6.6.2]hexadecane) NOTA (1,4,7-triazacyclononane-1,4,7-triacetic acid)
MAG$_3$ (Mercaptoacetyltriglycine)
4,5-bis(2-mercaptoacetamido)pentanoic acid
HYNIC (hydrazinonicotinamide/6-hydrazinopyridine-3-carboxylic acid)

Chelates, chelators or chelating agents are generally bi- or multidentate ligands which generally produce a binding or complexation (complex) of a metal radioisotope as otherwise described herein. The ligand or chelator forms a chelate complex with the substrate. The term, without limitation, is used to describe complexes in which the metal ion is bound to two or more atoms of the chelating agent by whatever means (e.g., coordinate binding or complexation) occurs when a radioisotope and chelate group complex within each other in compounds according to the present invention. It is noted here that when a chelator is complexed to a radioisotope as used herein, the chelate complex structure is represented in a generic, nonlimiting sense, such that bonds which are represented may occur between a radioistope and the chelating agent, as well as additional bonds (such as between carbonyl/carboxyl groups) which are not specifically represented, but which are understood/determined to be bonded within the context of the chelate complex (to accommodate that different radioisotopes may bind differently to different chelate groups).

The term "DOTA" is used as an abbreviation for 1,4,7,10-tetraazacyclododecane-1,4,7,10-tetraacetic acid, a preferred chelator for use in the present invention, which chemical structure (bonded in compounds according to the present invention) is represented as follows:

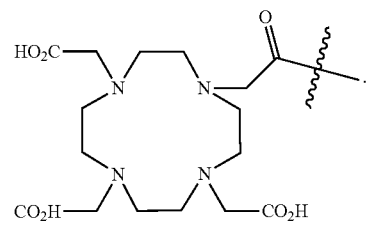

Complexed with radioisotopes according to the present invention, DOTA has the general (note that this general structure also includes the possibility of carbonyl/carboxyl groups also contributing to the complex depending on the radioisotope and is non-limiting) structure:

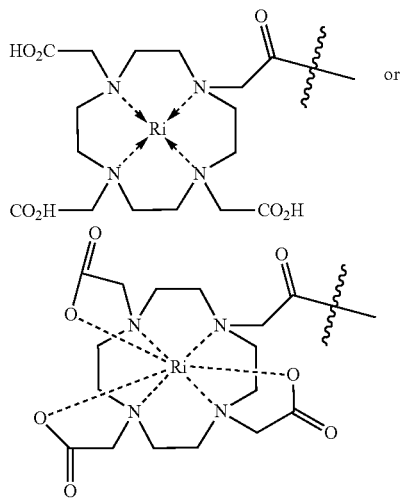

Where Ri is a radioisotope as otherwise disclosed herein.

In certain alternative embodiments, the chelator group is a NOTA (1,4,7-triazacyclononane-1,4,7-triacetic acid) group especially for $^{64}$Cu, $^{67}$Cu, $^{66}$Ga, $^{67}$Ga, $^{68}$Ga or mixtures thereof or a HYNIC (hydrazinonicotinamide/6-hydrazinopyridine-3-carboxylic acid) group, alone or in combination with tricine or EDDA (ETHYLENEDIAMINEDIACETIC ACID) for $^{99m}$Tc and $^{186}$Re/$^{188}$Re.

The term "GnRH peptide" or "GnRH oligopeptide" refers to peptides which are bound optionally through a peptide linker as otherwise described herein to the chelate, preferably DOTA according to the present invention. GnRH peptides according to the present invention may be represented by the chemical structure

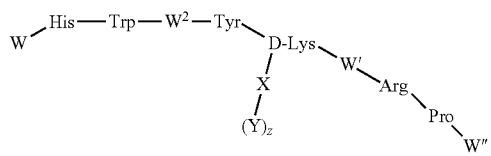

Where W is aspartic acid, glutamic acid or pyroglutamic acid (i.e., cyclized glutamic acid);

$W^2$ is serine or threonine, preferably serine;

W' is glycine, alanine, leucine, isoleucine or valine, preferably leucine or isoleucine, more preferably leucine;

W" is glycine or alanine, preferably glycine;

Y is a chelate group, wherein Y optionally incorporates or complexes with a radioisotope;

X is independently an amino acid linker according to the chemical structure:

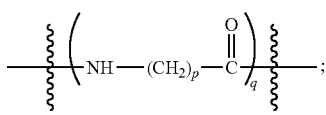

an alkylene oxide group (preferably a polyethylene, polypropylene or polyethylene-co-polypropylene group) according to the chemical structure:

$$\{(CH)_r-O\}_s$$

Where each R is independently H or a $C_1$-$C_3$ alkyl group (often H or a $CH_3$ group, more often R is H as in the case of an ethylene group or R is independently H or a $CH_3$ group as in the case of a propylene group), a $C_1$-$C_{25}$ hydrocarbon which is linear, branched or cyclic and may be fully saturated or contain one or more unsaturated carbon-carbon bonds (alkene and/or alkyne groups) or aromatic group (preferably a phenyl group), or an amino acid group from 1 to about 25 amino acid groups in length, wherein said amino acid groups are selected from the group consisting of glycine, alanine, leucine, isoleucine, valine, serine, threonine, phenylalanine, D-phenylalanine or a mixture thereof, preferably glycine, alanine, serine or mixtures thereof, preferably polyglycine, preferably polyglycine from about 3 to 8 glycine units in length, p is an integer from 0 to 25 preferably 0 to 12, preferably 2 to 8; preferably 4, 5 or 6;

q is an integer from 0 to 25, preferably 1 or 2 when p is 2 to 8, or preferably an integer from 5 to 25 when p is 1 or 2, preferably 1;

r is an integer from 2 to 6, preferably 2 or 3, preferably 2;

s is an integer from 1 to 25, preferably 1 to 12, 2 to 8, 4 to 6; and z is an integer from 0 to 5, preferably 1 to 5, preferably 1 or 2, more preferably 1, or a pharmaceutically acceptable salt thereof, and wherein said radioisotope, when complexed with said chelate group, is selected from the group consisting of $^{86}$Y, $^{90}$Y, $^{111}$In, $^{177}$Lu, $^{225}$Ac, $^{212}$Bi, $^{213}$Bi, $^{66}$Ga, $^{67}$Ga, $^{68}$Ga, $^{64}$Cu, $^{67}$Cu, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm, $^{152}$Sm, $^{201}$Tl, $^{88}$Re, $^{186}$Re and $^{99m}$Tc, preferably a polyvalent cationic radioisotope thereof. In preferred aspects of the invention, the radioisotope is $^{111}$In.

In preferred aspects of the present invention, the GnRH peptide is by the following chemical structure:

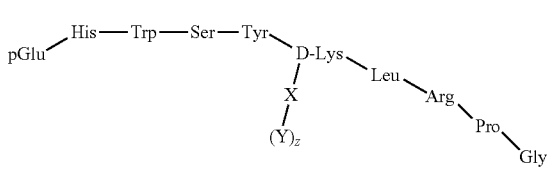

Where Y is preferably a DOTA chelate group, z is 1 to 5, preferably 1 or 2, and X is an amino acid residue or an amino acid linker according to the chemical structure:

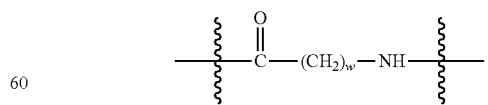

or a polyglycine group having between 3 and 6 glycine groups within the polyglycine chain; and w is an integer from 0 to 25, preferably 1 to 12, preferably 2 to 8 or 4 to 6; or a pharmaceutically acceptable salt thereof, which is complexed with a radioisotope as otherwise described herein. Preferably, the radioisotope is $^{111}$In.

The term "radical" is used to describe a group which is covalently bonded to another group in compounds according to the present invention.

The term "tumor" is used to describe a malignant or benign growth or tumefacent.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors.

Any cancer or tumor in a tissue which overexpresses gonadotropin-releasing hormone (GnRH) is a target for compounds, pharmaceutical compositions and therapy according to the present invention. Among the tissues which evidence the existence of an overexpression of GnRH which is consistent with the existence and diagnosis of cancer include inter alia prostate cancer, breast cancer, ovarian cancer, cervical cancer, placental cancer, melanoma, colon cancer, glioblastoma, neuroblastoma, lung, including non-small cell lung cancer, kidney (hepatocellular), lymphoma, and leukemia, among others, as well as cancers which have metastasized from those cancers, which emanates from these tissues and cancer residing therein.

Representative cancers include, for example, prostate cancer, breast cancer, ovarian cancer, cervical cancer, uterine cancer, placental cancer melanoma, stomach, colon, rectal, liver, pancreatic, lung, uteri, testis, bladder, renal, brain/CNS, head and neck, throat, Hodgkin's disease, non-Hodgkin's lymphoma, multiple myeloma, leukemia, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention. Because of the activity of the present compounds as modulators, especially inhibitors of gonadotropin-releasing hormone receptors, the present invention has general applicability treating virtually any cancer in any tissue which overexpresses gonadotropin-releasing hormone receptors, thus the compounds, compositions and methods of the present invention are generally applicable to the treatment of cancer.

In certain particular aspects of the present invention, the cancer which is treated is prostate cancer, metastatic prostate cancer, breast cancer or metastatic breast cancer, although virtually any cancer, as described above, may be diagnosed and/or treated using compounds, compositions and methods according to the present invention. Separately, metastatic prostate cancer and metastatic breast cancer may be found in virtually all tissues of a cancer patient in late stages of the disease, typically metastatic prostate cancer is found in seminal vesicles, lymph system/nodes (lymphoma), in bones, in bladder tissue, in kidney tissue, liver tissue and in virtually any tissue, including brain (brain cancer/tumor). Thus, the present invention is generally applicable and may be used to treat any cancer in any tissue, regardless of etiology, provided that the cancer tissue expresses sufficient gonadotropin-releasing hormone receptors (determined diagnostically using compounds according to the present invention) for the present compounds to have an effect.

The term "prostate cancer" is used to describe a disease in which cancer develops in the prostate, a gland in the male reproductive system. It occurs when cells of the prostate mutate and begin to multiply uncontrollably. These cells may metastasize (metastatic prostate cancer) from the prostate to virtually any other part of the body, particularly the bones and lymph nodes, but the kidney, bladder and even the brain, among other tissues. Prostate cancer may cause pain, difficulty in urinating, problems during sexual intercourse, erectile dysfunction. Other symptoms can potentially develop during later stages of the disease.

Rates of detection of prostate cancers vary widely across the world, with South and East Asia detecting less frequently than in Europe, and especially the United States. Prostate cancer develops most frequently in men over the age of fifty and is one of the most prevalent types of cancer in men. However, many men who develop prostate cancer never have symptoms, undergo no therapy, and eventually die of other causes. This is because cancer of the prostate is, in most cases, slow-growing, and because most of those affected are over the age of 60. Hence, they often die of causes unrelated to the prostate cancer. Many factors, including genetics and diet, have been implicated in the development of prostate cancer. The presence of prostate cancer may be indicated by symptoms, physical examination, prostate specific antigen (PSA), or biopsy. There is concern about the accuracy of the PSA test and its usefulness in screening. Suspected prostate cancer is typically confirmed by taking a biopsy of the prostate and examining it under a microscope. Further tests, such as CT scans and bone scans, may be performed to determine whether prostate cancer has spread.

Treatment options for prostate cancer with intent to cure are primarily surgery and radiation therapy. Other treatments such as hormonal therapy, chemotherapy, proton therapy, cryosurgery, high intensity focused ultrasound (HIFU) also exist depending on the clinical scenario and desired outcome.

The age and underlying health of the man, the extent of metastasis, appearance under the microscope, and response of the cancer to initial treatment are important in determining the outcome of the disease. The decision whether or not to treat localized prostate cancer (a tumor that is contained within the prostate) with curative intent is a patient trade-off between the expected beneficial and harmful effects in terms of patient survival and quality of life.

An important part of evaluating prostate cancer is determining the stage, or how far the cancer has spread. Knowing the stage helps define prognosis and is useful when selecting therapies. The most common system is the four-stage TNM system (abbreviated from Tumor/Nodes/Metastases). Its components include the size of the tumor, the number of involved lymph nodes, and the presence of any other metastases.

The most important distinction made by any staging system is whether or not the cancer is still confined to the prostate or is metastatic. In the TNM system, clinical T1 and T2 cancers are found only in the prostate, while T3 and T4 cancers have spread elsewhere and metastasized into other tissue. Several tests can be used to look for evidence of spread. These include computed tomography to evaluate spread within the pelvis, bone scans to look for spread to the bones, and endorectal coil magnetic resonance imaging to closely evaluate the prostatic capsule and the seminal vesicles. Bone scans often reveal osteoblastic appearance due to increased bone density in the areas of bone metastasis—opposite to what is found in many other cancers that metastasize. Computed tomography (CT) and magnetic resonance imaging (MRI) currently do not add any significant information in the assessment of possible lymph node metastases in patients with prostate cancer according to a meta-analysis.

Prostate cancer is relatively easy to treat if found early. After a prostate biopsy, a pathologist looks at the samples under a microscope. If cancer is present, the pathologist reports the grade of the tumor. The grade tells how much the tumor tissue differs from normal prostate tissue and suggests how fast the tumor is likely to grow. The Gleason system is used to grade prostate tumors from 2 to 10, where a Gleason score of 10 indicates the most abnormalities. The pathologist assigns a number from 1 to 5 for the most common pattern observed under the microscope, then does the same for the second most common pattern. The sum of these two numbers is the Gleason score. The Whitmore-Jewett stage is another method sometimes used. Proper grading of the tumor is critical, since the grade of the tumor is one of the major factors used to determine the treatment recommendation.

Early prostate cancer usually causes no symptoms. Often it is diagnosed during the workup for an elevated PSA noticed during a routine checkup. Sometimes, however, prostate cancer does cause symptoms, often similar to those of diseases such as benign prostatic hypertrophy. These include frequent urination, increased urination at night, difficulty starting and maintaining a steady stream of urine, blood in the urine, and painful urination. Prostate cancer is associated with urinary dysfunction as the prostate gland surrounds the prostatic urethra. Changes within the gland therefore directly affect urinary function. Because the vas deferens deposits seminal fluid into the prostatic urethra, and secretions from the prostate gland itself are included in semen content, prostate cancer may also cause problems with sexual function and performance, such as difficulty achieving erection or painful ejaculation.

Advanced prostate cancer can spread to other parts of the body and this may cause additional symptoms. The most common symptom is bone pain, often in the vertebrae (bones of the spine), pelvis or ribs. Spread of cancer into other bones such as the femur is usually to the proximal part of the bone. Prostate cancer in the spine can also compress the spinal cord, causing leg weakness and urinary and fecal incontinence.

The specific causes of prostate cancer remain unknown. A man's risk of developing prostate cancer is related to his age, genetics, race, diet, lifestyle, medications, and other factors. The primary risk factor is age. Prostate cancer is uncommon in men less than 45, but becomes more common with advancing age. The average age at the time of diagnosis is 70. However, many men never know they have prostate cancer.

A man's genetic background contributes to his risk of developing prostate cancer. This is suggested by an increased incidence of prostate cancer found in certain racial groups, in identical twins of men with prostate cancer, and in men with certain genes. Men who have a brother or father with prostate cancer have twice the usual risk of developing prostate cancer. Studies of twins in Scandinavia suggest that forty percent of prostate cancer risk can be explained by inherited factors. However, no single gene is responsible for prostate cancer; many different genes have been implicated. Two genes (BRCA1 and BRCA2) that are important risk factors for ovarian cancer and breast cancer in women have also been implicated in prostate cancer.

Dietary amounts of certain foods, vitamins, and minerals can contribute to prostate cancer risk. Dietary factors that may increase prostate cancer risk include low intake of vitamin E, the mineral selenium, green tea and vitamin D. A large study has implicated dairy, specifically low-fat milk and other dairy products to which vitamin A palmitate has been added. This form of synthetic vitamin A has been linked to prostate cancer because it reacts with zinc and protein to form an unabsorbable complex. Prostate cancer has also been linked to the inclusion of bovine somatotropin hormone in certain dairy products.

There are also some links between prostate cancer and medications, medical procedures, and medical conditions. Daily use of anti-inflammatory medicines such as aspirin, ibuprofen, or naproxen may decrease prostate cancer risk. Use of the cholesterol-lowering drugs known as the statins may also decrease prostate cancer risk. Infection or inflammation of the prostate (prostatitis) may increase the chance for prostate cancer, and infection with the sexually transmitted infections chlamydia, gonorrhea, or syphilis seems to increase risk. Obesity and elevated blood levels of testosterone may increase the risk for prostate cancer.

Prostate cancer is classified as an adenocarcinoma, or glandular cancer, that begins when normal semen-secreting prostate gland cells mutate into cancer cells. The region of prostate gland where the adenocarcinoma is most common is the peripheral zone. Initially, small clumps of cancer cells remain confined to otherwise normal prostate glands, a condition known as carcinoma in situ or prostatic intraepithelial neoplasia (PIN). Although there is no proof that PIN is a cancer precursor, it is closely associated with cancer. Over time these cancer cells begin to multiply and spread to the surrounding prostate tissue (the stroma) forming a tumor. Eventually, the tumor may grow large enough to invade nearby organs such as the seminal vesicles or the rectum, or the tumor cells may develop the ability to travel in the bloodstream and lymphatic system. Prostate cancer is considered a malignant tumor because it is a mass of cells which can invade other parts of the body. This invasion of other organs is called metastasis. Prostate cancer most commonly metastasizes to the bones, lymph nodes, rectum, and bladder.

In prostate cancer, the regular glands of the normal prostate are replaced by irregular glands and clumps of cells. When a man has symptoms of prostate cancer, or a screening test indicates an increased risk for cancer, more invasive evaluation is offered. The only test which can fully confirm the diagnosis of prostate cancer is a biopsy, the removal of small pieces of the prostate for microscopic examination. However, prior to a biopsy, several other tools may be used to gather more information about the prostate and the urinary tract. Cystoscopy shows the urinary tract from inside the bladder, using a thin, flexible camera tube inserted down the urethra. Transrectal ultrasonography creates a picture of the prostate using sound waves from a probe in the rectum.

After biopsy, the tissue samples are then examined under a microscope to determine whether cancer cells are present, and to evaluate the microscopic features (or Gleason score) of any cancer found. In addition, tissue samples may be stained for the presence of PSA and other tumor markers in order to determine the origin of maligant cells that have metastasized. A number of other potential approaches for diagnosis of prostate cancer are ongoing such as early prostate cancer antigen-2 (EPCA-2), and prostasome analysis.

In addition to therapy using the compounds according to the present invention, therapy (including prophylactic therapy) for prostate cancer supports roles in reducing prostate cancer for dietary selenium, vitamin E, lycopene, soy foods, vitamin D, green tea, omega-3 fatty acids and phytoestrogens. The selective estrogen receptor modulator drug toremifene has shown promise in early trials. Two medications which block the conversion of testosterone to dihydrotestosterone (and reduce the tendency toward cell growth), finasteride and dutasteride, are shown to be useful. The phytochemicals indole-3-carbinol and diindolylmethane, found in cruciferous vegetables (califlower and broccholi), have favorable antiandrogenic and immune modulating properties. Prostate cancer risk is decreased in a vegetarian diet.

Treatment for prostate cancer may involve active surveillance, surgery (prostatecomy or orchiectomy), radiation therapy including brachytherapy (prostate brachytherapy) and external beam radiation as well as hormonal therapy. There are several forms of hormonal therapy which include the following, each of which may be combined with compounds according to the present invention.

Antiandrogens such as flutamide, bicalutamide, nilutamide, and cyproterone acetate which directly block the actions of testosterone and DHT within prostate cancer cells.

Medications such as ketoconazole and aminoglutethimide which block the production of adrenal androgens such as DHEA. These medications are generally used only in combination with other methods that can block the 95% of androgens made by the testicles. These combined methods are called total androgen blockade (TAB), which can also be achieved using antiandrogens.

GnRH modulators, including agonists and antagonists. GnRH antagonists suppress the production of LH directly, while GnRH agonists suppress LH through the process of downregulation after an initial stimulation effect. Abarelix is an example of a GnRH antagonist, while the GnRH agonists include leuprolide, goserelin, triptorelin, and buserelin.

The use of abiraterone acetate can be used to reduce PSA levels and tumor sizes in aggressive end-stage prostate cancer for as high as 70% of patients. Sorafenib may also be used to treat metastatic prostate cancer.

Each treatment described above has disadvantages which limit its use in certain circumstances. GnRH agonists eventually cause the same side effects as orchiectomy but may cause worse symptoms at the beginning of treatment. When GnRH agonists are first used, testosterone surges can lead to increased bone pain from metastatic cancer, so antiandrogens or abarelix are often added to blunt these side effects. Estrogens are not commonly used because they increase the risk for cardiovascular disease and blood clots. The antiandrogens do not generally cause impotence and usually cause less loss of bone and muscle mass. Ketoconazole can cause liver damage with prolonged use, and aminoglutethimide can cause skin rashes.

Palliative care for advanced stage prostate cancer focuses on extending life and relieving the symptoms of metastatic disease. As noted above, abiraterone acetate shows some promise in treating advance stage prostate cancer as does sorafenib. Chemotherapy may be offered to slow disease progression and postpone symptoms. The most commonly used regimen combines the chemotherapeutic drug docetaxel with a corticosteroid such as prednisone. Bisphosphonates such as zoledronic acid have been shown to delay skeletal complications such as fractures or the need for radiation therapy in patients with hormone-refractory metastatic prostate cancer. Alpharadin may be used to target bone metastasis. The phase II testing shows prolonged patient survival times, reduced pain and improved quality of life.

Bone pain due to metastatic disease is treated with opioid pain relievers such as morphine and oxycodone. External beam radiation therapy directed at bone metastases may provide pain relief. Injections of certain radioisotopes, such as strontium-89, phosphorus-32, or samarium-153, also target bone metastases and may help relieve pain.

As an alternative to active surveillance or definitive treatments, alternative therapies may also be used for the management of prostate cancer. PSA has been shown to be lowered in men with apparent localized prostate cancer using a vegan diet (fish allowed), regular exercise, and stress reduction. Many other single agents have been shown to reduce PSA, slow PSA doubling times, or have similar effects on secondary markers in men with localized cancer in short term trials, such as pomegranate juice or genistein, an isoflavone found in various legumes.

Manifestations or secondary conditions or effects of metastatic and advanced prostate cancer may include anemia, bone marrow suppression, weight loss, pathologic fractures, spinal cord compression, pain, hematuria, ureteral and/or bladder outlet obstruction, urinary retention, chronic renal failure, urinary incontinence, and symptoms related to bony or soft-tissue metastases, among others.

Additional prostate drugs which can be used in combination with the chimeric antibody recruiting compounds according to the present invention include, for example, the enlarged prostate drugs/agents, as well as eulexin, flutamide, goserelin, leuprolide, lupron, nilandron, nilutamide, zoladex and mixtures thereof. Enlarged prostate drugs/agents as above, include for example, ambenyl, ambophen, amgenal, atrosept, bromanyl, bromodiphenhydramine-codeine, bromotuss-codeine, cardura, chlorpheniramine-hydrocodone, ciclopirox, clotrimazole-betamethasone, dolsed, dutasteride, finasteride, flomax, gecil, hexalol, lamisil, lanased, loprox, lotrisone, methenamine, methen-bella-meth Bl-phen sal, meth-hyos-atrp-M blue-BA-phsal, MHP-A, mybanil, prosed/DS, Ro-Sed, S-T Forte, tamsulosin, terbinafine, trac, tussionex, ty-methate, uramine, uratin, uretron, uridon, uro-ves, urstat, usept and mixtures thereof.

The term "breast cancer" or "malignant breast neoplasm" is used to describe a type of cancer originating from breast tissue, most commonly from the inner lining of milk ducts or the lobules that supply the ducts with milk. Cancers originating from ducts are known as ductal carcinomas; those originating from lobules are known as lobular carcinomas. Breast cancer is a disease of humans and other mammals; while the overwhelming majority of cases in humans are women, men can sometimes also develop breast cancer.

Worldwide, breast cancer comprises about a quarter of all cancers (excluding non-melanoma skin cancers) in women. In 2008, breast cancer caused 458,503 deaths worldwide (13.7% of cancer deaths in women). Breast cancer is more than 100 times more common in women than breast cancer in men, although males tend to have poorer outcomes due to delays in diagnosis.

Prognosis and survival rates vary greatly depending on cancer type, staging and treatment, and geographical location of the patient. Survival rates in the Western World are very good, for instance, overall, more than 8 out of 10 women in England that are diagnosed with the disease survive it for at least 5 years. In the developing countries, however, survival rates are much poorer.

The size, stage, rate of growth, and other characteristics of the tumor determine the kinds of treatment. Treatment may include surgery, drugs (hormonal therapy and chemotherapy), radiation and/or immunotherapy. Surgical removal of the tumor provides the single largest benefit, with surgery alone being capable of producing a cure in many cases. To somewhat increase the likelihood of long-term disease-free survival, several chemotherapy regimens are commonly given in addition to surgery, including for example CMF (cyclophosphamide, methotreate and 5-fluorouracil—often given 4-weekly for 6 cycles); FAC/CAF (5-fluorouracil, doxorubicin, cyclophosphamide—often given 3-weekly for 6 cycles); AC/CA (Adriamycin/doxorubicin and cyclophosphamide—given 3-weekly for 4 cycles); AC-Taxol (AC given 3-weekly for 4 cycles followed by paclitaxel given either 3-weekly for 4 cycles or weekly, at a smaller dose, for 12 weeks); TAC (Taxotere/docetazel, Adriamycin/doxorubicin and cyclophosphamide given 3-weekly for 6 cycles); FEC (5-fluorouracil, epirubicin and cyclphosphamide—given 3-weekly for 6 cycles); FECD (FEC given 3-weekly for 3 cycles followed by docetaxel 3-weekly for 3 cycles); TC (Taxotere/docetaxel and cyclophosphamide given 3-weekly for 4 or 6 cycles). In addition to chemotherapy, trastuzumab may also be added to the regimen depending on the tumor characteristics and risk of relapse. It is usually given either 3 weekly or weekly for a total duration of 1 year. In addition, since chemotherapy affects the production of white blood cells, granulocyte colony-stimulating factor (G-CSF) is sometimes administered along with chemotherapy. This has been shown to reduce, though not completely prevent, the rate of infection and low white cell count. Most adjuvant breast cancer chemotherapy regimens do not routinely require growth factor support except for those associated with a high incidence of bone marrow suppression and infection.

The term "melanoma" is used to describe a malignant tumor of melanocytes which are found predominantly in skin but also in the bowel and the eye (see uveal melanoma), even though melanoma can be found in any part of the body. Melanoma is a form of cancer that begins in melanocytes, the cells that make skin pigment, or melanin. It may begin in a mole (skin melanoma), but can also begin in other pigmented tissues. There are several types of melanoma, defined by where they first appear, including skin and eye melanoma and in rare instances in the GI tract or lymph nodes Melanoma is one of the rarer types of skin cancer but causes the majority of skin cancer related deaths. Malignant melanoma is a serious type of skin cancer. It is due to uncontrolled growth of pigment cells, called melanocytes. Despite many years of intensive laboratory and clinical research, the sole effective cure is surgical resection of the primary tumor before it achieves a Breslow thickness greater than 1 mm.

Around 160,000 new cases of melanoma are diagnosed worldwide each year. About 48,000 melanoma related deaths occur worldwide per year. Malignant melanoma accounts for 75 percent of all deaths associated with skin cancer. The treatment includes surgical removal of the tumor; adjuvant treatment; chemo- and immunotherapy, or radiation therapy. The severity of melanoma is often characterized by the Clark level, which are for thin tumors and describe how deeply the cancer has spread into the skin, and the Breslow depth, which refers to the microscopic depth of tumor invasion.

The following stages are identified in the progression of the melanoma disease state. Melanoma progresses from an early stage (in situ) through an invasive stage, a high risk melanoma stage, a regional metastatic stage and a distant metastatic stage with varying degrees of survivability, as set forth below.

Melanoma Stages:
Stage 0: Melanoma in Situ (Clark Level I), 99.9% Survival
Stage I/II: Invasive Melanoma, 85-95% Survival
　T1a: Less than 1.00 mm primary, w/o Ulceration, Clark Level II-III
　T1b: Less than 1.00 mm primary, w/Ulceration or Clark Level IV-V
　T2a: 1.00-2.00 mm primary, w/o Ulceration
Stage II: High Risk Melanoma, 40-85% Survival
　T2b: 1.00-2.00 mm primary, w/ Ulceration
　T3a: 2.00-4.00 mm primary, w/o Ulceration
　T3b: 2.00-4.00 mm primary, w/ Ulceration
　T4a: 4.00 mm or greater primary w/o Ulceration
　T4b: 4.00 mm or greater primary w/ Ulceration
Stage III: Regional Metastasis, 25-60% Survival
　N1: Single Positive Lymph Node
　N2: 2-3 Positive Lymph Nodes OR Regional Skin/In-Transit Metastasis
　N3: 4 Positive Lymph Nodes OR Lymph Node and Regional Skin/In Transit Metastases
Stage IV: Distant Metastasis, 9-15% Survival
　M1a: Distant Skin Metastasis, Normal LDH
　M1b: Lung Metastasis, Normal LDH
　M1c: Other Distant Metastasis OR Any Distant Metastasis with Elevated LDH
Based Upon AJCC 5-Year Survival with Proper Treatment Tradition therapy of melanoma involves a number of treatment options. These generally include surgery, chemotherapy, radiation therapy and immunotherapy (IL-2, other). In the case of surgery, treatment can vary and can include local excision, wide local excision, lymphadenectomy, sentinel lymph node biopsy and skin grafting. In the case of chemotherapy, a standard chemotherapeutic agent dacarbazine (DTIC) is administered to the patient in order to treat the cancer, generally through cancer cell death. In the case of radiation therapy, radiation is used as a palliative rather than a cure for melanoma. Radiation relieves bone pain and other symptoms caused by metastases to the bones, brain, and organs such as the liver. Although not curative, radiation treatment is being investigated for more widespread use in controlling other symptoms of skin cancer. In the case of immunotherapy (biologic treatment), a patient's natural immune system is raised or other immune compositions (IL-2) are administered to the patient against the cancer.

"Metastatic caner" refers to a progressed form of cancer, including prostate cancer, breast cancer, ovarian cancer, cervical cancer, placental cancer, melanoma, colon cancer, glioblastoma, neuroblastoma, lung, including non-small cell lung cancer, kidney (hepatocellular), lymphoma, leukemia, including T-cell leukemia, as well as cancers which have metastasized from those cancers, (especially prostate, breast and melanoma) among others wherein the original cancer has metastasized to another area of the body, including skin especially in the case of melanoma (regional or distant) or to other non-skin tissue (e.g., lungs, liver, brain, lymph system). Metastatic cancer describes when cancer has spread into surrounding healthy tissue and through the bloodstream, or lymphatic system, to other parts of the body. In the case of metastatic cancer, if the cancer spreads to other areas, the cancer cells in the new tumor generally are still considered to be the same cancer cells, but the disease is called metastatic cancer.

In the case of metastatic melanoma as well as other metastatic cancers, unlike the early stages of cancer, including melanoma, which can be treated successfully with early diagnosis, the prognosis for patients diagnosed with metastatic cancer is often poor, with survival rates of six to nine months.

In the case of metastatic melanoma, in the past 35 years, the FDA has only approved two types of therapies for metastatic melanoma—interleukin 2 (IL-2) and DTIC. The methods of treatment for metastatic melanoma as well as other metastatic cancers often include radiation, immunotherapy, chemotherapy and palliative surgery. Currently, there are no approved therapies that significantly improve survival for patients with metastatic melanoma.

The term "imaging", "molecular imaging" or "radioimaging is used to describe methods that use the nuclear properties of matter in diagnosis and therapy, pursuant to the present invention. More specifically, the present invention relies on molecular imaging because it produces images that reflect biological processes that take place at the cellular and subcellular level.

Molecular imaging is a discipline that unites molecular biology and in vivo imaging. It enables the visualisation of the cellular function and the follow-up of the molecular process in living organisms without perturbing them. The multiple and numerous potentialities of this field are applicable to the diagnosis and treatment of diseases such as cancer, in the present invention, in particular, prostate cancer, breast cancer, ovarian cancer, cervical cancer, placental cancer, melanoma, colon cancer, glioblastoma, neuroblastoma, lung, including non-small cell lung cancer, kidney (hepatocellular), lymphoma, leukemia, including T-cell leukemia, as well as cancers which have metastasized from those cancers, among others, including metastatic melanoma. This technique also contributes to improving the treatment of these disorders by optimizing the pre-clinical and clinical tests of new medication. This approach also has a major economic impact due to earlier and more precise diagnosis.

Molecular imaging differs from traditional imaging in that probes labeled biomarkers are used to help image particular targets or pathways. Biomarkers interact chemically with their surroundings and in turn alter the image according to molecular changes occurring within the area of interest. This process is markedly different from previous methods of imaging which primarily imaged differences in qualities such as density or water content. This ability to image fine molecular changes opens up an incredible number of exciting possibilities for medical application, including early detection and treatment of disease, in particular, cancer and metastatic cancer, including prostate cancer, breast cancer, ovarian cancer, cervical cancer, placental cancer, melanoma, colon cancer, glioblastoma, neuroblastoma, lung, including non-small cell lung cancer, kidney (hepatocellular), lymphoma, leukemia, including T-cell leukemia, as well as cancers which have metastasized from those cancers, among others, according to the present invention.

There are a number of different imaging modalities that can be used for noninvasive molecular imaging, using compounds according to the present invention. Each have different strengths and weaknesses and some are more adept at imaging multiple targets or sites than others. This is important in instances where metastatic cancer is suspected. The modalities which can be used in the present invention are varied and in the present invention principally include single photon emission computed tomography (SPECT) and positron emission tomography (PET), discussed below.

The main purpose of SPECT when used in cancer imaging pursuant to the present invention is to measure the distribution of radioisotope in prostate and breast cancer lesions, including metastatic cancer is suspected. The development of computed tomography in the 1970s allowed mapping of the distribution of the radioisotopes in tissue, and led to the technique now called SPECT.

The imaging agent used in SPECT emits gamma rays, as opposed to the positron emitters used in PET. There are a number of radioisotopes (such as $^{99m}$Tc, $^{111}$In, $^{123}$I, $^{201}$Tl, $^{67}$Ga, $^{99m}$Tc and $^{203}$Pb, among other gamma ray emitters) that can be used in the present invention and imaged with SPECT technology. In SPECT, where possible, by rotating the gamma camera around the area to be analyzed, a three dimensional image of the distribution of the radiotracer may be obtained by employing filtered back projection or other tomographic techniques. The radioisotopes used in SPECT have relatively long half lives (a few hours to a few days) making them easy to produce and relatively cheap in comparison to other radioisotopes. This represents the major advantage of SPECT as an imaging technique, since it is significantly cheaper than PET or other imaging methods such as magnetic resonance imaging (MRI). However, SPECT sometimes lacks exceptional spatial (i.e., where exactly the particle is) or temporal (i.e., did the contrast agent signal happen at a particular millisecond or not) resolution. Make sure it is true statement.

Another imaging technique which finds particular use in the present invention is positron emission tomography (PET). In PET, a molecule is tagged with a positron emitting isotope. These positrons (β particles) interact with nearby electrons, emitting two 511,000 eV photons, directed 180 degrees apart in opposite directions. These photons are then detected by the scanner which can estimate the density of positron annihilations in a specific area. When enough interactions and annihilations have occurred, the density of the original molecule may be measured in that area. Typical isotopes include $^{11}$C, $^{13}$N, $^{15}$O, $^{18}$F, $^{64}$Cu, $^{62}$Cu, $^{124}$I, $^{76}$Br, $^{82}$Rb and $^{68}$Ga, among others, including the preferred $^{66}$Ga, $^{68}$Ga, $^{64}$Cu, $^{86}$Y. One of the major disadvantages of PET is that most of the radioisotopes must be made with a cyclotron, thus making the use of PET, in certain instances prohibitively expensive. Most of these probes also have a half life measured in minutes and hours, thus forcing the cyclotron, in many instances, to be on site. These factors can make PET sometimes prohibitively expensive, except in certain cases, which the present invention addresses in certain aspects. PET imaging does have many advantages though. First and foremost is its sensitivity: a typical PET scanner can detect between $10^{-11}$ mol/L to $10^{-12}$ mol/L concentrations.

The term "effective" is used, to describe an amount of a compound, component or composition, which produces an intended effect when used within the context of its use, which may be a diagnostic method, a therapeutic method, a method to monitor the progression of therapy or other method (chemical synthesis) pursuant to the present invention. In the case of therapeutic methods, an effective amount for treating cancer, including prostate cancer, breast cancer, ovarian cancer, cervical cancer, placental cancer, melanoma, colon cancer, glioblastoma, neuroblastoma, lung, including non-small cell lung cancer, kidney (hepatocellular), lymphoma, leukemia, including T-cell leukemia, as well as cancers which have metastasized from those cancers, among others, is that amount which shrinks cancerous tissue (e.g., tumor), produces a remission, prevents further growth of the tumor and/or reduces the likelihood that the cancer in its early stages (in situ or invasive) does not progress further to metastatic cancer.

Noted here is that within the context of the use of the present invention, the patient will be receiving a radiation dose, which provides guidance to the amount of compound which is considered effective when used within the context of its use. A patient undergoing a nuclear medicine procedure will receive a radiation dose. Under present international guidelines it is assumed that any radiation dose, however small, presents a risk. The radiation doses delivered to a patient in a nuclear medicine investigation present a very small risk of side effects, including inducing cancer in the patient. In this respect it is similar to the risk from X-ray investigations except that the dose is delivered internally rather than from an external source such as an X-ray machine.

The radiation dose from a diagnostic nuclear medicine procedure is expressed as an effective dose with units of sieverts (usually given in millisieverts, mSv). The effective dose resulting from an investigation is influenced by the amount of radioactivity administered in megabecquerels (MBq), the physical properties of the radiopharmaceutical used, its distribution in the body and its rate of clearance from the body.

Effective doses can range from 6 μSv (0.006 mSv) for a 3 MBq chromium-51 EDTA measurement of glomerular filtration rate to 37 mSv or more for a 150 MBq thallium-201 non-specific tumour imaging procedure. The common bone scan with 600 MBq of technetium-99m-MDP has an effective dose of 3 mSv. Formerly, units of measurement were the Curie (Ci), being 3.7E10 Bq, and also 1.0 grams of radium (Ra-226); the rad (radiation absorbed dose), now replaced by the Gray; and the rem (röntgen equivalent man), now replaced with the Sievert. The rad and rem are essentially equivalent for almost all nuclear medicine procedures, and only alpha radiation will produce a higher Rem or Sv value, due to its much higher relative biological effectiveness (RBE).

The term "coadministration" or "combination therapy" is used to describe a therapy in which at least two active compounds (one of which is a compound according to the present invention) in effective amounts are used to treat cancer, including metastatic cancer as otherwise described herein at the same time. Although the term coadministration preferably includes the administration of two active compounds to the patient at the same time, it is not necessary that the compounds be administered to the patient at the same time, although effective amounts of the individual compounds will be present in the patient at the same time. Compounds according to the present invention may be administered with one or more compound including anticancer agents, such as a chemotherapeutic agent as otherwise described herein such as dacarbazine (DTIC) for melanoma, among numerous others and/or and immunotherapeutic agent such as IL-2 and/or α-interferon, among other compounds, depending upon the cancer to be treated.

The term "additional anticancer agent" or "traditional anticancer agent" is used to describe a compound other than those of the present invention which may be combined herein for the treatment of cancer. Exemplary anti-cancer agents which may be used in the present invention include, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, gleevac, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH$_2$ acetate [C$_{59}$H$_{84}$N$_{18}$Oi$_4$-(C$_2$H$_4$O$_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dicarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "treating" or "successfully treating" when used in the context of treating cancer, including metastatic cancer, shall include shrinking a tumor, curing the cancer, including cancer which has metastasized (by causing a remission of the cancer in the patient) or reducing the likelihood or preventing the spread of the cancer into other organs. Cancer, including prostate cancer, breast cancer, ovarian cancer, cervical cancer, placental cancer, melanoma, colon cancer, glioblastoma, neuroblastoma, lung, including non-small cell lung cancer, kidney (hepatocellular), lymphoma, leukemia, including T-cell leukemia, as well as cancers which have metastasized from those cancers, among others, may be treated using compounds according to the present invention alone, or in combination with other methods and/or compounds including surgery, chemotherapy (especially the use of the chemotherapeutic agent as otherwise described herein.

In certain aspects of the invention, where the basic compound and in particular, the DOTA group, as described above, is complexed with a radioisotope for purposes of being used in the diagnosis or therapy of cancer, including metastatic cancer, the invention relates to compounds and their pharmaceutically acceptable salts according to the general chemical structure (note that the radioisotope may be complexed to one or more carbonyl/carboxyl groups of the DOTA moiety as well):

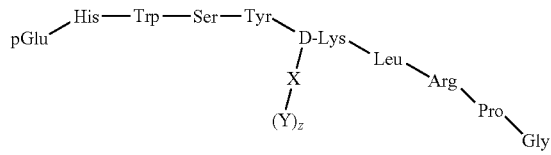

Where X is a

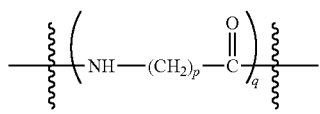

Where p is from 0 to 12, preferably 4 to 8, and q is preferably 0 to 2, more preferably 1;
Y is a

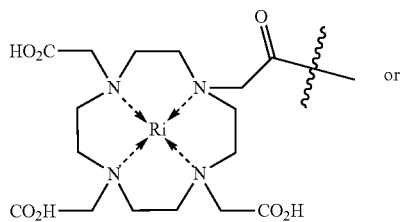 or 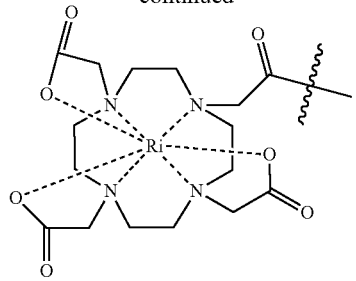

group;
z is preferably 1 or 2; and
the radioisotope ($R_i$) is selected from the group consisting of $^{86}Y$, $^{86}Y$, $^{90}Y$, $^{111}In$, $^{177}Lu$, $^{225}Ac$, $^{212}Bi$, $^{213}Bi$, $^{66}Ga$, $^{67}Ga$, $^{68}Ga$, $^{64}Cu$, $^{67}Cu$, $^{71}As$, $^{72}As$, $^{76}As$, $^{77}As$, $^{65}Zn$, $^{48}V$, $^{203}Pb$, $^{209}Pb$, $^{212}Pb$, $^{166}Ho$, $^{149}Pm$, $^{153}Sm$, $^{201}Tl$, $^{188}Re$, and $^{99m}Tc$. Preferably $R_i$ is $^{111}In$.

Preferred compounds according to the present invention relate to compounds according to the structure (note that the radioisotope may be complexed to one or more carbonyl/carboxyl groups of the DOTA moiety as well):

In preferred aspects, $R_i$ is selected from the group consisting of $^{111}In$, $^{86}Y$, $^{66}Ga$, $^{67}Ga$, $^{68}Ga$, $^{203}Pb$, $^{64}Cu$ end $^{99m}Tc$ when the compounds are to be used diagnostically or to monitor therapeutic intervention and $R_i$ is selected from the group consisting of $^{90}Y$, $^{177}Lu$, $^{186}Re$, $^{188}Re$, $^{212}Bi/^{212}Pb$, $^{213}Bi$, $^{149}Pm$, $^{166}Ho$ and $^{153}Sm$ when compounds according to the present invention are used in radiation therapy to treat cancer, including metastatic cancer.

The present invention also relates to pharmaceutical compositions comprising an effective amount of a compound for diagnostic and/or therapeutic purposes in combination with a pharmaceutically acceptable carrier, additive or excipient in pharmaceutical dosage form. For diagnostic purposes pharmaceutical compositions are formulated generally in parenteral dosage form, especially for intravenous administration, although oral or topical formulations may be useful in certain instances. In the case of the use of compounds according to the present invention for therapeutic purposes, the compositions are formulated preferably in parenteral or topical dosage forms, although orally administered dosage forms are also useful.

The compounds of the present invention, may, in accordance with the invention, be administered in single or divided doses by the oral, parenteral or topical routes. Administration of the active compound may range from a single intravenous injection to continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present invention as sprays, mists, or aerosols for intra-nasal, intra-tracheal or pulmonary administration may also be used. The present invention therefore also is directed to pharmaceutical compositions comprising an effective amount of compound according to the present invention, optionally in combination with a pharmaceutically acceptable carrier, additive or excipient.

The amount of compound used is that amount effective within the context of the administration, whether that administration is for diagnostic purposes or therapeutic purposes. A suitable oral dosage for a compound according to the present invention would be in the range of about 0.01 mg to 10 g or more per day, preferably about 0.1 mg to about 1 g per day. In parenteral formulations, a suitable dosage unit may contain from 0.1 to 250 mg of said compounds, which may be administered from one to four times per day (for diagnostic purpose, preferably once in a bolus dose), whereas for topical administration, formulations containing 0.01 to 1% active ingredient are preferred. It should be understood, however, that the dosage administration from patient to patient will vary and the dosage for any particular patient will depend upon the clinician's judgment, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier, additive or excipient material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like.

The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound according to the present invention can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds. In certain preferred diagnostic and/or therapeutic embodiments, compounds according to the present invention are administered intravenously in sterile saline solution.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Preservatives added may include benzalkonium chloride, chloro-butanol or phenylethyl alcohol, among numerous others.

Additionally, the compounds provided by the invention can be administered by suppository.

In certain aspects according to the present invention, where various cancers are to be treated, the compounds may be co-administered with at least one other anti-cancer agent, as otherwise described herein or an immunotherapeutic agent such as IL-2 and/or α-interferon, among other compounds, depending upon the cancer to be treated. In addition, compounds according to the present invention may be administered prior to, during or after surgery to remove cancerous tissue.

Preparation of compounds according to the present invention proceeds using standard synthetic chemical techniques which are readily available in the art. Synthetic methods for obtaining compounds related to the present invention may be found in the examples section of the present specification. These methods can serve as guides for obtaining compounds according to the present invention. In general, the present compounds may be made by condensing an activated DOTA or other chelating group (containing a leaving group or using a coupling agent to facilitate the binding of the carboxyl group on DOTA or other chelating group to a nucleophilic group on the side chain of an amino acid (e.g. lysine, serine, threonine), especially the amine terminal group of the lysine side chain amino acid, The radionuclide may be complexed to the chelate (DOTA) group either before or after the activated chelate (DOTA) group is condensed onto the amino acid side chain. The peptide with or without a linker is synthesized using conventional peptide synthesis (as otherwise described in the examples section or using methods readily available in the art using protecting group chemistry) and the amide coupling between the lysine amino acid and the linker is readily performed using methods described herein or as otherwise as readily known in the art.

Once the compounds are synthesized, they may be formulated in pharmaceutical dosage form using convention pharmaceutical formulation methods readily available in the art by simply admixing compounds with chosen carriers, additives and/or excipients, depending upon the dosage form to be used and depending upon the use (diagnostic or therapeutic) of the compositions.

The following examples are provided to assist in describing the present invention. The details of these examples and the general description of the examples are for description purposes only and should be seen or taken to limit the scope of the invention in any way.

Examples

Prostate Cancer

The present inventors have been interested in developing radiolabeled GnRH peptides to target the GnRH receptors for cancer detection.[29] Specifically, the inventors coupled the radiometal chelator DOTA (1,4,7,10-tetraazacyclododecane-1,4,7,10-tetraacetic acid) to both epsilon and alpha amino group of $D$-Lys$^6$ in $D$-Lys$^6$-GnRH via an aminohexanoic acid (Ahx) linker to generate novel DOTA-Ahx-($D$-Lys$^6$-GnRH1) and DOTA-Ahx-($D$-Lys$^6$-GnRH2),[29] respectively. The introduction of the Ahx hydrocarbon linker between the DOTA and $D$-Lys$^6$-GnRH enhanced the lipophilicity of the moiety attached to $D$-Lys$^6$-GnRH, which was favorable for GnRH receptor binding.[30] Interestingly, DOTA-Ahx-(D-Lys⁶-GnRH1) displayed 36.1 nM GnRH receptor binding affinity, whereas DOTA-Ahx-(D-Lys⁶-GnRH2) exhibited 10.6 mM GnRH receptor binding affinity.[29] These receptor binding results clearly demonstrated that the epsilon amino group was more suitable for DOTA conjugation. Moreover, the successful imaging of DU145 human prostate cancer-xenografted tumor lesions (GnRH receptor-positive) using $^{111}$In-DOTA-Ahx-(D-Lys⁶-GnRH1) suggested its potential as a novel imaging probe for human prostate cancer imaging.[29] In attempt to extend the application on this novel peptide for human prostate cancer imaging, we determined the tumor targeting and imaging properties of $^{111}$In-DOTA-Ahx-(D-Lys⁶-GnRH1) in DU145 human prostate cancer-xenografted nude mice in this study.

Figure 2:
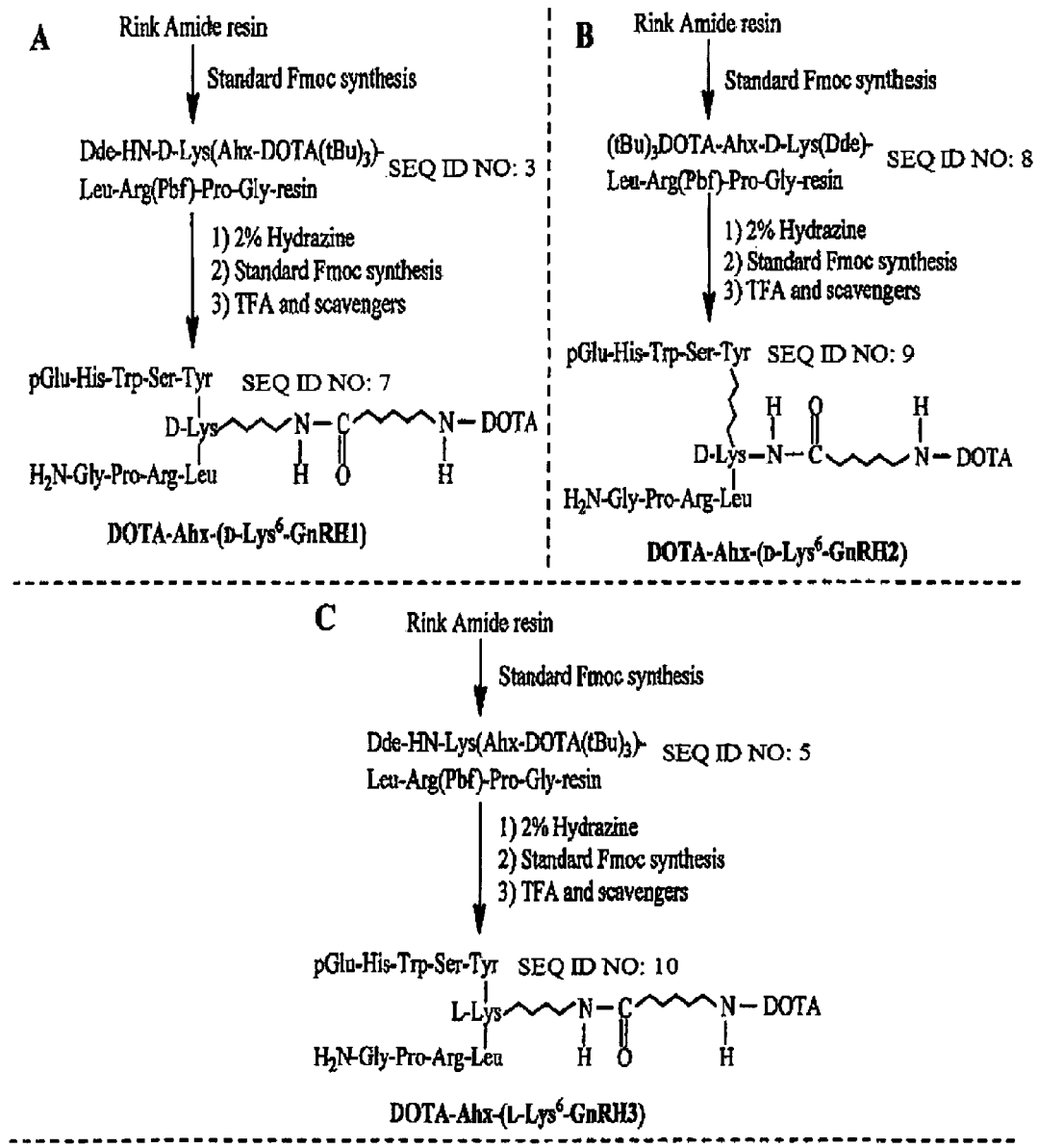
FIG. 2 shows the synthetic schemes of three novel GnRH peptides.
Figure 3:
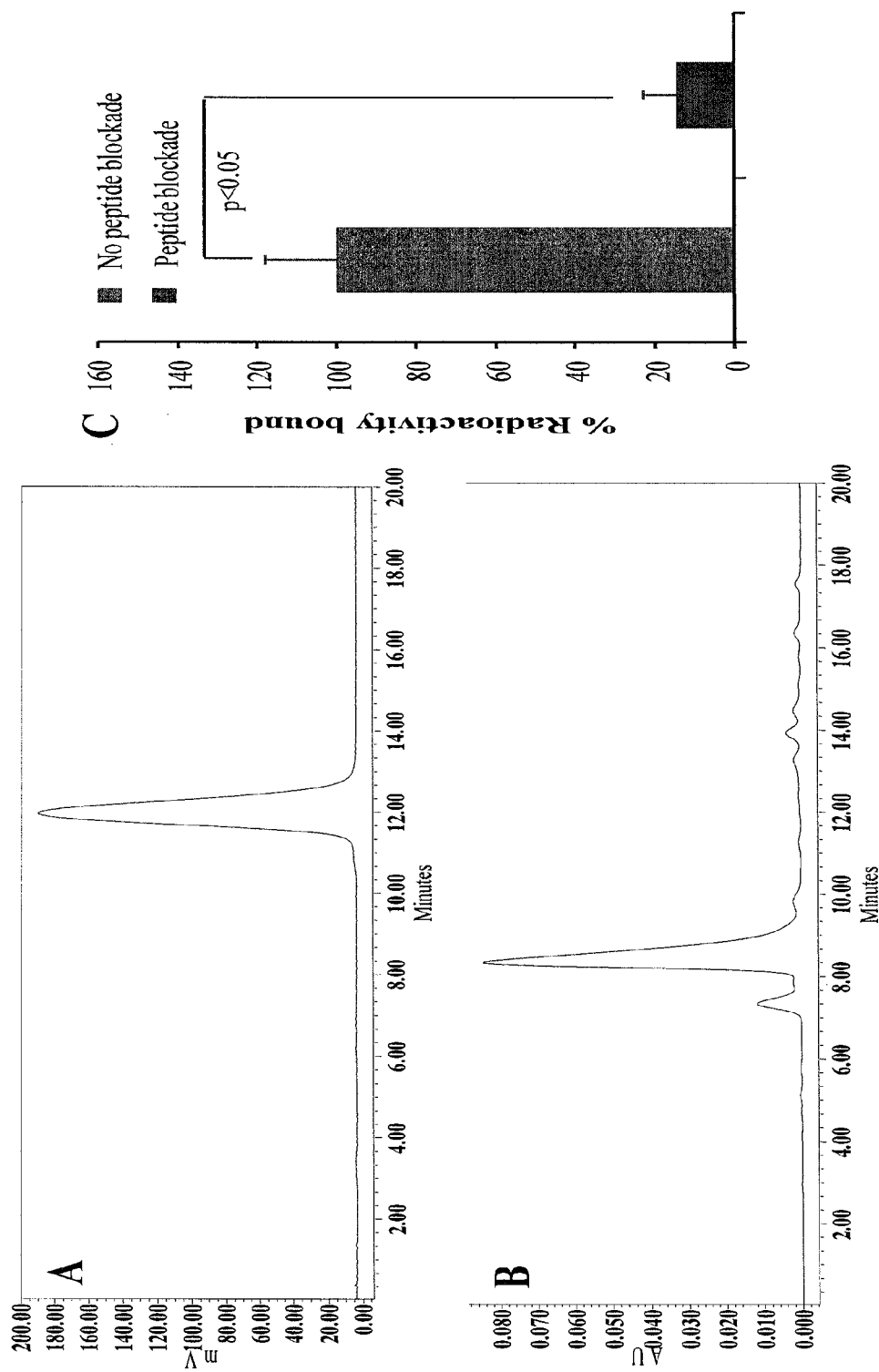
FIG. 3 shows the radioactive HPLC profile of $^{111}In$-DOTA-Ahx-(D-Lys$^6$-GnRH1) (A) and UV HPLC profile of DOTA-Ahx-(D-Lys$^6$-GnRH1) (B); Binding of $^{111}In$-DOTA-Ahx-(D-Lys$^6$-GnRH1) on human GnRH receptor membrane preparations with (right column) or without (left column) the presence of 1 μM of DOTA-Ahx-(D-Lys$^6$-GnRH1). The percentage radioactivity bound was normalized by taking the binding without peptide blockade as 100%. *$P<0.05$.

DOTA-Ahx-(D-Lys⁶-GnRH1) was synthesized according to the published procedure.[29] DOTA-Ahx-(D-Lys⁶-GnRH1) was readily synthesized and purified by RP-HPLC (FIG. 2). The peptide displayed greater than 90% purity after the HPLC purification. The identity of the peptide was confirmed by electrospray ionization mass spectrometry. $^{111}$In-DOTA-Ahx-(D-Lys⁶-GnRH1) (FIG. 1) was readily prepared with greater than 95% radiolabeling yield in a 0.5 M NH₄OAc buffer at pH 4.5. See FIG. 2 hereof. FIG. 3 illustrates the radioactive HPLC profile of $^{111}$In-DOTA-Ahx-(D-Lys⁶-GnRH1) and UV profile of DOTA-Ahx-(D-Lys⁶-GnRH1). $^{111}$In-DOTA-Ahx-(D-Lys⁶-GnRH1) was completely separated from the excess DOTA-Ahx-(D-Lys⁶-GnRH1) by RP-HPLC. The retention times of $^{111}$In-DOTA-Ahx-(D-Lys⁶-GnRH1) and DOTA-Ahx-(D-Lys⁶-GnRH1) were 12.0 and 8.3 min, respectively.

Figure 4:
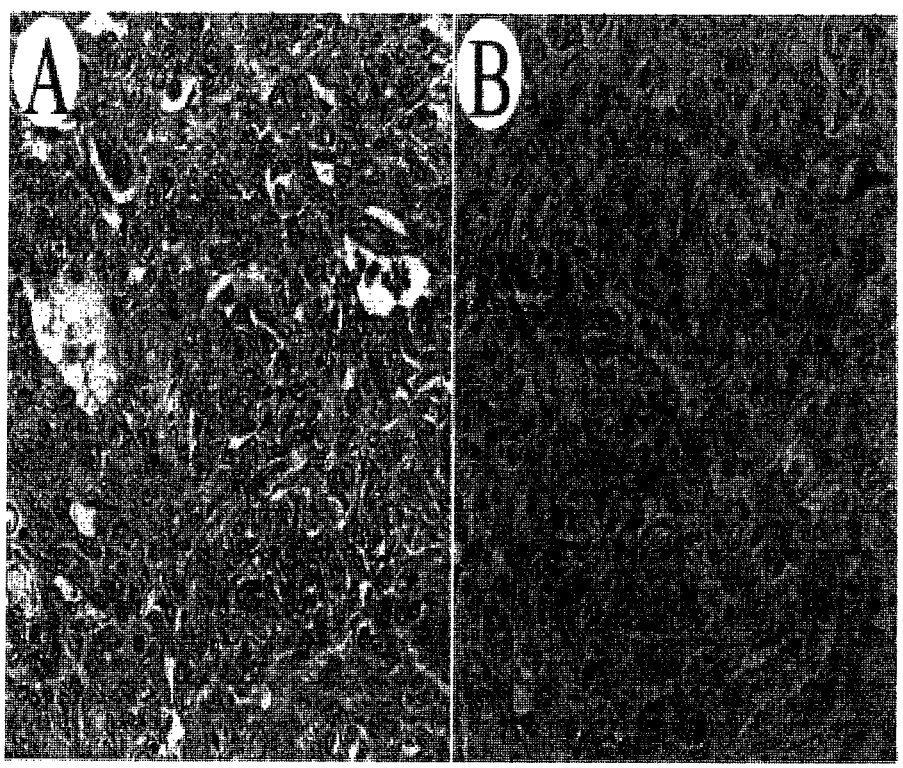
FIG. 4 shows the immunohistochemistry staining of GnRH receptor expressions in DU145 human prostate cancer-xenografted tumor (A, ×400). The DU145 xenografted tumor exhibited strong brown cytoplasmic staining. As a comparison, the DU145 xenografted tumor (B, ×400) were stained without primary goat anti-human GnRH antibody.

The specific GnRH receptor binding of $^{111}$In-DOTA-Ahx-(D-Lys⁶-GnRH1) was determined using human GnRH receptor preparations obtained from Millipore, Inc (Billerica, Mass.). Approximately 86% of the binding of $^{111}$In-DOTA-Ahx-(D-Lys⁶-GnRH1) was competed off by 1 μM of DOTA-Ahx-(D-Lys⁶-GnRH1) peptide (FIG. 3C). The GnRH receptor expressions on DU145 human prostate cancer-xenografted tumor slices were confirmed by immunohistochemistry staining. The staining results are presented in FIG. 4. The GnRH receptor expressions were positively stained in DU145 human prostate cancer-xenografted tumors. Thus, we determined the tumor targeting and pharmacokinetic properties of $^{111}$In-DOTA-Ahx-(D-Lys⁶-GnRH1) in DU145 human prostate cancer-xenografted nude mice.

Figure 5:
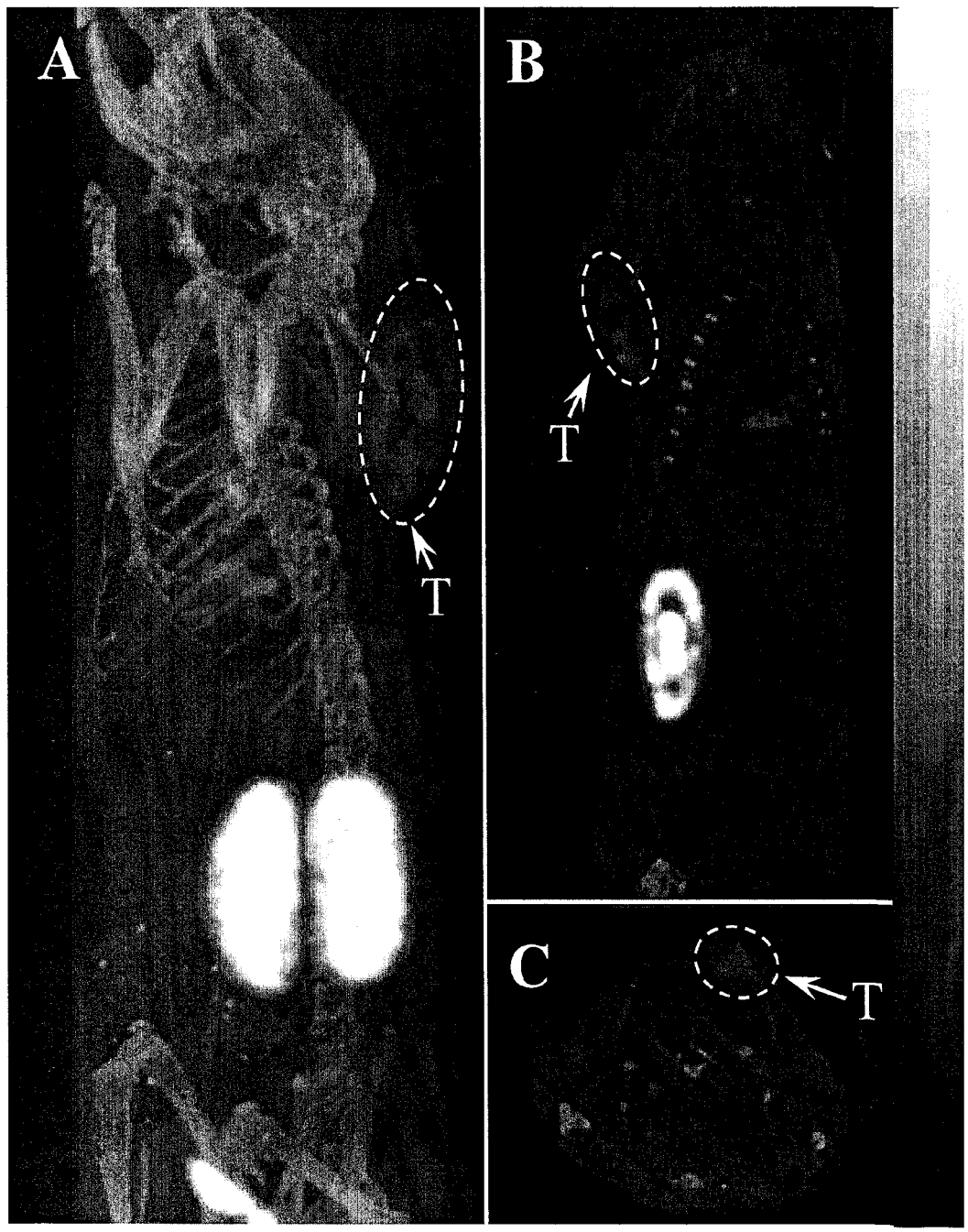
FIG. 5 shows the three-dimensional (A), coronal (B) and transversal (C) SPECT/CT images of DU145 human prostate cancer-xenografted tumor at 0.5 h post-injection of 33.3 MBq of $^{111}In$-DOTA-Ahx-(D-Lys$^6$-GnRH1). The prostate cancer lesions (T) were highlighted with arrows on the images.

The biodistribution results of $^{111}$In-DOTA-Ahx-(D-Lys⁶-GnRH1) are shown in Table 1, below. $^{111}$In-DOTA-Ahx-(D-Lys⁶-GnRH1) exhibited rapid tumor uptake. The tumor uptake was 1.27±0.40 and 0.55±0.23% ID/g at 0.5 and 2 h post-injection. The tumor uptake decreased to 0.38±0.16 and 0.31±0.09% ID/g at 4 and 24 h post-injection. $^{111}$In-DOTA-Ahx-(D-Lys⁶-GnRH1) displayed rapid whole-body clearance, with approximately 91% of the injected radioactivity cleared through the urinary system by 2 h post-injection. The kidneys were the normal organs with the highest uptakes after 2 h post-injection. The renal uptake was 10.93±1.53, 6.41±0.34, 7.29±0.90 and 2.72±0.64% ID/g at 0.5, 2, 4 and 24 h post-injection. The tumor imaging property of $^{111}$In-DOTA-Ahx-(D-Lys⁶-GnRH1) was examined in DU145 human prostate cancer-xenografted nude mice. Representative three-dimensional, coronal and transversal SPECT/CT images are presented in FIG. 5. The DU145 xenografted tumors were clearly visualized by SPECT/CT using $^{111}$In-DOTA-Ahx-(D-Lys⁶-GnRH1) as an imaging probe in at 0.5 h post-injection, highlighting the potential use of $^{111}$In-DOTA-Ahx-(D-Lys⁶-GnRH1) for human prostate cancer imaging.

TABLE 1

Biodistribution of $^{111}$In-DOTA-Ahx-(D-Lys⁶-GnRH1) in DU145 human prostate cancer-xenografted nude mice. The data were presented as percent injected dose/gram or as percent injected dose (Mean ± SD, n = 5).

| Tissue | 0.5 h | 2 h | 4 h | 24 h |
|---|---|---|---|---|
| Percent injected dose/gram (% ID/g) | | | | |
| Tumor | 1.27 ± 0.40 | 0.55 ± 0.23 | 0.38 ± 0.16 | 0.31 ± 0.09 |
| Brain | 0.14 ± 0.06 | 0.10 ± 0.05 | 0.06 ± 0.04 | 0.07 ± 0.02 |
| Blood | 1.25 ± 0.23 | 0.59 ± 0.26 | 0.46 ± 0.38 | 0.49 ± 0.23 |
| Heart | 0.62 ± 0.20 | 0.20 ± 0.07 | 0.24 ± 0.09 | 0.10 ± 0.04 |
| Lung | 2.10 ± 0.12 | 0.32 ± 0.05 | 0.31 ± 0.05 | 0.19 ± 0.05 |
| Liver | 0.97 ± 0.11 | 0.57 ± 0.10 | 0.48 ± 0.02 | 0.56 ± 0.09 |
| Spleen | 0.63 ± 0.21 | 0.46 ± 0.04 | 0.52 ± 0.15 | 0.28 ± 0.06 |
| Stomach | 0.46 ± 0.09 | 0.33 ± 0.33 | 0.17 ± 0.07 | 0.06 ± 0.03 |
| Kidneys | 10.93 ± 1.53 | 6.41 ± 0.34 | 7.29 ± 0.90 | 2.72 ± 0.64 |
| Muscle | 0.36 ± 0.23 | 0.14 ± 0.07 | 0.22 ± 0.05 | 0.25 ± 0.27 |
| Pancreas | 0.61 ± 0.11 | 0.14 ± 0.04 | 0.12 ± 0.03 | 0.07 ± 0.04 |
| Bone | 1.66 ± 0.11 | 0.59 ± 0.19 | 0.68 ± 0.94 | 0.55 ± 0.67 |
| Skin | 2.01 ± 0.50 | 0.26 ± 0.08 | 0.27 ± 0.09 | 0.24 ± 0.16 |
| Uptake ratio of tumor/normal tissue | | | | |
| Tumor/blood | 1.02 | 0.93 | 0.83 | 0.63 |
| Tumor/muscle | 3.53 | 3.93 | 1.73 | 1.24 |
| Percent injected dose (% ID) | | | | |
| Intestines | 1.03 ± 0.14 | 1.12 ± 0.81 | 0.51 ± 0.07 | 0.40 ± 0.09 |
| Urine | 77.12 ± 4.54 | 91.44 ± 1.78 | 92.47 ± 0.78 | 95.75 ± 0.34 |

Figure 6:
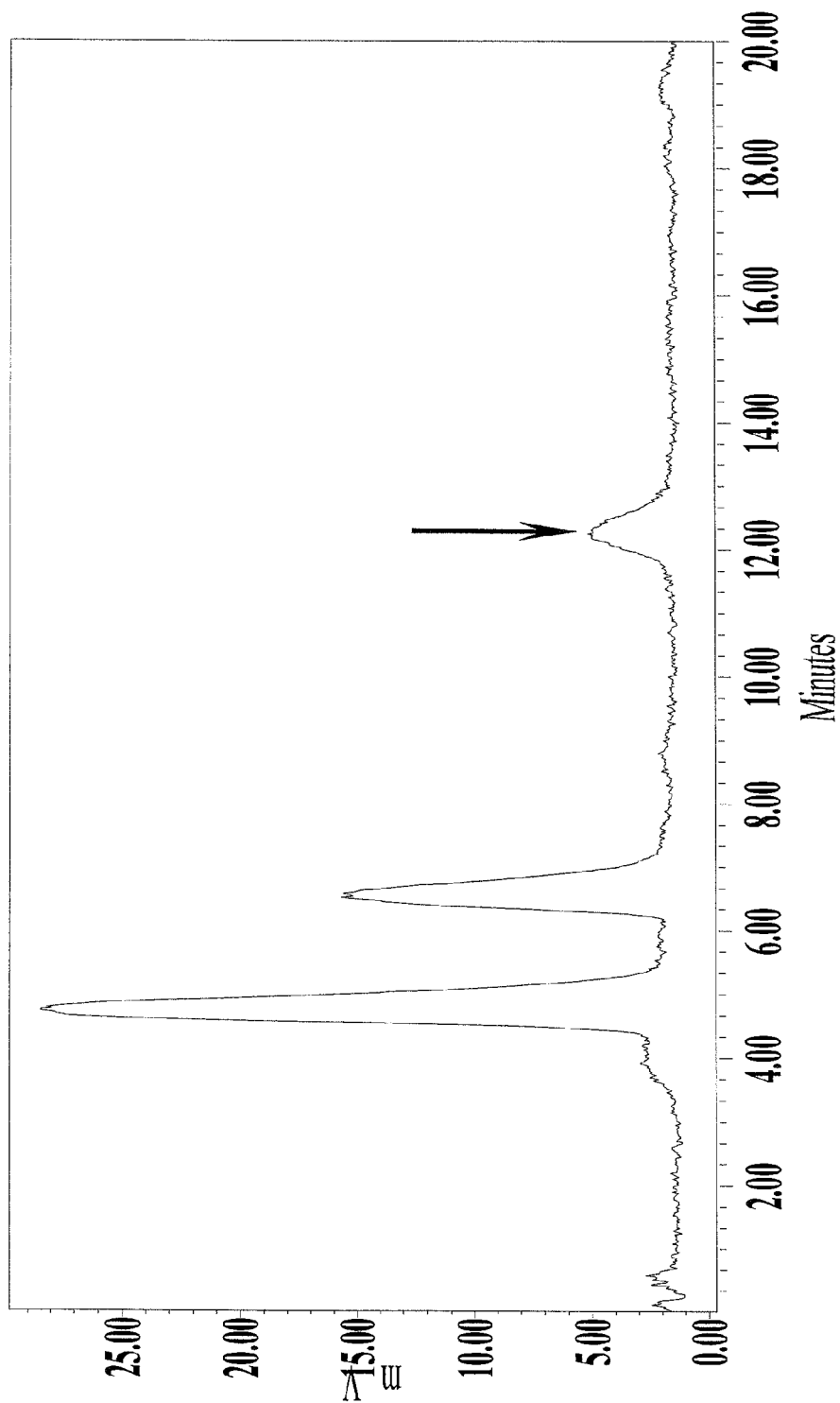
FIG. 6 shows the radioactive HPLC profile of the urine sample of a DU145 human prostate cancer-xenografted nude mouse at 2 h post-injection of $^{111}In$-DOTA-Ahx-(D-Lys$^6$-GnRH1). The arrow indicated the retention time of the original $^{111}In$-DOTA-Ahx-(D-Lys$^6$-GnRH1) prior to the tail vein injection.

The kidneys were the normal organs with the highest radioactivity uptakes in the biodistribution results and SPECT/CT images. Thus, the urinary metabolites of $^{111}$In-DOTA-Ahx-(D-Lys⁶-GnRH1) were analyzed by RP-HPLC at 2 h post-injection. FIG. 6 shows the radioactive HPLC profile of the urine sample. The urine analysis revealed that only 9.8% of $^{111}$In-DOTA-Ahx-(D-Lys⁶-GnRH1) remained intact, whereas 90.2% of $^{111}$In-DOTA-Ahx-(D-Lys⁶-GnRH1) was metabolized into two compounds with higher polarity. Although the identities of the metabolites need to be confirmed in future studies, it was likely that both $^{111}$In-DOTA-Ahx-(D-Lys⁶-GnRH1) and its metabolites contributed to the renal uptake. Lysine co-injection could be potentially utilized to decrease the renal uptake of $^{111}$In-DOTA-Ahx-(D-Lys⁶-GnRH1) since it was successfully used to reduce the renal uptakes of $^{111}$In-labeled alpha-melanocyte stimulating hormone (α-MSH) peptides by 70%.[31] Besides the strategy to decrease renal uptake, it is equally important to increase the tumor uptake in future studies. It was reported that the DOTA-conjugated bombesin peptides with the linkers ranging from 5-carbon (Ava) to 8-carbon (Aoc) exhibited 0.6-1.7 nM receptor binding affinities. Either shorter or longer hydrocarbon linkers dramatically reduce the receptor binding affinity by 100-fold,[32] indicating the profound effect of hydrocarbon linker on the receptor binding affinity. DOTA-Ahx-(D-Lys⁶-GnRH1) displayed 36.1 nM GnRH receptor binding affinity in this study. Substituting the Ahx linker with other hydrocarbon linkers could be a potential way to improve the receptor binding affinity.

The experimental details are presented below and in the references cited herein.[33-36]

Experimental Procedures

Chemicals and Reagents

Amino acids and resin were purchased from Advanced ChemTech Inc. (Louisville, Ky.) and Novabiochem (San Diego, Calif.). DOTA-tri-t-butyl ester was purchased from Macrocyclics Inc. (Richardson, Tex.). $^{111}$InCl₃ was purchased from MDS Nordion, Inc. (Vancouver, Canada) for radiolabeling. $^{125}$I-[D-Trp6]-LH-RH {pGlu-His-Trp-Ser-[$^{125}$I]Tyr-D-Trp-Leu-Arg-Pro-Gly-NH$_2$} was obtained from PerkinElmer Inc. (Boston, Mass.) and ChemiScreen™ Human GnRH receptor membrane preparations were purchased from Millipore, Inc (Billerica, Mass.) for receptor binding studies. GnRHR antibody (N-20, sc-8682) and the ABC Staining Systems were purchased from Santa Cruz Biotechnology, Inc (Santa Cruz, Calif.) for immunohistochemistry (IHC) staining. All other chemicals used in this study were purchased from Thermo Fischer Scientific (Waltham, Mass.) and used without further purification. MDA-MB-231 human breast cancer cells were obtained from American Type Culture Collection (Manassas, Va.).

Specific GnRH Receptor Binding of $^{111}$In-DOTA-Ahx-(D-Lys$^6$-GnRH1):

DOTA-Ahx-(D-Lys$^6$-GnRH1) was synthesized and radiolabeled with $^{111}$In according to our published procedure.[29] The specific GnRH receptor binding of $^{111}$In-DOTA-Ahx-(D-Lys$^6$-GnRH1) was determined using Millipore ChemiScreen™ human GnRH membrane preparations (Millipore, Inc., Billerica, Mass.). Briefly, 504 of human GnRH membrane preparations were incubated at 25° C. for 3 h with approximately 60,000 cpm of HPLC-purified $^{111}$In-DOTA-Ahx-(D-Lys$^6$-GnRH1) in 504 of binding medium {50 mM N-(2-hydroxyethyl)-piperazine-N'-(2-ethanesulfonic acid), 5 mM MgCl$_2$, 1 mM CaCl$_2$, pH 7.4, 0.2% bovine serum albumin (BSA)} with or without 1 µM of DOTA-Ahx-(D-Lys$^6$-GnRH1) peptide blockade. After the incubation, each membrane preparation was mixed with 800 µL of ice-cold washing buffer first, and then filtered through a GF/C filter (Waterman, Clifton, N.J.) pre-soaked in 1% polyethylenimine. Each filter was rinsed with 1 mL of ice-cold washing buffer for three times and counted in a Wallac 1480 automated gamma counter (PerkinElmer, Waltham, Mass.). Statistical analysis was performed using the Student's t-test for unpaired data to determine the significance of differences between the GnRH receptor binding of $^{111}$In-DOTA-Ahx-(D-Lys$^6$-GnRH1) with or without 1 µM of DOTA-Ahx-(D-Lys$^6$-GnRH1) blockade. Difference at the 95% confidence level (p<0.05) was considered significant.

Immunohistochemistry Staining of DU145 Human Prostate Cancer-Xenografted Tumor:

The immunohistochemistry staining was performed on DU145 human prostate cancer-xenografted tumors to demonstrate the GnRH receptor expression. DU145 human prostate cancer cells were obtained from American Type Culture Collection (Manassas, Va.). GnRHR antibody (N-20, sc-8682) and the goat ABC staining system (sc-2023) were purchased from Santa Cruz Biotechnology, Inc (Santa Cruz, Calif.) for immunohistochemistry (IHC) staining of DU145 human prostate cancer-xenografted tumor. The DU145 human prostate cancer-xenografted tumors were generated through flank subcutaneous inoculations of DU145 cells (1×10$^7$ cells/mouse) in male athymic nude mice. The tumor weights reached approximately 0.3 g at 18 days post cell inoculation. The immunoperoxidase staining of the xenografted DU145 tumor slices (4-µm thickness) were performed according to the protocol of goat ABC staining system. Briefly, the tumor slices were treated with 3% H$_2$O$_2$ for 15 min followed by a 20 min-treatment with the blocking serum at 25° C. Then, the tumor slices were incubated with primary goat anti-human GnRH antibody (1:40) for 1.75 h at 25° C. Thereafter, the tumor slices were incubated with biotinylated secondary antibody for 30 min and followed by a 30 min-incubation with AB enzyme reagent. The tumor slices were incubated with the peroxidase substrate for 5 min followed by a dehydration process using ethanol and xylene. After the immunoperoxidase staining, the tumor slices were washed with de-ionized water and counterstained with Gill's formulation #2 hematoxylin. One to two drops of DPX permanent mounting medium were immediately added to the tumor slices after the counterstaining. Then, the tumor slices were covered with glass coverslips and observed by the light microscopy. As controls, the xenografted DU145 tumor slices (4-thickness) were incubated (without primary goat anti-human GnRH antibody) with secondary biotinylated antibody, AB enzyme reagent and peroxidase substrate, respectively.

Biodistribution and Tumor Imaging of $^{111}$In-DOTA-Ahx-(D-Lys$^6$-GnRH1):

All the animal studies were conducted in compliance with Institutional Animal Care and Use Committee approval. The pharmacokinetics of $^{111}$In-DOTA-Ahx-(D-Lys$^6$-GnRH1) was determined in DU145 human prostate cancer-xenografted male athymic nude mice (Harlan, Indianapolis, Ind.). The nude mice were subcutaneously inoculated with 1×10$^7$ DU145 cells on the right flank of each mouse to generate DU145 xenografted tumors. The tumor weights reached approximately 0.3 g at 18 days post cell inoculation. Each tumor-bearing mouse was injected with 0.037 MBq of 111In-DOTA-Ahx-(D-Lys6-GnRH1) via the tail vein. Groups of 5 mice were sacrificed at 0.5, 2, 4 and 24 h post-injection, and tumors and organs of interest were harvested, weighed and counted. Blood values were taken as 6.5% of the whole-body weight. To determine the tumor imaging property of $^{111}$In-DOTA-Ahx-(D-Lys$^6$-GnRH1), approximately 33.3 MBq of $^{111}$In-DOTA-Ahx-(D-Lys$^6$-GnRH1) was injected into a DU145 human prostate cancer-xenografted nude mouse (18 days post the cell inoculation) via the tail vein. The mouse was sacrificed for small animal SPECT/CT (Nano-SPECT/CT®, Bioscan) imaging at 0.5 h post-injection. The CT imaging was immediately followed by the whole-body SPECT imaging. The SPECT scans of 24 projections were acquired. Reconstructed SPECT and CT data were visualized and co-registered using InVivoScope (Bioscan, Washington D.C.).

Urinary Metabolites of $^{111}$In-DOTA-Ahx-(D-Lys$^6$-GnRH1):

One hundred microliters of HPLC purified $^{111}$In-DOTA-Ahx-(D-Lys$^6$-GnRH1) (2.4 MBq) was injected into a DU145 human prostate cancer-xenografted nude mouse through the tail vein. At 2 h post-injection, the mouse was sacrificed and the urine was collected for metabolites analysis. The urine was centrifuged at 16,000 g for 5 min prior to the HPLC analysis. The radioactive metabolites in the urine were analyzed by injecting aliquots of the urine into HPLC. A 20-minute gradient of 15-25% acetonitrile/20 mM HCl was used for the urine analysis.

Examples

Breast Cancer

The present inventors designed and evaluated three novel DOTA-conjugated GnRH peptides to determine the effect of DOTA position on the binding affinity of the GnRH peptide. Specifically, the metal chelator DOTA was coupled to the epsilon and alpha amino groups of D-Lys$^6$ in D-Lys$^6$-GnRH via an aminohexanoic acid (Ahx) hydrocarbon linker to yield DOTA-Ahx-(D-Lys$^6$-GnRH1) and DOTA-Ahx-(D-Lys$^6$-GnRH2), respectively. In a parallel study, the DOTA was coupled to the epsilon amino group of L-Lys$^6$ to generate DOTA-Ahx-(L-Lys$^6$-GnRH3). The GnRH receptor binding affinities of these three peptides were determined using Millipore ChemiScreen™ human GnRH receptor membrane preparations. Only DOTA-Ahx-(D-Lys$^6$-GnRH1) displayed low nanomolar GnRH receptor binding affinity. Hence, we further evaluated the tumor targeting and imaging properties of $^{111}$In-DOTA-Ahx-(D-Lys$^6$-GnRH1) in MDA-MB-231 human breast cancer-xenografted nude mice.

Peptide Synthesis

Three GnRH peptides were synthesized using 9-fluorenyl-methyloxycarbonyl (Fmoc) chemistry. Briefly, the intermediate scaffolds of Dde-HN-D-Lys(Dde)-Leu-Arg(Pbf)-Pro-Gly (SEQ ID NO: 3), (tBu)$_3$DOTA-Ahx-D-Lys(Dde)-Leu-Arg(Pbf)-Pro-Gly (SEQ ID NO:4), and Dde-HN-Lys(Ahx-DOTA(tBu)$_3$)-Leu-Arg(Pbf-Pro-Gly (SEQ ID NO:5) were synthesized on Rink amide resin by an Advanced ChemTech multiple-peptide synthesizer (Louisville, Ky.). Severity micromoles of resin, 210 μmol of each Fmoc-protected amino acid and 210 μmol of (tBu)$_3$DOTA were used for the synthesis. The protecting group of Dde in each scaffold was removed by 2% Hydrazine. The moiety of pGlu-His(TrO-Trp (Boc)-Ser(tBu)-Tyr(tBu) (SEQ ID NO: 6) was conjugated to the epsilon amino group of either L-Lys or D-Lys, or the alpha amino group of D-Lys in the intermediate scaffolds. The protecting groups were totally removed by treating with a mixture of trifluoroacetic acid (TFA), thioanisole, phenol, water, ethanedithiol and triisopropylsilane (87.5:2.5:2.5:2.5:2.5:2.5) for 4 h at 25° C. Each peptide was precipitated and washed with ice-cold ether for four times, purified by reverse phase-high performance liquid chromatography (RP-HPLC) and characterized by LC-MS. See FIG. 2.

In Vitro Receptor Binding Assay

The GnRH receptor binding affinities (IC$_{50}$ values) of DOTA-Ahx-(D-Lys$^6$-GnRH1), DOTA-Ahx-(D-Lys$^6$-GnRH2) and DOTA-Ahx-(L-Lys$^6$-GnRH3) were determined by in vitro competitive binding assay according to the published procedure[32] with modifications. Briefly, 5 μL of Millipore ChemiScreen™ human GnRH membrane preparations were incubated at 25° C. for 3 h with approximately 30,000 counts per minute (cpm) of $^{125}$I-[D-Trp$^6$]-LH-RH in the presence of $10^{-11}$ to $10^{-5}$ M of each peptide in 95 μL of binding medium {50 mM N-(2-hydroxyethyl)-piperazine-N'-(2-ethanesulfonic acid), 5 mM MgCl$_2$, 1 mM CaCl$_2$, pH 7.4, 0.2% bovine serum albumin (BSA)}. After the incubation, 800 μL of ice-cold washing buffer (50 mM N-(2-hydroxyethyl)-piperazine-N'-(2-ethanesulfonic acid), 500 mM NaCl, pH 7.4, 0.1% BSA) was added to each mixture. Each resulting mixture was filtered through a GF/C filter (Whatman, Clifton, N.J.) pre-soaked in 1% polyethylenimine. Each filter was rinsed with 1 mL of ice-cold washing buffer for three times. The activities on the filters were measured in a Wallac 1480 automated gamma counter (PerkinElmer, Waltham, Mass.). The IC$_{50}$ value of each peptide was calculated using Prism software (GraphPad Software, La Jolla, Calif.).

Peptide Radiolabeling with $^{111}$In

Among these three synthetic GnRH peptides, only DOTA-Ahx-(D-Lys$^6$-GnRH1) displayed low nanomolar GnRH receptor binding affinity. Hence, we further evaluated DOTA-Ahx-(D-Lys$^6$-GnRH1). $^1$In-DOTA-Ahx-(D-Lys$^6$-GnRH1) was prepared in a 0.5 M NH$_4$OAc buffer at pH 4.5 according to our published procedure[33]. Briefly, 50 μl of $^{111}$InCl$_3$ (37-74 MBq in 0.05 M HCl aqueous solution), 10 μL of 1 mg/mL DOTA-Ahx-(D-Lys$^6$-GnRH1) aqueous solution and 400 μL of 0.5 M NH$_4$OAc (pH 4.5) were added into a reaction vial and incubated at 75° C. for 45 min. After the incubation, 104 of 0.5% EDTA aqueous solution was added into the reaction vial to scavenge potential unbound $^{111}$In$^{3+}$ ions. The radiolabeled DOTA-Ahx-(D-Lys$^6$-GnRH1) was purified to single species by Waters RP-HPLC (Milford, Mass.) on a Grace Vydac C-18 reverse phase analytical column (Deerfield, Ill.) using the following gradient at a 1 mL/min flow rate. The mobile phase consisted of solvent A (20 mM HCl aqueous solution) and solvent B (100% CH$_3$CN). The gradient was initiated and kept at 85:15 A/B for 3 mins followed by a linear gradient of 85:15 A/B to 75:25 A/B over 20 mins. Then, the gradient was changed from 75:25 A/B to 10:90 A/B over 3 mins followed by an additional 5 mins at 10:90 A/B. Thereafter, the gradient was changed from 10:90 A/B to 85:15 A/B over 3 mins. The purified peptide sample was purged with N$_2$ gas for 20 mins to remove the acetonitrile. The pH of final peptide solution was adjusted to 7.4 with 0.1 N NaOH and sterile normal saline for specific binding and animal studies.

In vitro serum stability of $^{111}$In-DOTA-Ahx-(D-Lys$^6$-GnRH1) was determined by incubation in mouse serum at 37° C. for 2 h and monitored for degradation by RP-HPLC. Briefly, 100 μL of HPLC-purified $^{111}$In-DOTA-Ahx-(D-Lys$^6$-GnRH1) solution (~3.7 MBq) was added into 100 μL of mouse serum (Sigma-Aldrich Corp, St. Louis, Mo.) and incubated at 37° C. for 2 h. After the incubation, 200 μL of a mixture of ethanol and acetonitrile (V:V=1:1) was added to precipitate the serum. The resulting mixture was centrifuged at 10,000 g for 5 min to collect the supernatant. The supernatant was purged with N$_2$ gas for 30 min to remove the ethanol and acetonitrile. The resulting sample was mixed with 500 μL of water and injected into RP-HPLC for analysis using the gradient described above.

Immunohistochemistry Staining of MDA-MB-231 Human Breast Cancer-Xenografted Tumor The immunohistochemistry staining was performed on MDA-MB-231 human breast cancer-xenografted tumors to demonstrate the GnRH receptor expression. The MDA-MB-231 human breast cancer-xenografted tumors were generated through flank subcutaneous inoculations of MDA-MB-231 cells (1×10$^7$ cells/mouse) in female Athymic nude mice. The tumor weights reached approximately 0.3 g at 18 days post cell inoculation. The immunoperoxidase staining of the xenografted MDA-MB-231 tumor slices (4-μm thickness) were performed according to the protocol of goat ABC staining system (sc-2023) purchased from Santa Cruz Biotechnology (Santa Cruz, Calif.). Briefly, the tumor slices were treated with 3% H$_2$O$_2$ for 15 min followed by a 20 min-treatment with the blocking serum at 25° C. Then, the tumor slices were incubated with primary goat anti-human GnRH antibody (1:40; Santa Cruz Biotechnology, Santa Cruz, Calif.) for 1.75 h at 25° C. Thereafter, the tumor slices were incubated with biotinylated secondary antibody for 30 min and followed by a 30 min-incubation with AB enzyme reagent. The tumor slices were incubated with the peroxidase substrate for 5 min followed by a dehydration process using ethanol and xylene. After the immunoperoxidase staining, the tumor slices were washed with de-ionized water and counterstained with Gill's formulation #2 hematoxylin. One to two drops of DPX permanent mounting medium were immediately added to the tumor slices after the counterstaining. Then, the tumor slices were covered with glass coverslips and observed by the light microscopy. As controls, the xenografted MDA-MB-231 tumor slices (4-μm thickness) were incubated (without primary goat anti-human GnRH antibody) with secondary biotinylated antibody, AB enzyme reagent and peroxidase substrate, respectively.

Biodistribution and Tumor Imaging

All the animal studies were conducted in compliance with Institutional Animal Care and Use Committee approval. The pharmacokinetics of $^{111}$In-DOTA-Ahx-(D-Lys$^6$-GnRH1) was determined in MDA-MB-231 human breast cancer-xenografted female athymic nude mice (Harlan, Indianapolis, Ind.). The nude mice were subcutaneously inoculated with 1×10$^7$ MDA-MB-231 cells on the right flank of each mouse to generate MDA-MB-231 xenografted tumors. The tumor weights reached approximately 0.3 g at 18 days post cell inoculation. Each tumor-bearing mouse was injected with 0.037 MBq of $^{111}$In-DOTA-Ahx-(D-Lys$^6$-GnRH1) via the tail vein. Groups of 5 mice were sacrificed at 0.5, 2, 4 and 24 h post-injection, and tumors and organs of interest were harvested, weighed and counted. Blood values were taken as 6.5% of the whole-body weight.

To determine the tumor imaging properties of $^{111}$In-DOTA-Ahx-(D-Lys$^6$-GnRH1), approximately 5.6 MBq of $^{111}$In-DOTA-Ahx-(D-Lys-GnRH1) was injected into a MDA-MB-231 human breast cancer-xenografted nude mouse (18 days post the cell inoculation) via the tail vein. The mouse was sacrificed for small animal SPECT/CT (Nano-SPECT/CT®, Bioscan) imaging at 1 h post-injection. The CT imaging was immediately followed by the whole-body SPECT imaging. The SPECT scans of 24 projections were acquired. Reconstructed SPECT and CT data were visualized and co-registered using InVivoScope (Bioscan, Washington D.C.).

Statistical Methods

Statistical analysis was performed using the Student's t-test for unpaired data to determine the significance of differences between the GnRH receptor binding of $^{111}$In-DOTA-Ahx-(D-Lys$^6$-GnRH1) with or without 1 μM of DOTA-Ahx-(D-Lys$^6$-GnRH1) peptide blockade. Difference at the 95% confidence level (p<0.05) was considered significant.

Results

Figure 7:
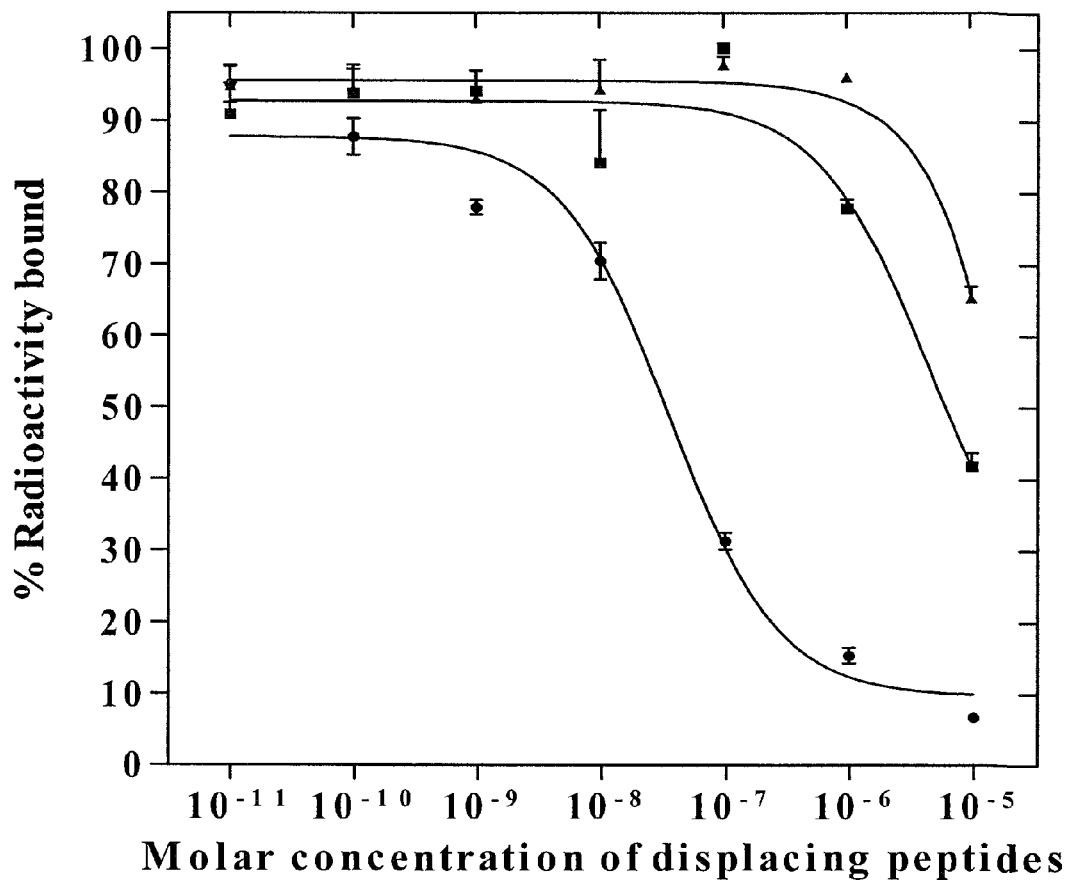
FIG. 7 shows the competitive binding curves of the GnRH peptides. The $IC_{50}$ values of DOTA-Ahx-(D-Lys$^6$-GnRH1), DOTA-Ahx-(D-Lys$^6$-GnRH2) and DOTA-Ahx-(L-Lys$^6$-GnRH3) were 36.1 nM, 10.6 mM and 4.3 mM, respectively.

DOTA-Ahx-(D-Lys$^6$-GnRH1), DOTA-Ahx-(D-Lys$^6$-GnRH2) and DOTA-Ahx-(L-Lys$^6$-GnRH3) were successfully synthesized and purified by RP-HPLC. FIG. 2 illustrates the synthetic schemes of the GnRH peptides. All three GnRH peptides displayed greater than 90% purity after the HPLC purification. The peptide identities were confirmed by electrospray ionization mass spectrometry. The calculated molecular weights of DOTA-Ahx-(D-Lys$^6$-GnRH1), DOTA-Ahx-(D-Lys$^6$-GnRH2) and DOTA-Ahx-(L-Lys$^6$-GnRH3) were 1752.9, 1752.9 and 1752.9, whereas the found molecular weights of DOTA-Ahx-(D-Lys$^6$-GnRH1), DOTA-Ahx-(D-Lys$^6$-GnRH2) and DOTA-Ahx-(L-Lys$^6$-GnRH3) were 1752.2, 1752.2 and 1752.4, respectively. The GnRH receptor binding affinities of the peptides are presented in FIG. 7. The IC$_{50}$ values of DOTA-Ahx-(D-Lys$^6$-GnRH1), DOTA-Ahx-(D-Lys$^6$-GnRH2) and DOTA-Ahx-(L-Lys$^6$-GnRH3) were 36.1 nM, 10.6 mM and 4.3 mM, respectively.

Figure 8:
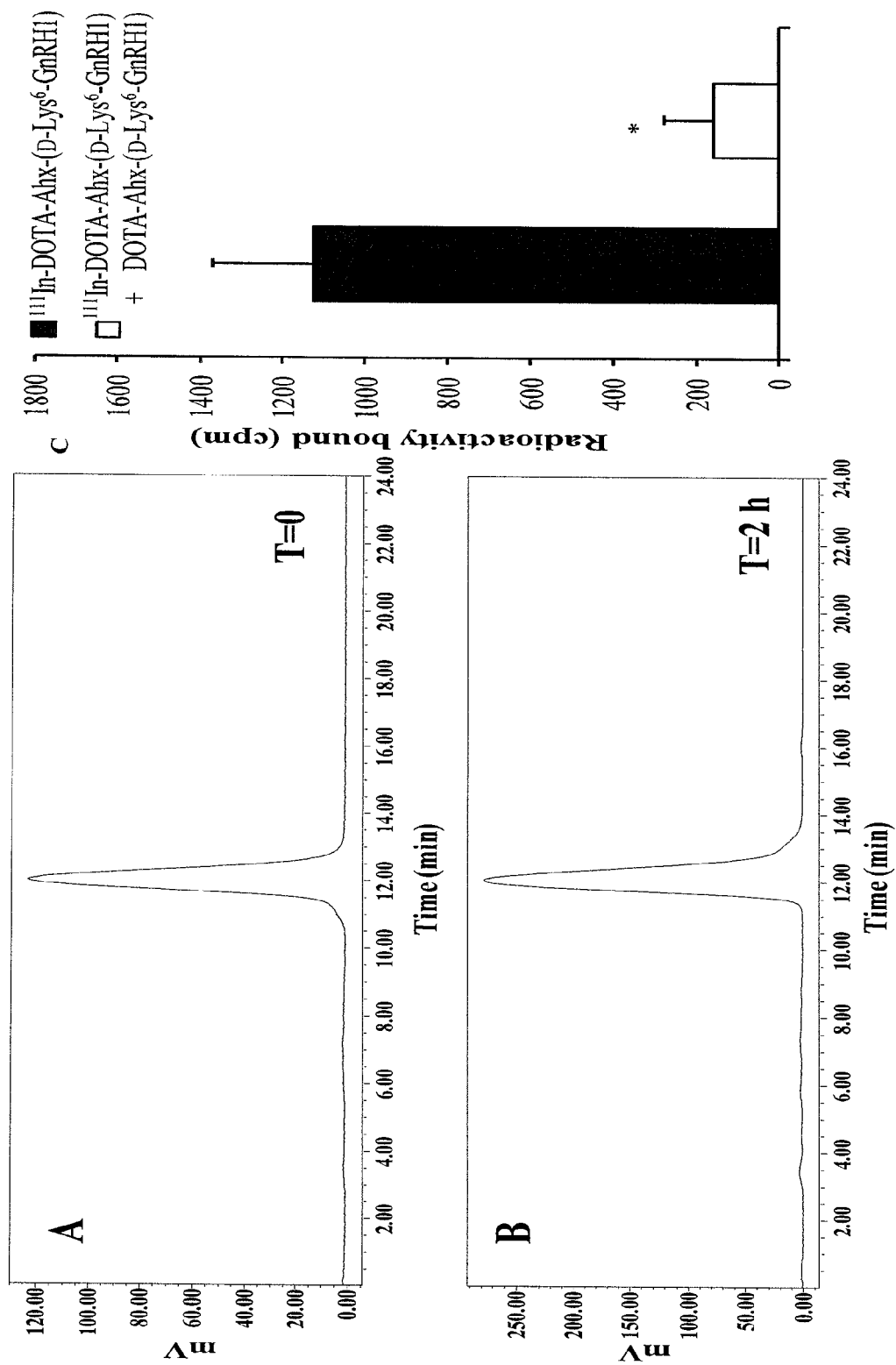
FIG. 8 shows the radioactive HPLC profiles of $^{111}In$-DOTA-Ahx-(D-Lys$^6$-GnRH1) (A, T=0) and its mouse serum stability (B, T=2 h) after 2 h incubation at 37° C. The retention time of $^{111}In$-DOTA-Ahx-(D-Lys$^6$-GnRH1) was 12.0 min; Binding of $^{111}In$-DOTA-Ahx-(D-Lys$^6$-GnRH1) on human GnRH receptor membrane preparations (C) with (□ right graph) or without (■ left graph) the presence of 1 μM of DOTA-Ahx-(D-Lys$^6$-GnRH1). *$P<0.05$.

The inventors further evaluated DOTA-Ahx-(D-Lys$^6$-GnRH1) since only DOTA-Ahx-(D-Lys$^6$-GnRH1) exhibited low nanomolar GnRH receptor binding affinity. DOTA-Ahx-(D-Lys$^6$-GnRH1) was readily labeled with $^{111}$In in 0.5 M ammonium acetate solution at pH 4.5 with greater than 95% radiolabeling yield. $^{111}$In-DOTA-Ahx-(D-Lys6-GnRH1) was completely separated from its excess non-labeled peptide by RP-HPLC. The retention times of $^{111}$In-DOTA-Ahx-(D-Lys$^6$-GnRH1) and DOTA-Ahx-(D-Lys$^6$-GnRH1) were 12.0 and 8.3 min, respectively. In-DOTA-Ahx-(D-Lys$^6$-GnRH1) was stable in mouse serum at 37° C. for 2 h. Only intact $^{111}$In-DOTA-Ahx-(D-Lys$^6$-GnRH1) was detected by RP-HPLC after 2 h of incubation in mouse serum (FIG. 3). The GnRH receptor binding of $^{111}$In-DOTA-Ahx-(D-Lys$^6$-GnRH1) is shown in FIG. 8. Incubation of 1 μM of DOTA-Ahx-(D-Lys$^6$-GnRH1) peptide blocked 86% of the binding of $^{111}$In-DOTA-Ahx-(D-Lys$^6$-GnRH1), indicating that the binding of $^{111}$In-DOTA-Ahx- (D-Lys$^6$-GnRH1) was GnRH receptor-specific.

Figure 9:
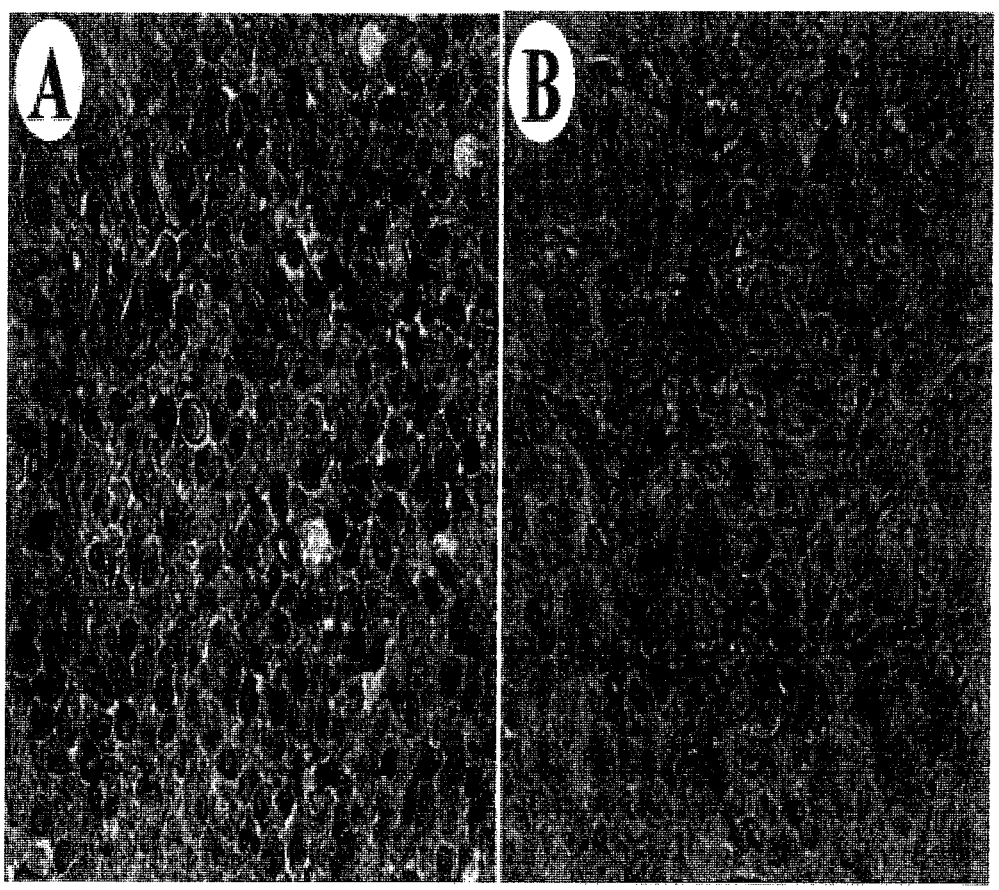
FIG. 9 shows the immunohistochemistry staining of GnRH receptor expressions in MDA-MB-231 human breast cancer-xenografted tumor (A, ×400). The MDA-MB-231 xenografted tumor exhibited strong brown cytoplasmic staining. As a comparison, the MDA-MB-231 xenografted tumor were stained without primary goat anti-human GnRH antibody (B, ×400).
Figure 10:
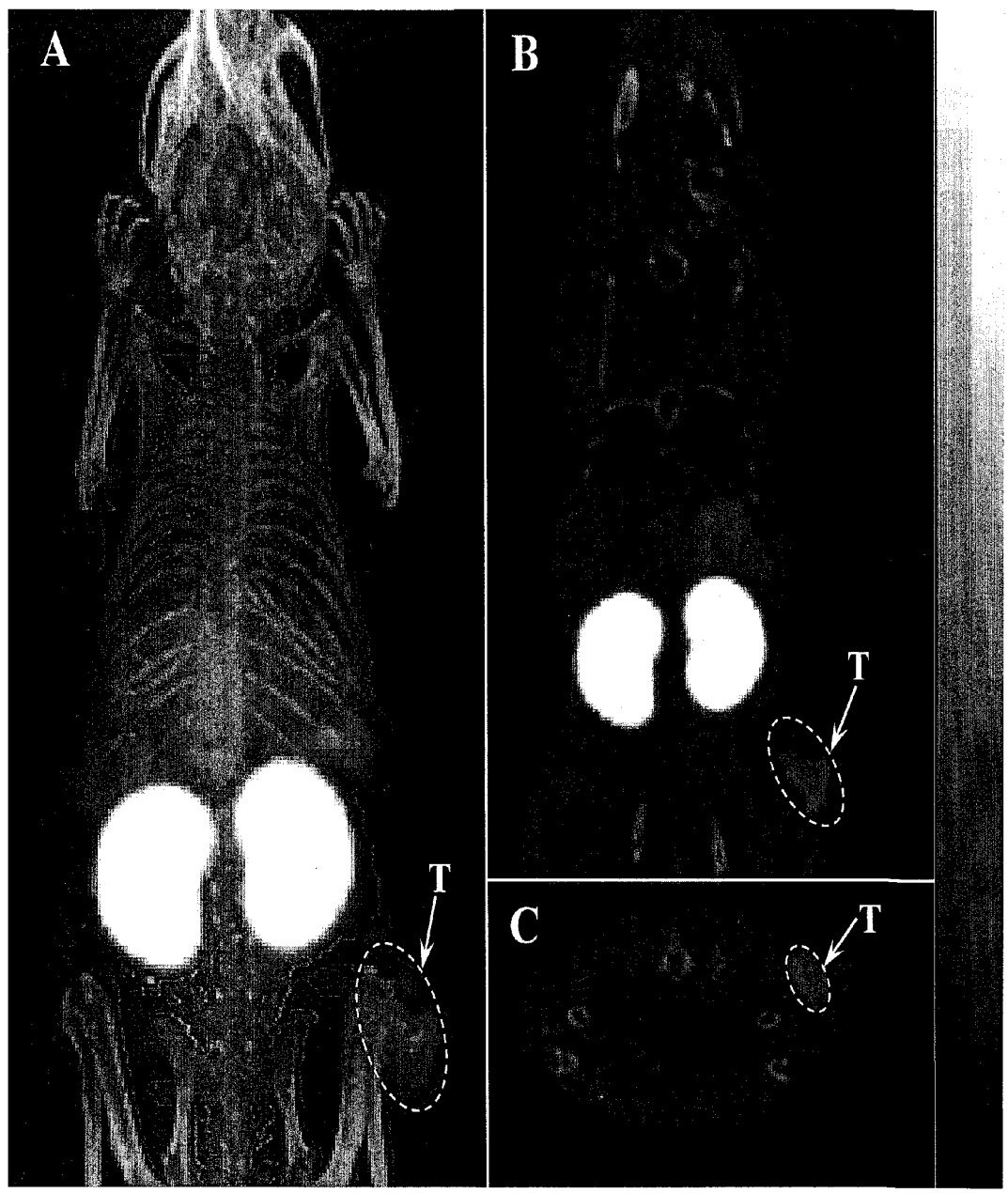
FIG. 10 shows three-dimensional (A), coronal (B) and transversal (C) SPECT/CT images of MDA-MB-231 human breast cancer-xenografted tumor at 1 h post-injection of 5.6 MBq of $^{111}$In-DOTA-Ahx-(D-Lys$^6$-GnRH1). Flank breast cancer lesions (T) were highlighted with arrows on the images.

The GnRH receptor expressions in MDA-MB-231 human breast cancer-xenografted tumors slices were confirmed by immunohistochemistry staining. The immunohistochemistry staining results are presented in FIG. 9. The GnRH receptor expressions were positively stained in MDA-MB-231 human breast cancer-xenografted tumors. Hence, we used the MDA-MB-231 human breast cancer-xenografted nude mice to determine the tumor targeting and pharmacokinetic properties of $^{111}$In-DOTA-Ahx-(D-Lys$^6$-GnRH1). The biodistribution results of $^{111}$In-DOTA-Ahx-(D-Lys$^6$-GnRH1) are shown in Table 1A, below. $^{111}$In-DOTA-Ahx-(D-Lys$^6$-GnRH1) exhibited rapid tumor uptake. The tumor uptake values were 1.76±0.58 and 0.29±0.10% ID/g at 0.5 and 2 h post-injection. The tumor uptake values decreased to 0.15±0.05 and 0.18±0.07% ID/g at 4 and 24 h post-injection. Blood clearance of $^{111}$In-DOTA-Ahx-(D-Lys$^6$-GnRH1) was fast. The blood uptake was 0.20±0.03% ID/g at 2 h post-injection. Meanwhile, whole-body clearance of $^{111}$In-DOTA-Ahx-(D-Lys$^6$-GnRH1) was rapid, with approximately 95% of the injected radioactivity cleared through the urinary system by 2 h post-injection. The renal uptake values were 15.39±4.59, 8.88±1.26, 9.28±1.18 and 4.43±1.67% ID/g at 0.5, 2, 4 and 24 h post-injection. Besides the kidneys, the liver was the normal organ with second high uptake after 2 h post-injection. The liver uptake values were 0.77±0.06, 0.97±0.13 and 0.59±0.16% ID/g at 2, 4 and 24 h post-injection. The tumor imaging properties of $^{111}$In-DOTA-Ahx-(D-Lys$^6$-GnRH1) were examined in MDA-MB-231 human breast cancer-xenografted nude mice. The three-dimensional, coronal and transversal SPECT/CT images are presented in FIG. 10. Flank MDA-MB-231 xenografted tumors were clearly visualized by SPECT/CT using $^{111}$In-DOTA-Ahx-(D-Lys$^6$-GnRH1) as an imaging probe in all three images. The whole-body image (FIG. 10A) showed high tumor to normal organ uptake ratios except for the kidneys and liver.

TABLE 1A

Biodistribution of $^{111}$In-DOTA-Ahx-(D-Lys$^6$-GnRH1) in MDA-MB-231 human breast cancer-xenografted nude mice. The data were presented as percent injected dose/gram or as percent injected dose (Mean ± SD, n = 5).

| Tissue | 0.5 h | 2 h | 4 h | 24 h |
|---|---|---|---|---|
| Percent injected dose/gram (% ID/g) | | | | |
| Tumor | 1.76 ± 0.58 | 0.29 ± 0.10 | 0.15 ± 0.05 | 0.18 ± 0.07 |
| Brain | 0.34 ± 0.28 | 0.03 ± 0.02 | 0.02 ± 0.01 | 0.03 ± 0.01 |
| Blood | 2.87 ± 0.71 | 0.20 ± 0.03 | 0.11 ± 0.02 | 0.04 ± 0.02 |
| Heart | 1.11 ± 0.19 | 0.13 ± 0.04 | 0.09 ± 0.06 | 0.10 ± 0.06 |
| Lung | 3.17 ± 0.69 | 0.28 ± 0.12 | 0.18 ± 0.10 | 0.11 ± 0.03 |
| Liver | 1.60 ± 0.29 | 0.77 ± 0.06 | 0.97 ± 0.13 | 0.59 ± 0.16 |
| Spleen | 0.80 ± 0.10 | 0.23 ± 0.04 | 0.39 ± 0.01 | 0.31 ± 0.11 |
| Stomach | 0.66 ± 0.37 | 0.31 ± 0.31 | 0.50 ± 0.56 | 0.04 ± 0.01 |
| Kidneys | 15.39 ± 4.59 | 8.88 ± 1.26 | 9.28 ± 1.18 | 4.43 ± 1.67 |
| Muscle | 0.51 ± 0.34 | 0.03 ± 0.03 | 0.12 ± 0.03 | 0.16 ± 0.02 |
| Pancreas | 0.55 ± 0.04 | 0.15 ± 0.02 | 0.13 ± 0.08 | 0.11 ± 0.08 |
| Bone | 0.72 ± 0.19 | 0.35 ± 0.26 | 0.70 ± 0.50 | 0.37 ± 0.26 |
| Skin | 3.07 ± 0.91 | 0.26 ± 0.04 | 0.24 ± 0.03 | 0.22 ± 0.05 |
| Uptake ratio of tumor/normal tissue | | | | |
| Tumor/blood | 0.61 | 1.45 | 1.36 | 4.50 |
| Tumor/muscle | 3.45 | 9.67 | 1.25 | 1.13 |
| Percent injected dose (% ID) | | | | |
| Intestines | 1.43 ± 0.10 | 0.42 ± 0.10 | 0.63 ± 0.21 | 0.16 ± 0.02 |
| Urine | 73.12 ± 5.36 | 94.61 ± 0.60 | 94.59 ± 0.27 | 96.81 ± 0.72 |

Discussion

There is considerable interest to develop receptor-targeting peptide radiopharmaceuticals for cancer imaging including breast cancer. For instance, radiolabeled bombesin (BBN) peptides[34-37] have been utilized to target the gastrin-releasing peptide (GRP) receptors for breast cancer imaging.

Both $^{99m}$Tc-Cyc-Aca-BBN(2-14)NH$_2$[34] and $^{99m}$Tc-RP527[35] have been successfully used to visualize breast cancer in human, confirming the feasibility of using receptor-targeting radiolabeled peptides for breast cancer detection. In this study, the GnRH receptor is an attractive molecular target due to its over-expression on human breast cancer cells as well as tissue samples[16-20]. Wild-type GnRH peptide (pGlu$^1$-His$^2$-Trp$^3$-Ser$^4$-Tyr$^5$-Gly$^6$-Leu$^7$-Arg$^8$-Pro$^9$-Gly$^{10}$-NH$_2$ SEQ ID NO: 1) can bend around the flexible Gly$^6$ for FnRH receptor binding. The substitution of Gly$^6$ with a D-amino acid enhances the binding affinity and reduces the metabolic clearance of the peptide[22]. It is known that both motifs of pGlu$^1$-His$^2$-Trp$^3$ and Arg$^8$-Pro$^9$-Glyo$^1$-NH$_2$ play crucial roles in GnRH receptor binding[21]. Several radiolabeled GnRH peptides have been reported over the past decade[38-40]. Initially, a bifunctional chelating agent (BFCA) of P$_2$S2-COOH {6,8-bis-[3-(bis(hydroxymethyl)phosphanyl)propylsulfanyl]octanoic acid} was conjugated to the epsilon amino group of D-Lys$^6$ in D-Lys$^6$-GnRH peptide for $^{99m}$Tc/$^{188}$Re radiolabeling[38]. The P$_2$S2-D-Lys$^6$-GnRH peptide was readily labeled with $^{99m}$Tc/$^{188}$Re with greater than 88% radiolabeling yields, demonstrating the feasibility of using the P$_2$S2-COOH as a BFCA for GnRH peptide radiolabeling with $^{99m}$Tc/$^{188}$Re. However, neither receptor binding affinities nor biodistribution properties were reported for $^{99m}$Tc/$^{188}$Re-P$_2$S2-D-Lys$^6$-GnRH[38]. Thereafter, a backbone metal cyclization strategy was employed to cyclize the N-terminus and C-terminus of the GnRH peptides to develop $^{99m}$Tc-labeled GnRH peptides[39]. Unfortunately, the backbone metal cyclization dramatically decreased the GnRH receptor binding affinities of the peptides, confirming that both N-terminus and C-terminus need to be reserved for strong GnRH receptor binding.

In 2008, $^{18}$F and $^{68}$Ga-labeled GnRH peptides were reported for GnRH receptor-targeting[40]. The motif of p-fluorobenzyloxime acetyl (FBOA) was conjugated to the epsilon amino group of D-Lys$^6$ in D-Lys$^6$-GnRH via the β-Alanine (β-Ala) or Ahx linker for $^{18}$F radiolabeling, whereas the DOTA was directly coupled to the epsilon amino group of D-Lys$^6$ in D-Lys$^6$-GnRH for $^{68}$Ga radiolabeling. The results on receptor binding affinity and internalization property indicated that the lipophilicity of the moiety attached to the D-Lys$^6$ showed a significant impact on both receptor binding affinity and internalization property. The Ahx linker was more lipophilic and better than the β-Ala linker in terms of maintaining high receptor binding affinity and high internalization percentage of the GnRH peptide. Direct coupling of the hydrophilic $^{68}$Ga-DOTA moiety to D-Lys$^6$-GnRH dramatically reduced the receptor binding affinity and internalization percentage of the peptide[36]. No biodistribution result was reported for $^{18}$F- and $^{68}$Ga-labeled GnRH peptides.

In this study, instead of direct coupling the DOTA to the D-Lys$^6$, we conjugated the DOTA to the D-Lys$^6$ via the Ahx linker to enhance the lipophilicity of the moiety attached to D-Lys$^6$-GnRH while remaining nanomolar GnRH receptor binding affinity of the peptide. Since both alpha and epsilon amino groups of D-Lys$^6$ can be used for DOTA conjugation, we separately conjugated the DOTA to each amino group of D-Lys$^6$ to determine which amino group was better for DOTA conjugation in terms of GnRH receptor binding affinity. The IC$_{50}$ values of DOTA-Ahx-(D-Lys$^6$-GnRH1) and DOTA-Ahx-(D-Lys$^6$-GnRH2) revealed that the epsilon amino group of D-Lys$^6$ was better than the alpha amino group in maintaining nanomolar GnRH receptor binding affinity. The conjugation of the DOTA to the alpha amino group of D-Lys$^6$ dramatically decreased the GnRH receptor binding affinity by 293-fold. Furthermore, we conjugated the DOTA to the epsilon amino group of L-Lys$^6$ via the Ahx linker to examine the potential impact of D- and L-configuration of the Lys$^6$ on the GnRH receptor binding affinity. The IC$_{50}$ values of DOTA-Ahx-(D-Lys$^6$-GnRH1) and DOTA-Ahx-(L-Lys$^6$-GnRH3) suggested that the D-configuration of the Lys$^6$ played a key role in maintaining the GnRH receptor binding affinity as well. The replacement of D-Lys$^6$ with L-Lys$^6$ sacrificed the GnRH receptor binding affinity by 119-fold. The dramatic differences in GnRH receptor binding affinities among these three novel GnRH peptides demonstrated the profound impact of the DOTA position on the binding affinity of the GnRH peptide.

Conclusion

In conclusion, the successful imaging of DU145 human prostate cancer-xenografted tumor lesions using $^{111}$In-DOTA-Ahx-(D-Lys$^6$-GnRH1) highlighted its potential as a novel imaging probe for human prostate cancer imaging. In addition, the DOTA position displayed a profound impact on the binding affinity of the GnRH peptide. The coupling of DOTA to the epsilon amino group of D-Lys$^6$ maintained nanomolar GnRH receptor binding affinity of the peptide, providing a new insight into the design of novel radiolabeled GnRH peptides. The successful imaging of MDA-MB-231 human breast cancer-xenografted tumor lesions using $^{111}$In-DOTA-Ahx-(D-Lys$^6$-GnRH1) highlighted its potential as a novel imaging probe for human breast cancer imaging.

REFERENCES AND NOTES (PROSTATE CANCER AND PROSTATE CANCER EXAMPLES)

1. Jemal, A.; Siegel, R.; Xu, J.; Ward, E. *CA Cancer J. Clin.* 2010, 60, 277.
2. Pienta, K. J.; Naik, H.; Lehr, J. E. *Urology* 1996, 48, 164.
3. Naik, H.; Lehr, J. E.; Pienta, K. J. *Urology* 1996, 48, 508.
4. Yogoda, A.; Petrylak, D. *Cancer* 1993, 71, 1098.
5. Crawford, E. D.; Blumenstein, B. A.; Goodman, P. J.; Davis, M. A.; Eisenberger, M.
A.; McLeod, D. G.; Spaulding, J. T.; Benson, R.; Don, F. A. *Cancer* 1990, 66 (suppl. 5), 1039.
6. Oesterling, J. E. *J. Urol.* 1991, 145, 907.
7. Hudson, M. A.; Bahnson, R. R.; Catalona, W. T. *J. Urol.* 1989, 142, 1011.
8. Stephan, C.; Cammann, H.; Meyer, H. A.; Lein, M.; Jung, K. *Cancer lett.* 2007, 249, 18.
9. Kahn, D.; Williams, R. D.; Seldin, D. W.; Libertino, J. A.; Hirschhorn, M.; Dreicer, R.; Weiner, G. J.; Bushnell, D.; Gulfo, J. *J. Urol.* 1994, 152, 1490.
10. Kahn, D.; William, R. D.; Manyak, M. J.; Haseman, M. K.; Seldin, D. W.; Libertino, J. A.; Maguire, R. T. *J. Urol.* 1998, 159, 2041.
11. Kahn, D.; Williams, R. D.; Haseman, M. K.; Reed, N. L.; Miller, S. J.; Gerstbrein, J. *J. Clin. Oncol.* 1998, 16, 284.
12. Hinkle, G. H.; Burgers, J. K.; Neal, C. E.; Texter, J. H.; Kahn, D.; Williams, R. D.; Maguire, R.; Rogers, B.; Olsen, J. O.; Badalament, R. A. *Cancer* 1998, 83, 739.
13. Chang, C. H.; Wu, H. C.; Tsai, J. J.; Shen, Y. Y.; Changlai, S. P.; Kao, A. *Urol. Int.* 2003, 70, 311.
14. Heicappell, R.; Muller-Mattheis, V.; Reinhardt, M.; Vosberg, H.; Gerharz, C. D.; Muller-Gartner, H.; Ackermann, R. *Eur. Urol.* 1999, 36, 582.
15. Shreve, P. D.; Grossmann, H. B.; Gross, M. D.; Wahl, R. L. *Radiology* 1996, 199, 751
16. Effert, P. J.; Bares, R.; Handt, S.; Wolff, J. M.; Bull, U.; Jakse, G. *J. Urol.* 1996, 155, 994.
17. Lirnonta, P.; Dondi, D.; Moretti, R. M.; Maggi, R.; Motta, M. *J. Clin. Endocrinol. Metab.* 1992, 75, 207.
18. Lirnonta, P.; Dondi, D.; Moretti, R. M.; Fermo, D.; Garattini, E.; Motta, M. *J. Clin. Endocrinol. Metab.* 1993, 76, 797.
19. Dondi, D.; Limonta, P.; Moretti, R. M.; Montagnani, M. M.; Garattini, E.; Motta, M. *Cancer Res.* 1994, 54, 4091.
20. Limonta, P.; Moretti, R. M.; Montagnani, M. M.; Dondi, D.; Parenti, M.; Motta, M. *Endocrinology* 1999, 140, 5250.

21. Straub, B.; Muller, M.; Krause, H.; Schrader, M.; Goessl, C.; Heicappell, R.; Miller, K. *Clin. Cancer Res.* 2001, 7, 2340.
22. Halmos, G.; Arencibia, J. M.; Schally, A. V.; Davis, R.; Bostwick, D. G. *J. Urol.* 2000, 163, 623.
23. Tieva, A.; Stattin, P.; Wikstrom, P.; Bergh, A.; Damber, J. E. *Prostate* 2001, 47, 276.
24. Fekete, M.; Zalatnai, A.; Comaru-Schally, A. M.; Schally, A. V. *Pancreas* 1989, 4, 521.
25. Grundker, C.; Volker, P.; Griesinger, F.; Ramaswamy, A.; Nagy, A.; Schally, A. V.; Emons, G. *Am. J. Obstet. Gynecol.* 2002, 187, 528.
26. Millar, R. P. *Animal Reproduction Sci.* 2005, 88, 5.
27. Barda, Y.; Cohen, N.; Lev, V.; Ben-Aroya, N.; Koch, Y.; Mishani, E.; Fridkin, M.; Gilon, C. *Nucl. Med. Biol.* 2004, 31, 921.
28. Beckers, T.; Bernd, M.; Kutscher, B.; Kuhne, R.; Hoffman, S.; Reissmann, T. *Biochem. Biophys. Res. Commun.* 2001, 289, 653.
29. Guo, H.; Lu, J.; Hathaway, H.; Royce, M. E.; Prossnitz, E. R.; Miao, Y. *Bioconjug. Chem.* 2011, in press.
30. Schottelius, M.; Berger, S.; Poethko, T.; Schwaiger, M.; Wester, H. J. *Bioconjug. Chem.* 2008, 19, 1256.
31. Guo, H.; Yang, J.; Gallazzi, F.; Prossnitz, E. R.; Sklar, L. A.; Miao, Y. *Bioconjug. Chem.* 2009, 20, 2162.
32. Hoffman, T. J.; Gali, H.; Smith, C. J.; Sieckman, G. L.; Hayes, D. L.; Owen, N. K.; Volkert, W. A. *J. Nucl. Med.* 2003, 44, 823.
33. Specific GnRH receptor binding of $^{111}$In-DOTA-Ahx-(D-Lys$^6$-GnRH1): DOTA-Ahx-(D-Lys$^6$-GnRH1) was synthesized and radiolabeled with $^{111}$In according to our published procedure.[29] The specific GnRH receptor binding of $^{111}$In-DOTA-Ahx-(D-Lys$^6$-GnRH1) was determined using Millipore ChemiScreen™ human GnRH membrane preparations (Millipore, Inc., Billerica, Mass.). Briefly, 50 μL of human GnRH membrane preparations were incubated at 25° C. for 3 h with approximately 60,000 cpm of HPLC-purified $^{111}$In-DOTA-Ahx-(D-Lys$^6$-GnRH1) in 50 μL, of binding medium {50 mM N-(2-hydroxyethyl)-piperazine-N'-(2-ethanesulfonic acid), 5 mM $MgCl_2$, 1 mM $CaCl_2$, pH 7.4, 0.2% bovine serum albumin (BSA)} with or without 1 μM of DOTA-Ahx-(D-Lys$^6$-GnRH1) peptide blockade. After the incubation, each membrane preparation was mixed with 800 μL of ice-cold washing buffer first, and then filtered through a GF/C filter (Waterman, Clifton, N.J.) pre-soaked in 1% polyethylenimine. Each filter was rinsed with 1 mL of ice-cold washing buffer for three times and counted in a Wallac 1480 automated gamma counter (PerkinElmer, Waltham, Mass.). Statistical analysis was performed using the Student's t-test for unpaired data to determine the significance of differences between the GnRH receptor binding of $^{111}$In-DOTA-Ahx-(D-Lys$^6$-GnRH1) with or without 1 μM of DOTA-Ahx-(D-Lys$^6$-GnRH1) blockade. Difference at the 95% confidence level ($p<0.05$) was considered significant.
34. Immunohistochemistry staining of DU145 human prostate cancer-xenografted tumor: The immunohistochemistry staining was performed on DU145 human prostate cancer-xenografted tumors to demonstrate the GnRH receptor expression. DU145 human prostate cancer cells were obtained from American Type Culture Collection (Manassas, Va.). GnRHR antibody (N-20, sc-8682) and the goat ABC staining system (sc-2023) were purchased from Santa Cruz Biotechnology, Inc (Santa Cruz, Calif.) for immunohistochemistry (IHC) staining of DU145 human prostate cancer-xenografted tumor. The DU145 human prostate cancer-xenografted tumors were generated through flank subcutaneous inoculations of DU145 cells ($1\times10^7$ cells/mouse) in male athymic nude mice. The tumor weights reached approximately 0.3 g at 18 days post cell inoculation. The immunoperoxidase staining of the xenografted DU145 tumor slices (4-μm thickness) were performed according to the protocol of goat ABC staining system. Briefly, the tumor slices were treated with 3% $H_2O_2$ for 15 min followed by a 20 min-treatment with the blocking serum at 25° C. Then, the tumor slices were incubated with primary goat anti-human GnRH antibody (1:40) for 1.75 h at 25° C. Thereafter, the tumor slices were incubated with biotinylated secondary antibody for 30 min and followed by a 30 min-incubation with AB enzyme reagent. The tumor slices were incubated with the peroxidase substrate for 5 min followed by a dehydration process using ethanol and xylene. After the immunoperoxidase staining, the tumor slices were washed with de-ionized water and counterstained with Gill's formulation #2 hematoxylin. One to two drops of DPX permanent mounting medium were immediately added to the tumor slices after the counterstaining. Then, the tumor slices were covered with glass coverslips and observed by the light microscopy. As controls, the xenografted DU145 tumor slices (4-μm thickness) were incubated (without primary goat anti-human GnRH antibody) with secondary biotinylated antibody, AB enzyme reagent and peroxidase substrate, respectively.
35. Biodistribution and tumor imaging of $^{111}$In-DOTA-Ahx-(D-Lys$^6$-GnRH1): All the animal studies were conducted in compliance with Institutional Animal Care and Use Committee approval. The pharmacokinetics of $^{111}$In-DOTA-Ahx-(D-Lys$^6$-GnRH1) was determined in DU145 human prostate cancer-xenografted male athymic nude mice (Harlan, Indianapolis, Ind.). The nude mice were subcutaneously inoculated with $1\times10^7$ DU145 cells on the right flank of each mouse to generate DU145 xenografted tumors. The tumor weights reached approximately 0.3 g at 18 days post cell inoculation. Each tumor-bearing mouse was injected with 0.037 MBq of $^{111}$In-DOTA-Ahx-(D-Lys$^6$-GnRH1) via the tail vein. Groups of 5 mice were sacrificed at 0.5, 2, 4 and 24 h post-injection, and tumors and organs of interest were harvested, weighed and counted. Blood values were taken as 6.5% of the whole-body weight. To determine the tumor imaging property of $^{111}$In-DOTA-Ahx-(D-Lys$^6$-GnRH1), approximately 33.3 MBq of $^{111}$In-DOTA-Ahx-(D-Lys$^6$-GnRH1) was injected into a DU145 human prostate cancer-xenografted nude mouse (18 days post the cell inoculation) via the tail vein. The mouse was sacrificed for small animal SPECT/CT (Nano-SPECT/CT®, Bioscan) imaging at 0.5 h post-injection. The CT imaging was immediately followed by the whole-body SPECT imaging. The SPECT scans of 24 projections were acquired. Reconstructed SPECT and CT data were visualized and co-registered using InVivoScope (Bioscan, Washington D.C.).
36. Urinary metabolites of $^{111}$In-DOTA-Ahx-(D-Lys$^6$-GnRH1): One hundred microliters of HPLC purified $^{111}$In-DOTA-Ahx-(D-Lys$^6$-GnRH1) (2.4 MBq) was injected into a DU145 human prostate cancer-xenografted nude mouse through the tail vein. At 2 h post-injection, the mouse was sacrificed and the urine was collected for metabolites analysis. The urine was centrifuged at 16,000 g for 5 min prior to the HPLC analysis. The radioactive metabolites in the urine were analyzed by injecting aliquots of the urine into HPLC. A 20-minute gradient of 15-25% acetonitrile/20 mM HCl was used for the urine analysis.

REFERENCES—BREAST CANCER AND BREAST CANCER EXAMPLES (1) Jemal, A., Siegel, R., Xu, J., and Ward, E. (2010) Cancer statistics. *CA Cancer J. Clin.* 60, 277-300.

(2) Buist, D. S., Porter, P. L., Lehman, C., Taplin, S. H., and White, E. (2004) Factors contributing to mammography failure in women aged 40-49 years. *J. Natl. Cancer Inst.* 96, 1432-1440.

(3) Gambhir, S. S. (2002) Molecular imaging of cancer with positron emission tomography. *Nat. Rev. Cancer* 2, 683-693.

(4) Sharma, V., Luker, G. D., and Piwnica-Worms, D. (2002) Molecular imaging of gene expression and protein function in vivo with PET and SPECT. *J. Magn. Reson. Imaging* 16, 336-351.

(5) Bos, R., van Der Hoeven, J. J., van Der Wall, E., van Der Groep, P., van Diest, P. J., Comans, E. F., Joshi, U., Semenza, G. L., Hoekstra, O. S., Lammertsma, A. A., and Molthoff, C. F. (2002) Biologic correlates of $^{18}$fluorodeoxyglucose uptake in human breast cancer measured by positron emission tomography. *J. Clin. Oncol.* 20, 379-387.

(6) Avril, N., Menzel, M., Dose, J., Schelling, M., Weber, W., Janicke, F., Nathrath, W., and Schwaiger, M. (2001) Glucose metabolism of breast cancer assessed by $^{18}$F-FDG PET: histologic and immunohistochemical tissue analysis. *J Nucl. Med.* 42, 9-16.

(7) Mankoff, D. A., Dunnwald, L. K., Gralow, J. R., Ellis, G. K., Charlop, A., Lawton, T. J., Schubert, E. K., Tseng, J., and Livingston, R. B. (2002) Blood flow and metabolism in locally advanced breast cancer: relationship to response to therapy. *J. NucL Med.* 43, 500-509.

(8) Oshida, M., Uno, K., Suzuki, M., Nagashima, T., Hashimoto, H., Yagata, H., Shishikura, T., Imazeki, K., and Nakajima, N. (1998) Predicting the prognoses of breast carcinoma patients with positron emission tomography using 2-deoxy-2-fluoro [$^{18}$F]-D-glucose. *Cancer* 90, 2227-2234.

(9) Inoue, T., Yutani, K., Taguchi, T., Tamaki, Y., Shiba, E., and Noguchi, S. (2004) Preoperative evaluation of prognosis in breast cancer patients by [(18)F]-Deoxy-2-fluoro-D-glucose-positron emission tomography. *J Cancer Res. Clin. Oncol.* 130, 273-278.

(10) Avril, N., Rose, C. A., Schelling, M., Dose, J., Kuhn, W., Bense, S., Weber, W., Ziegler, S., Graeff, H., and Schwaiger, M. (2000) Breast imaging with positron emission tomography and fluorine-18 fluorodeoxyglucose: use and limitations. *J Clin. Oncol.* 18, 3495-3502.

(11) Eubank, W. B., Mankoff, D. A., Takasugi, J., Vesselle, H., Eary, J. F., Shanley, T. J., Gralow, J. R., Charlop, A., Ellis, G. K., Lindsley, K. L., Austin-Seymour, M. M., Funkhouser, C. P., and Livingston, R. B. (2001)$^{18}$Fluorodeoxyglucose positron emission tomography to detect mediastinal or internal mammary metastases in breast cancer. *J Clin. Oncol.* 19, 3516-3523.

(12) Isasi, C. R., Moadel, R. M., and Blaufox, M. D. (2005) A meta-analysis of FDG PET for the evaluation of breast cancer recurrence and metastases. *Breast Cancer Res. Treat.* 90, 105-112.

(13) Lonneux, M., Borbath, I. I., Berliere, M., Kirkove, C., and Pauwels, S. (2000) The place of whole-body PET FDG for the diagnosis of distant recurrence of breast cancer. *Clin. Positron Imaging* 3, 45-49.

(14) Vranjesevic, D., Filmont, J. E., Meta, J., Silverman, D. H., Phelps, M. E., Rao, J., Valk, P. E., and Czernin, J. (2002) Whole-body (18)F-FDG PET and conventional imaging for predicting outcome in previously treated breast cancer patients. *J. Nucl. Med.* 43, 325-329.

(15) Cook, G. J., Houston, S., Rubens, R., Maisey, M. N., and Fogelman, I. (1998) Detection of bone metastases in breast cancer by $^{18}$FDG PET: differing metabolic activity in osteoblastic and osteolytic lesions. *J. Clin. Oncol.* 16, 3375-3379.

(16) Miller, W. R., Scott, W. N., Morris, R., Fraser, H. M., and Sharpe, R. M. (1985) Growth of human breast cancer cells inhibited by a luteinizing hormone-releasing hormone agonist. *Nature* 313, 231-233.

(17) Eidne, K. A., Flanagan, C. A., and Millar, R. P. (1985) Gonadotropin-releasing hormone binding sites in human breast carcinoma. *Science* 229, 989-991.

(18) Sharoni, Y., Bosin, E., Miinster, A., Levy, J., and Schally, A. V. (1989) Inhibition of growth of human mammary tumor cells by potent antagonists of luteinizing hormone-releasing hormone. *Proc. Natl. Acad. Sci. U.S.A.* 86, 1648-1651.

(19) Fekete, M., Wittliff, J. L., and Schally, A. V. (1989) Characteristics and distribution of receptors for [d-Trp6]-luteinizing hormone-releasing hormone, somatostatin, epidermal growth factor and sex steroids in 500 biopsy samples of human breast cancer. *J. Clin. Lab. Anal.* 3, 137-147.

(20) Baumann, K. H., Kiesel, L., Kaufmann, M., Bastert, G., and Runnebaum, B. (1993) Characterization of binding sites for a GnRH-agonist (buserelin) in human breast cancer biopsies and their distribution in relation to tumor parameters. *Breast Cancer Res. Treat.* 25, 37-46.

(21) Millar, R. P. (2005) GnRH and GnRH receptors. *Animal Reproduction Sci.* 88, 5-28.

(22) Beckers, T., Berrid, M., Kutscher, B., Kuhne, R., Hoffman, S., and Reissmann, T. (2001) Structure-function studies of linear and cyclized peptide antagonists of the GnRH receptor. *Biochem. Biophys. Res. Commun.* 289, 653-663.

(23) Nagy, A., Schally, A. V., Armatis, P., Szepeshazi, K., Halmos, G., Kovacs, M., Zarandi, M., Groot, K., Miyazaki, M., Jungwirth, A., and Horvath, J. (1996) Cytotoxic analogs of luteinizing hormone-releasing hormone containing doxorubicin or 2-pyrrolinodoxorubicin, a derivative 500-1000 times more Potent. *Proc. Nati. Acad. Sci. U.S.A.* 93, 7269-7273.

(24) Halmos, G., Nagy, A., Lamharzi, N., and Schally, A. V. (1999) Cytotoxic analogs of luteinizing hormone-releasing hormone bind with high affinity to human breast cancers. *Cancer Lett.* 136, 129-136.

(25) Wang, X., Krebs, L. J., Al-Nuri, M., Pudavar, H. E., Ghosal, S., Liebow, C., Nagy, A. A., Schally, A. V., and Prasad, P. N. (1999) A chemically labeled cytotoxic agent: two-photon fluorophore for optical tracking of cellular pathway in chemotherapy. *Proc. Natl. Acad. Sci. U.S.A.* 96, 11081-11084.

(26) Szepeshazi, K., Schally, A. V., Nagy, A., Halmos, G., and Groot, K. (1997) Targeted cytotoxic luteinizing hormone releasing hormone (LH-RH) analogs inhibit growth of estrogen-independent MXT mouse mammary cancer in vivo by decreasing cell proliferation and inducing apoptosis. *Anticancer Drugs* 8, 974-987.

(27) Szepeshazi, K., Schally, A. V., and Nagy, A. (1999) Effective treatment of advanced estrogen-independent MXT mouse mammary cancers with targeted cytotoxic LH-RH analogs. *Breast Cancer Res. Treat.* 56, 267-276.

(28) Kahan, Z., Nagy, A., Schally, A. V., Halmos, G., Arencibia, J. M., and Groot, K. (1999) Complete regression of MX-1 human breast cancer xenografts after targeted chemotherapy with a cytotoxic analog of luteinizing hormone-releasing hormone, AN-207. *Cancer* 85, 2608-2615.

(29) Bajo, A. M., Schally, A. V., Halmos, G., and Nagy, A. (2003) Targeted doxorubicincontaining luteinizing hormone-releasing hormone analogue AN-152 inhibits the growth of doxorubicin-resistant MX-1 human breast cancers. *Clin. Cancer Res.* 9, 3742-3748.

(30) Kahan, Z., Nagy, A., Schally, A. V., Halmos, G., Arencibia, J. M., and Groot, K. (2000) Administration of a targeted cytotoxic analog of luteinizing hormone releasing hormone inhibits growth of estrogen independent MDA-MB-231 human breast cancers in nude mice. *Breast Cancer Res. Treat.* 59, 255-262.

(31) Chatzistamou, I., Schally, A. V., Nagy, A., Armatis, P., Szepeshazi, K., and Halmos, G. (2000) Effective treatment of metastatic MDA-MD-435 human estrogen independent breast carcinomas with a targeted cytotoxic analog of luteinizing hormone-releasing hormone, AN-207. *Clin. Cancer Res.* 6, 4158-4165.

(32) Flanagan, C. A., Fromme, B. J., Davidson, J. S., and Millar, R. P. (1998) A high affinity gonadotropin-releasing hormone (GnRH) tracer, radioiodinated at position 6, facilitates analysis of mutant GnRH receptors. *Endocrinology* 139, 4115-4119.

(33) Guo, H., Yang, J., Gallazzi, F., and Miao, Y. (2010) Reduction of the ring size of radiolabeled lactam bridige-cyclized α-MSH peptide, resulting in enhanced melanoma uptake. *J Nucl. Med.* 51, 418-426.

(34) Scopinaro, F., Varvarigou, A. D., Ussof, W., De Vincentis, G., Sourlingas, T. G., Evangelatos, G. P., Datsteris, J., and Archimandritis, S. C. (2002) Technetium-labeled bombesin-like peptide: preliminary report on breast cancer uptake in patients. *Cancer Biother. Radiopharm.* 17, 327-335.

(35) Van de Wiele, C., Dumont, F., Broecke, R. V., Oosterlinck, W., Cocquyt, V., Serreyn, R., Peers, S., Thornback, J., Slegers, G., and Dierck, R. A. (2000) Technetium-99m RP527, a GRP analogue for visualization of GRP receptor-expressing malignancies: a feasibility study. *Eur. J. Nucl. Med.* 27, 1694-1699.

(36) Prasanphanich, A. F., Retzloff, L., Lane, S. R., Nanda, P. K., Sieckman, G. L., Rold, T. L., Ma, L., Figueroa, S. D., Sublett, S. V., Hoffman, T. J., Smith, C. J. (2009) In vitro and in vivo analysis of [$^{64}$Cu—NO$_2$A-8-Aoc-BBN(7-14)NH$_2$]: a site-directed radiopharmaceutical for positron-emission tomography imaging of T-47D human breast cancer tumors. *Nucl. Med. Biol.* 36, 171-181.

(37) Retzloff, L., Heinzke, L., Figueroa, S. D., Sublett, S. V., Ma, L., Sieckman, G. L., Rold, T. L., Santos, I., Hoffman, T. J., Smith, C. J. (2010) Evaluation of [$^{99m}$Tc-(CO)$_3$—X—Y-Bombesin(7-14)NH$_2$] conjugates for targeting gastrin-releasing peptide receptors overexpressed on breast carcinoma. *Anticancer Res.* 30, 19-30.

(38) Gali, H., Hoffman, T. J., Sieckman, G. L., Owen, N. K., Katti, K. V., and Volkert, W. A. (2001) Synthesis, characterization, and labeling with $^{99m}$Tc/$^{188}$Re of peptide, conjugates containing a dithia-bisphosphine chelating agent. *Bioconjug. Chem.* 12, 354-63.

(39) Barda, Y., Cohen, N., Lev, V., Ben-Aroya, N., Koch, Y., Mishani, E., Fridkin, M., and Gilon, C. (2004) Backbone metal cyclization: novel $^{99m}$Tc labeled GnRH analog as potential SPECT molecular imaging agent in cancer. *Nucl. Med. Biol.* 31, 921-933.

(40) Schottelius, M., Berger, S., Poethko, T., Schwaiger, M., and Wester, H. J. (2008) Development of novel $^{68}$Ga- and $^{18}$F-labeled GnRH-I analogues with high GnRHR-targeting efficiency. *Bioconjug. Chem.* 19, 1256-1268.

(41) Guo, H., Yang, J., Gallazzi, F., Prossnitz, E. R., Sklar, L. A., and Miao, Y. (2009) Effect of DOTA position on melanoma targeting and pharmacokinetic properties of $^{111}$In-labeled lactam bridge-cyclized alpha-melanocyte stimulating hormone peptide. *Bioconjug. Chem.* 20, 2162-2168.

(42) Hoffman, T. J., Gali, H., Smith, C. J., Sieckman, G. L., Hayes, D. L., Owen, N. K., and Volkert, W. A. (2003) Novel series of $^{111}$In-labeled bombesin analogs as potential radiopharmaceuticals for specific targeting of gastrin-releasing peptide receptors expressed on human prostate cancer cells. *J. Nucl. Med.* 44, 823-831.

The invention claimed is:

1. A compound according to the chemical structure:

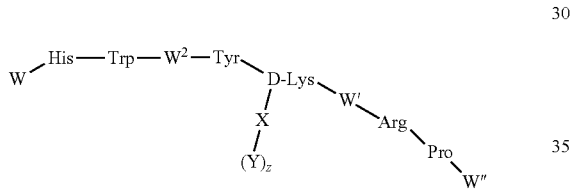

where W is aspartic acid, glutamic acid or pyroglutamic acid;

$W^2$ is serine or threonine;

W' is glycine, alanine, leucine, isoleucine or valine;

W" is glycine or alanine;

Y is a chelate group selected from the group consisting of 1,4,7,10-tetraazacyclododecane-1,4,7,10-tetraacetic acid (DOTA), 4,11-bis(carboxymethyl)-1,4,8,11-tetraazabicyclo[6.6.2]hexadecane (CB-TE2A), 1,4,7-triazacyclononane-1,4,7-triacetic acid (NOTA), Diethylenetriaminepentaacetic acid (DTPA), Mercaptoacetyltriglycine (MAG₃), 4,5-bis(2-mercaptoacetamido)pentanoic, hydrazinonicotinamide/6-hydrazinopyridine-3-carboxylic acid (HYNIC) and HYNIC in combination with tricine or ethylenediaminediacetic acid (EDDA) as a coligand;

X is independently an amino acid linker of the chemical structure:

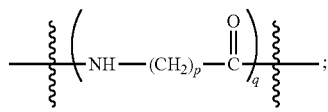

an alkylene oxide group according to the chemical structure:

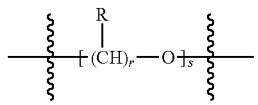

where each R is independently selected from H or a $C_1$-$C_3$ alkyl group, a $C_1$-$C_{25}$ hydrocarbon which is linear, branched or cyclic and which may be optionally saturated or contain one or more unsaturated carbon-carbon bonds, or an amino acid group containing from 1 to about 25 amino acid residues in length, wherein said amino acid residues are selected from the group consisting of glycine, alanine, leucine, isoleucine, valine, serine, threonine, phenylalanine, D-phenylalanine or a mixture thereof;

p is an integer from 1 to 25;

q is an integer from 1 to 25;

r is an integer from 2 to 6;

s is an integer from 1 to 25; and z is an integer from 1 to 5, or a pharmaceutically acceptable salt thereof, optionally complexed with at least one radioisotope.

2. The compound according to claim 1 wherein W is glutamic acid or pyroglutamic acid.

3. The compound according to claim 1 wherein $W^2$ is serine.

4. The compound according to claim 1 wherein W is pyroglutamic acid.

5. The compound according to claim 1 wherein W' is leucine or isoleucine.

6. The compound according to claim 1 wherein W" is glycine.

7. The compound according to claim 1 wherein said amino acid group comprises amino acid units selected from the group consisting of glycine, alanine, serine or mixtures thereof.

8. The compound according to claim 1 wherein said amino acid group is a polyglycine comprising from 3 to 8 glycine units.

9. The compound according to claim 1 wherein p is 2 to 8.

10. The compound according to claim 1 wherein q is 1 or 2.

11. The compound according to claim 1 wherein q is 1 or 2 when p is 2 to 8 or q is an integer from 5 to 25 when p is 1 or 2.

12. The compound according to claim 1 wherein z is 1 to 5.

13. The compound according to claim 1 wherein Y is a chelate group selected from the group consisting of DOTA, NOTA, MAG3, (HYNIC) and HYNIC in combination with tricine or ethylenediaminediacetic acid (EDDA) as a coligand.

14. The compound according to claim 13 wherein said chelate group is DOTA.

15. The compound according to claim 1 wherein said radioisotope is selected from the group consisting of $^{86}Y$, $^{90}Y$, $^{111}In$, $^{177}Lu$, $^{225}Ac$, $^{212}Bi$, $^{213}Bi$, $^{66}Ga$, $^{67}Ga$, $^{68}Ga$, $^{64}Cu$, $^{67}Cu$, $^{71}As$, $^{72}As$, $^{76}As$, $^{77}As$, $^{65}Zn$, $^{48}V$, $^{203}Pb$, $^{209}Pb$, $^{212}Pb$, $^{166}Ho$, $^{149}Pm$, $^{153}Sm$, $^{201}Tl$, $^{188}Re$, $^{186}Re$ and $^{99m}Tc$.

16. The compound according to claim 15 wherein said radioisotope is polycationic.

17. The compound according to claim 1 wherein said radioisotope is selected from the group consisting of $^{90}Y$, $^{177}Lu$, $^{186}Re$, $^{188}Re$, $^{212}Bi/^{212}Pb$, $^{213}Bi$, $^{149}Pm$, $^{166}Ho$ and $^{153}Sm$.

18. The compound according to claim 1 wherein said radioisotope is selected from the group consisting of $^{111}In$, $^{86}Y$, $^{66}Ga$, $^{67}Ga$, $^{68}Ga$, $^{203}Pb$, $^{64}Cu$ and $^{99m}Tc$.

19. A compound of the chemical structure:

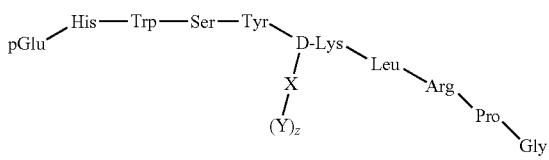

where Y is a DOTA chelate group, z is 1, and
X is an amino acid linker according to the chemical structure:

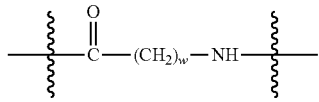

or a polyglycine group having between 3 and 6 glycine residues; and
w is an integer from 2 to 8; or
a pharmaceutically acceptable salt thereof,
which is complexed with a radioisotope.

20. The compound according to claim 19 wherein said radioisotope is $^{111}In$.

21. The compound according to claim 19 which is:

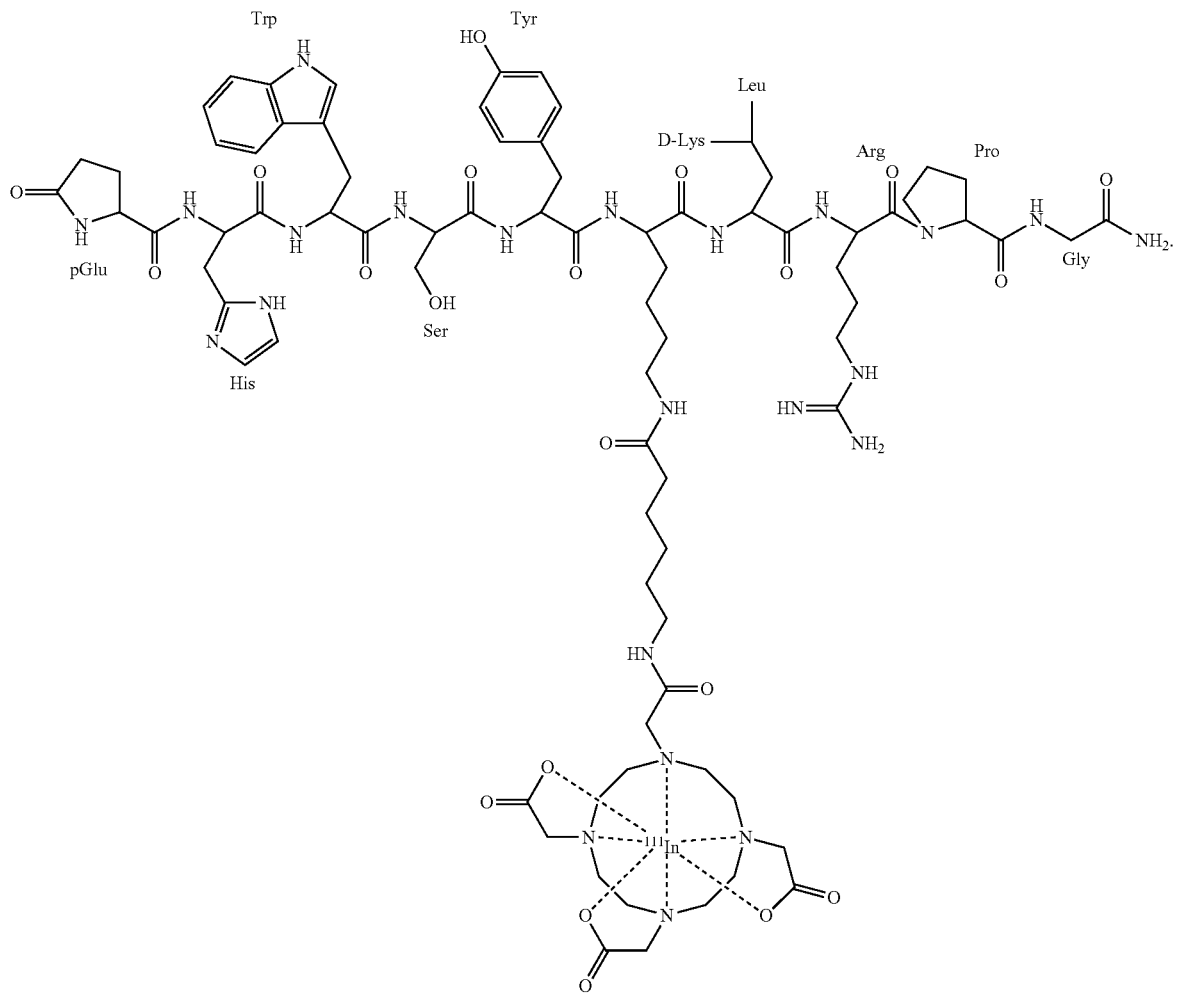

22. A pharmaceutical composition comprising an effective amount of a compound according to claim 1 complexed with a radioisotope in combination with a pharmaceutically acceptable carrier, additive or excipient.

23. The composition according to claim 22 in parenteral dosage form.

24. The composition according to claim 22 in intravenous dosage form.

25. The composition according to claim 22 wherein said compound is combined with at least one additional anticancer agent.

26. The composition according to claim 25 wherein said additional anticancer agent is everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR, KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, gleevac, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258,); vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dicarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291ss, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa or a mixtures thereof.

27. A method of diagnosing the existence or absence of cancer in a patient at risk for cancer comprising administering to said patient a compound according to claim 1; imaging said patient to determine if tissue in said patient exhibits elevated expression of GnRH receptors; and diagnosing said patient as having cancer if said tissue evidences elevated expression of GnRH receptors in comparison to a standard.

28. The method according to claim 27 wherein said cancer is a metastatic cancer.

29. The method according to claim 27 wherein said cancer is prostate cancer, ovarian cancer, breast cancer, cervical cancer, uterine cancer, placental cancer melanoma, stomach, colon, rectal, liver, pancreatic, lung, uteri, testis, bladder, renal, brain/CNS, head and neck, throat, Hodgkin's disease, non-Hodgkin's lymphoma, multiple myeloma, leukemia, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer or lymphoma.

30. The method according to claim 27 wherein said imaging is conducted using single photon emission computed tomography (SPECT) and positron emission tomography (PET).

31. A method of treating a cancer which overexpresses GnRH in a patient in need of therapy comprising administering to said patient an effective amount a composition according to claim 22.

32. The method according to claim 31 wherein said cancer is prostate cancer, ovarian cancer, breast cancer, cervical cancer, uterine cancer, placental cancer, melanoma, stomach, colon, rectal, liver, pancreatic, lung, uteri, testis, bladder, renal, brain/CNS, head and neck, throat, Hodgkin's disease, non-Hodgkin's lymphoma, multiple myeloma, leukemia, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer or lymphoma.

33. A method of monitoring therapy of a patient in the treatment of a cancer comprising administering to a patient undergoing cancer treatment an imaging effective amount of a compound according to claim 1, imaging said patient to determine if tissue in said patient exhibits elevated expression of GnRH receptors; and comparing the results of said imaging step with a standard.

* * * * *